(12) United States Patent
Wilton et al.

(10) Patent No.: US 11,441,148 B2
(45) Date of Patent: Sep. 13, 2022

(54) MODULATORS AND MODULATION OF THE RECEPTOR FOR ADVANCED GLYCATION END-PRODUCTS RNA

(71) Applicants: MONASH UNIVERSITY, Clayton (AU); MURDOCH UNIVERSITY, Murdoch (AU)

(72) Inventors: Stephen Wilton, Murdoch (AU); Merlin Christopher Thomas, Clayton (AU); Carlos Rosado, Clayton (AU); Raelene Jane Pickering, Clayton (AU)

(73) Assignees: MONASH UNIVERSITY, Clayton (AU); MURDOCH UNIVERSITY, Murdoch (AU)

( * ) Notice: Subject to any disclaimer, the term of this patent is extended or adjusted under 35 U.S.C. 154(b) by 0 days.

(21) Appl. No.: 17/411,932

(22) Filed: Aug. 25, 2021

(65) Prior Publication Data
US 2021/0388363 A1 Dec. 16, 2021

Related U.S. Application Data

(63) Continuation of application No. PCT/AU2020/050449, filed on May 7, 2020.

(30) Foreign Application Priority Data

| May 14, 2019 | (AU) | ................................ 2019901641 |
| Jun. 17, 2019 | (AU) | ................................ 2019902095 |
| Aug. 2, 2019 | (AU) | ................................ 2019902772 |
| Oct. 16, 2019 | (AU) | ................................ 2019903900 |

(51) Int. Cl.
*C12N 15/113* (2010.01)
*C12Q 1/68* (2018.01)

(52) U.S. Cl.
CPC ...... *C12N 15/1138* (2013.01); *C12N 2310/11* (2013.01); *C12N 2310/315* (2013.01); *C12N 2310/321* (2013.01); *C12N 2310/3233* (2013.01); *C12N 2310/3513* (2013.01); *C12N 2320/30* (2013.01); *C12N 2320/33* (2013.01)

(58) Field of Classification Search
None
See application file for complete search history.

(56) References Cited

U.S. PATENT DOCUMENTS

| 4,458,066 | A | 7/1984 | Caruthers et al. |
| 5,149,797 | A | 9/1992 | Pederson et al. |
| 6,287,860 | B1 | 9/2001 | Monia et al. |
| 6,806,084 | B1 | 10/2004 | Debs et al. |
| 6,887,906 | B1 | 5/2005 | Teng et al. |
| 6,965,025 | B2 | 11/2005 | Gaarde et al. |
| 6,969,400 | B2 | 11/2005 | Rhee et al. |
| 2003/0027780 | A1 | 2/2003 | Hardee et al. |
| 2004/0248833 | A1 | 12/2004 | Emanuele et al. |
| 2010/0016215 | A1 | 1/2010 | Moulton et al. |
| 2021/0246454 | A1* | 8/2021 | Lykens .................. A01K 67/02 |

FOREIGN PATENT DOCUMENTS

| JP | 2010233542 A | 11/2010 |
| WO | 2019222693 A1 | 11/2019 |

OTHER PUBLICATIONS

Aartsma-Rus, A. et al., "Antisense-mediated exon skipping: A versatile tool with therapeutic and research applications," (2007) RNA, vol. 13(10), p. 1609-1624.
Anderson, "Human Gene Therapy," (1992) Science 256:808-813.
Ando, R. et al., "Involvement of advanced glycation end product-induced asymmetric dimethylarginine generation in endothelial dysfunction," (2013) Diabetes & Vascular Disease Research, vol. 10(5), p. 436-441.
Barteau et al., "Physicochemical Parameters of Non-Viral Vectors that Govern Transfection Efficiency," (2008) Curr Gene Ther; 8(5):313-23.
Beaucage, et al., "Deoxynucleoside Phosphoramidites—A New Class of Key Intermediates for Deoxypolynucleotide Synthesis," (1981) Tetrahedron Letters, 22:1859-1862.
Brigham, et al., "Rapid Communication: In vivo Transfection of Murine Lungs with a Functioning Prokaryotic Gene using a Liposome Vehicle," (1989) Am. J. Med. Sci., 298:278-311.
Dokka and Rojanasakul, "Novel non-endocytic delivery of antisense oligonucleotides," (2000) Advanced Drug Delivery Reviews 44, 35-49.
Fraley, et al., "New generation liposomes: the engineering of an efficient vehicle for intracellular delivery of nucleic acids," (1981) Trends Biochem. Sci. 6:77.
Friedmann, "Progress toward human gene therapy," (1989) Science, 244:1275-1280.
Gebski et al., "Morpholino antisense oligonucleotide induced dystrophin exon 23 skipping in mdx mouse muscle," (2003) Human Molecular Genetics, 12(15): 1801-1811.
Hazinski, et al., "Localization and induced Expression of Fusion Genes in the Rat Lung," (1991) Am. J. Resp. Cell Molec. Biol., 4:206-209.
Hori, O. et al., "The Receptor for Advanced Glycation End Products (RAGE) is a Cellular Binding Site for Amphoterin," (1995) The Journal of Biological Chemistry, vol. 270(43), p. 25752-25761.
Jearawiriyapaisarn et al., "Sustained Dystrophin Expression Induced by Peptide-conjugated Morpholino Oligomers in the Muscles of mdx Mice," (2008) Mol. Ther. 16 9, 1624-1629.
Kalea, A. et al., "Alternative splicing of RAGE: roles in biology and disease," (2011) Frontiers in Bioscience, vol. 16, p. 2756-2770.
Kuniyasu, H. et al., "Differential Effects Between Amphoterin and Advanced Glycation End Products on Colon Cancer Cells," (2003) International Journal of Cancer, vol. 104, p. 722-727.

(Continued)

Primary Examiner — Sean McGarry
(74) Attorney, Agent, or Firm — Melissa Hunter-Ensor; Leslie Serunian; Greenberg Traurig, LLP

(57) ABSTRACT

An isolated or purified AON for modifying pre-mRNA splicing in the Receptor for Advanced Glycation End-products (RAGE) to modulate splicing of the RAGE gene transcript or part thereof is provided.

27 Claims, 55 Drawing Sheets
Specification includes a Sequence Listing.

(56) References Cited

OTHER PUBLICATIONS

Li et al., "Gene therapy progress and prospects: non-viral gene therapy by systemic delivery," (2006) Gene Ther., 13 (18):1313-9.
Mann CJ et al., "Antisense-induced exon skipping and synthesis of dystrophin in the mdx mouse," (2001) Proc, Natl. Acad. Science, 98(1) 42-47.
Mann et al., "Improved antisense oligonucleotide induced exon skipping in the mdx mouse model of muscular dystrophy," (2002) J Gen Med 4, 644-654.
Mannino, et al., "Liposome Mediated Gene Transfer," (1988) Biotechniques, 6(7):682-690.
Miyada C. G. and Wallace R. B., "Oligonucleotide Hybridization Techniques," (1987) Methods Enzymol. vol. 154 pp. 94-107.
Mueller et al., "Gene Therapy for Cystic Fibrosis," (2008) Clin Rev Allergy Immunol; 35(3):164-78.
Nabel, et al., "Site-Specific Gene Expression in Vivo by Direct Gene Transfer into the Arterial Wall," (1990) Science, 249:1285-1288.
Pickering et al., "Transactivation of RAGE mediates angiotensin-induced inflammation and atherogenesis," (2019) J Clin Invest; 129: 406-421.
Rosenberg, "Immunotherapy and Gene Therapy of Cancer," (1991) Cancer Research 51(18), suppl.: 5074S-5079S.
Rosenfeld, et al., "Adenovirus-Mediated Transfer of a Recombinant α1-Antitrypsin Gene to the Lung Epithefium in Vivo," (1991) Science, 252:431-434.
Rosenfeld, et al., "In Vivo Transfer of the Human Cystic Fibrosis Transmembrane Conductance Regulator Gene to the Airway Epithelium," (1992) Cell, 68:143-155.
Simoes et al., "Cationic liposomes for gene delivery," (2005) Expert Opin Drug Deliv; 2(2):237-54.
Summerton and Weller, "Morpholino Antisense Oligomers: Design, Preparation, and Properties," (1997) Antisense Nucleic Acid Drug Development, 7, 187-197.
Wang and Huang, "pH-sensitive immunoliposomes mediate target-cell-specific delivery and controlled expression of a foreign gene in mouse," (1987) Proc. Natl. Acad. Sci. (USA), 84:7851-7855.
Wolff et al., "Direct Gene Transfer into Mouse Muscle in Vivo," (1990) Science, 247:1465-1468.
Wu and Wu, "Receptor-mediated Gene Delivery and Expression in Viuo," (1988) J. Biol. Chem., 263:14621-14624.
International Search Report and Written Opinion in International Application No. PCT/AU2020/050449, dated May 28, 2020 (13 pages).
Canonico AE et al., "Expression of a CMV Promoter Driven Human a-1 Antitrypsin Gene in Cultured Lung Endothelial Cells and in the Lungs of Rabbits," (1991) Clin Res 39:219 (abstract).
Devereux et al., "A comprehensive set of sequence analysis programs for the VAX," Nucleic Acids Research, 1984, vol. 12, No. 1, pp. 387-395.
Ohe et al., "Regulation of alternative splicing of the receptor for advanced glycation endproducts (RAGE) through G-rich cis-elements and heterogenous nuclear ribonucleoprotein H," The Journal of Biochemistry, 2010, vol. 147, No. 5, pp. 651-659.
Sohail et al., "Evolutionarily emerged G tracts between the polypyrimidine tract and 3' AG are splicing silencers enriched in genes involved in cancer," BMC Genomics, 2014, vol. 15, Article No. 1143, pp. 1-11.

* cited by examiner

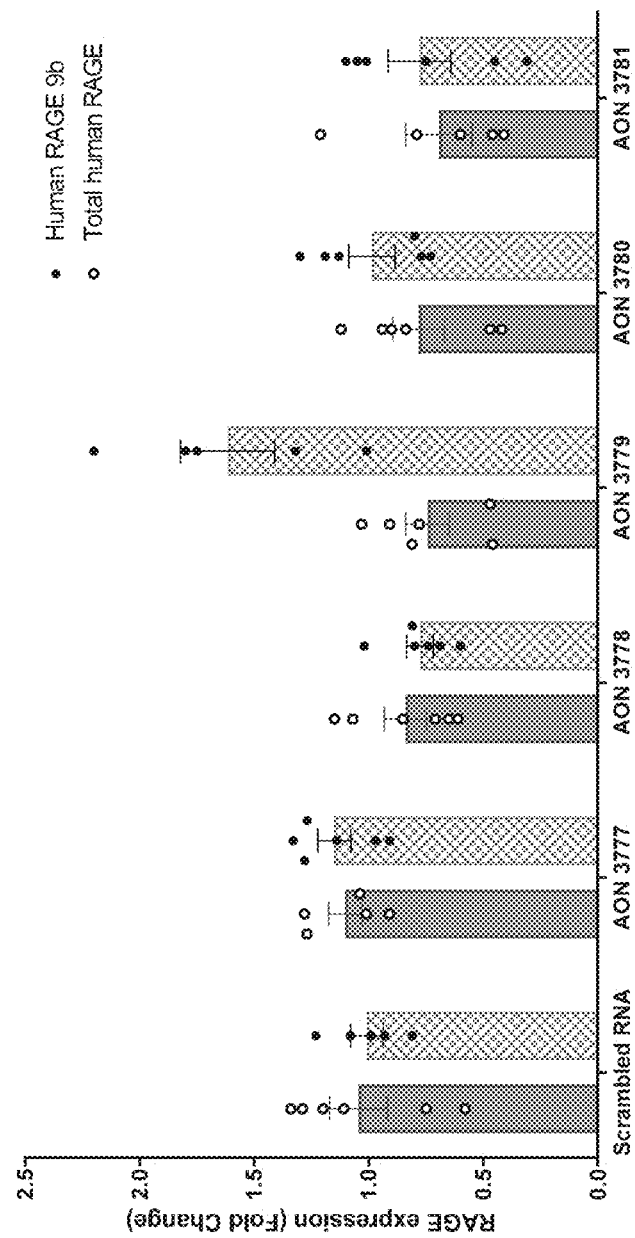

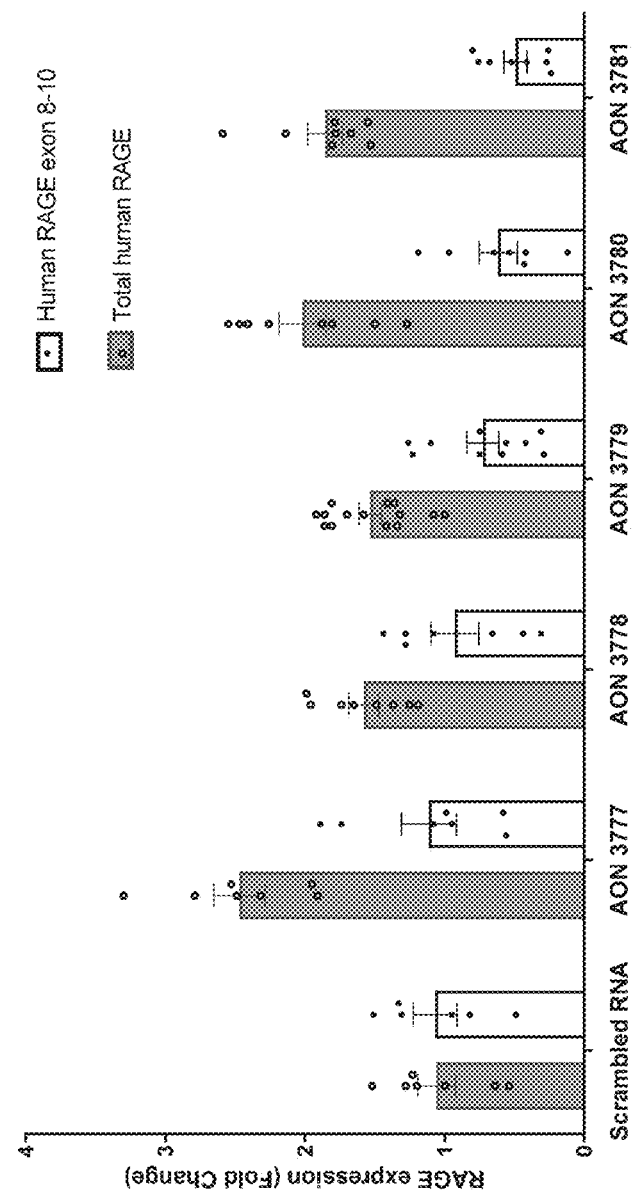

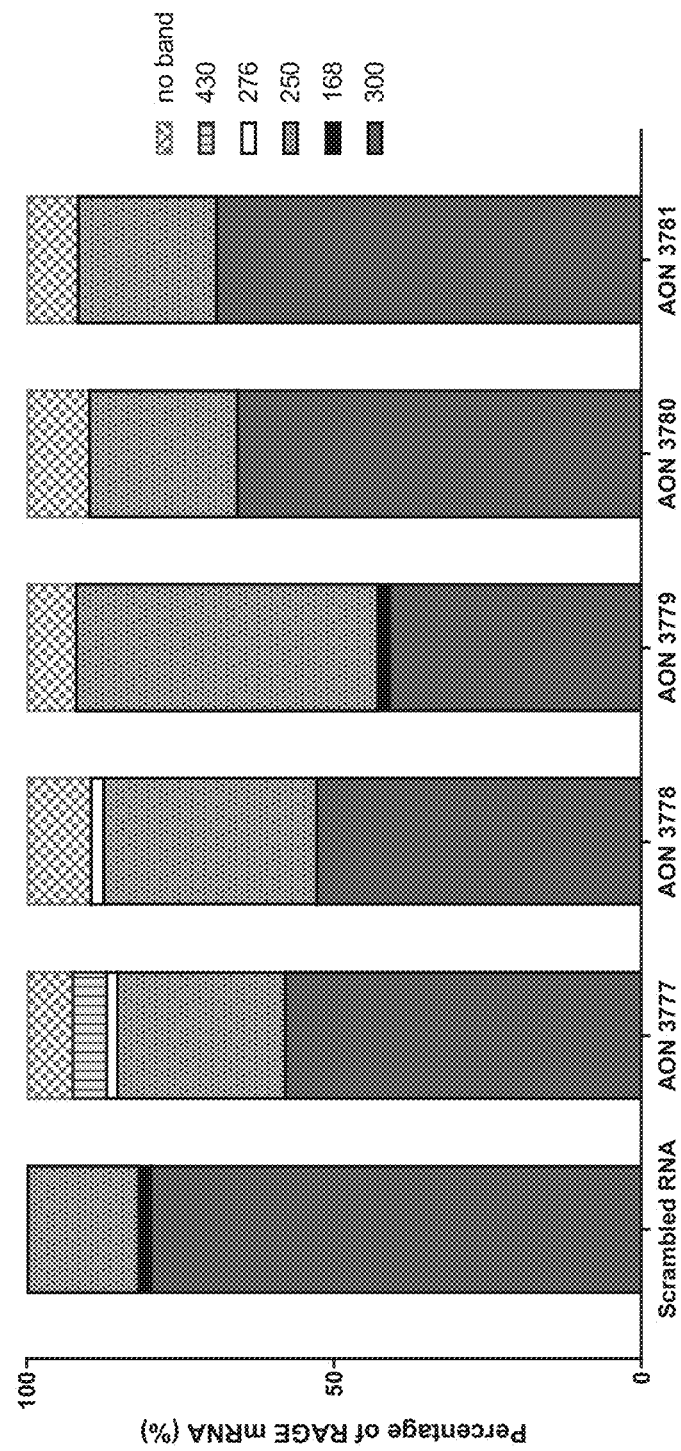

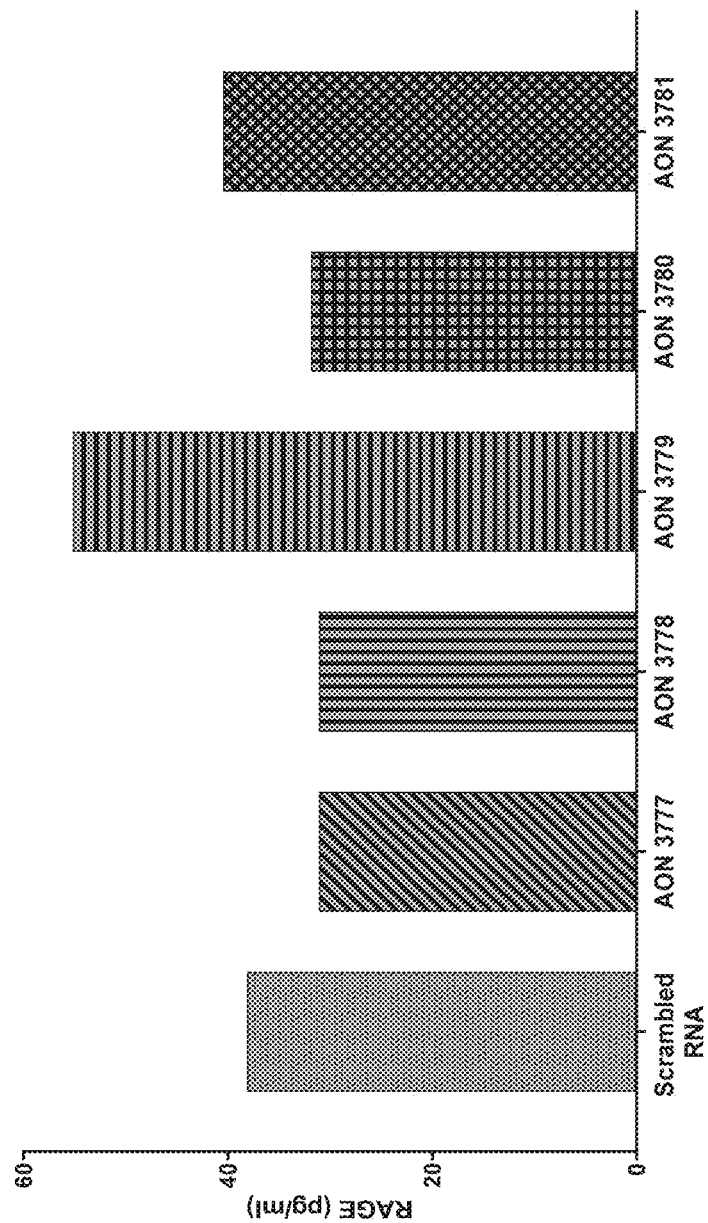

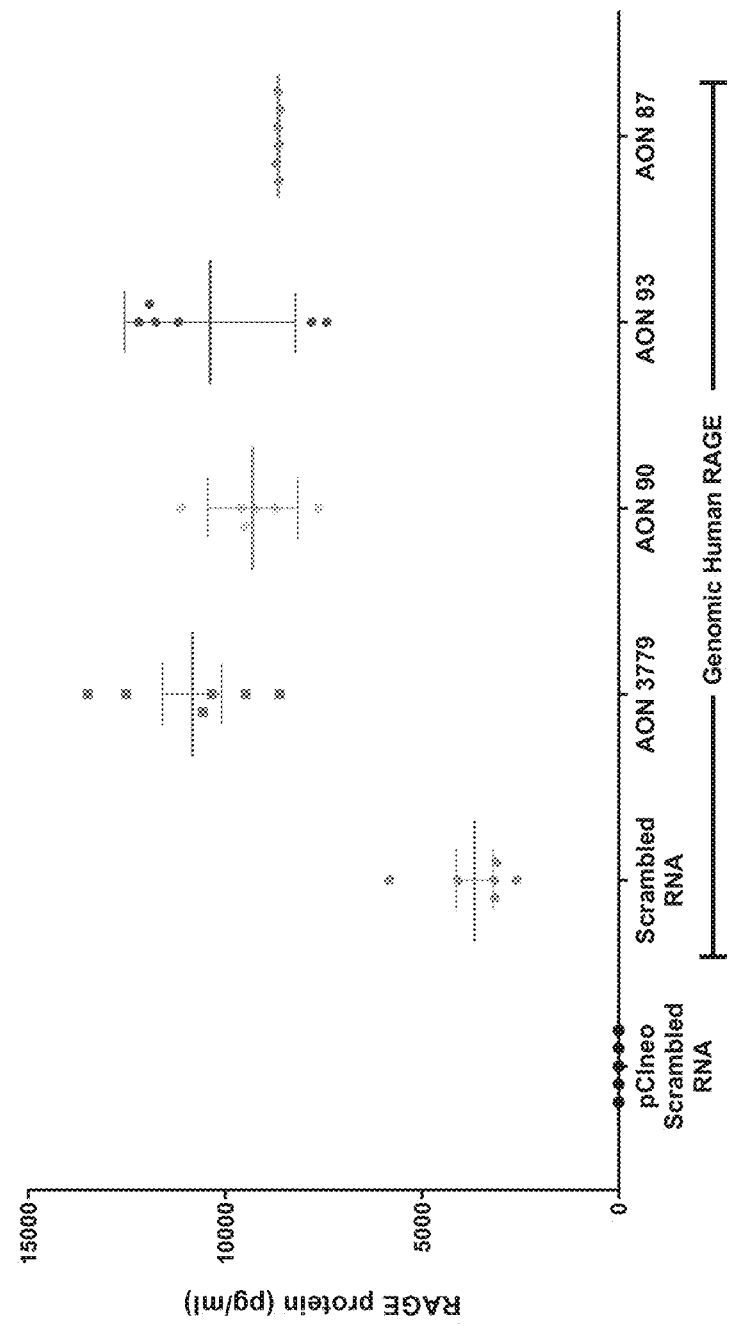

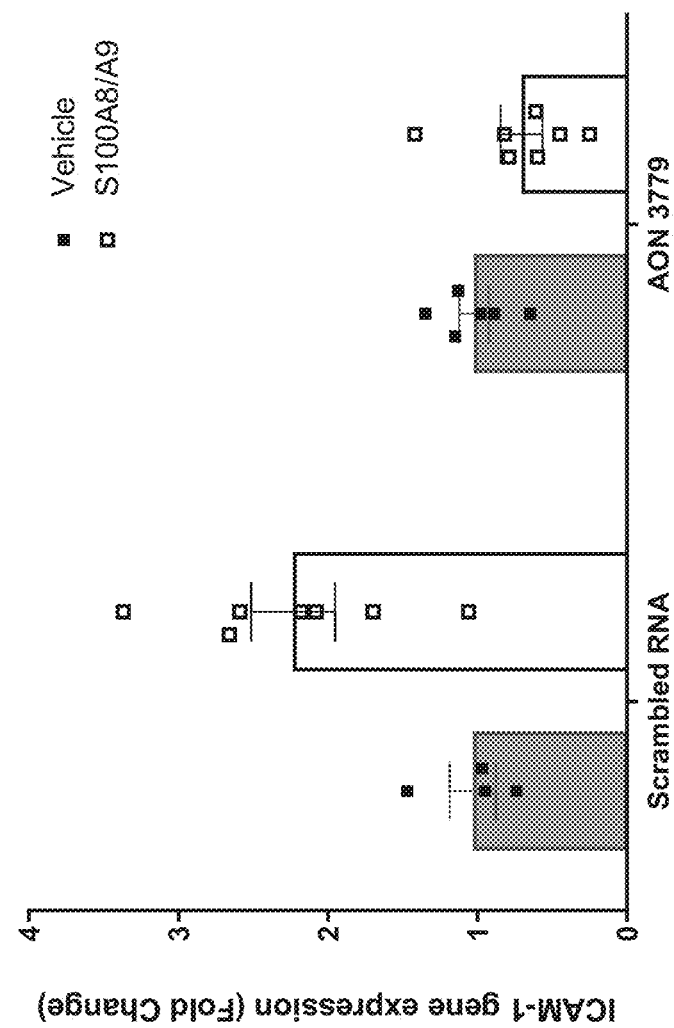

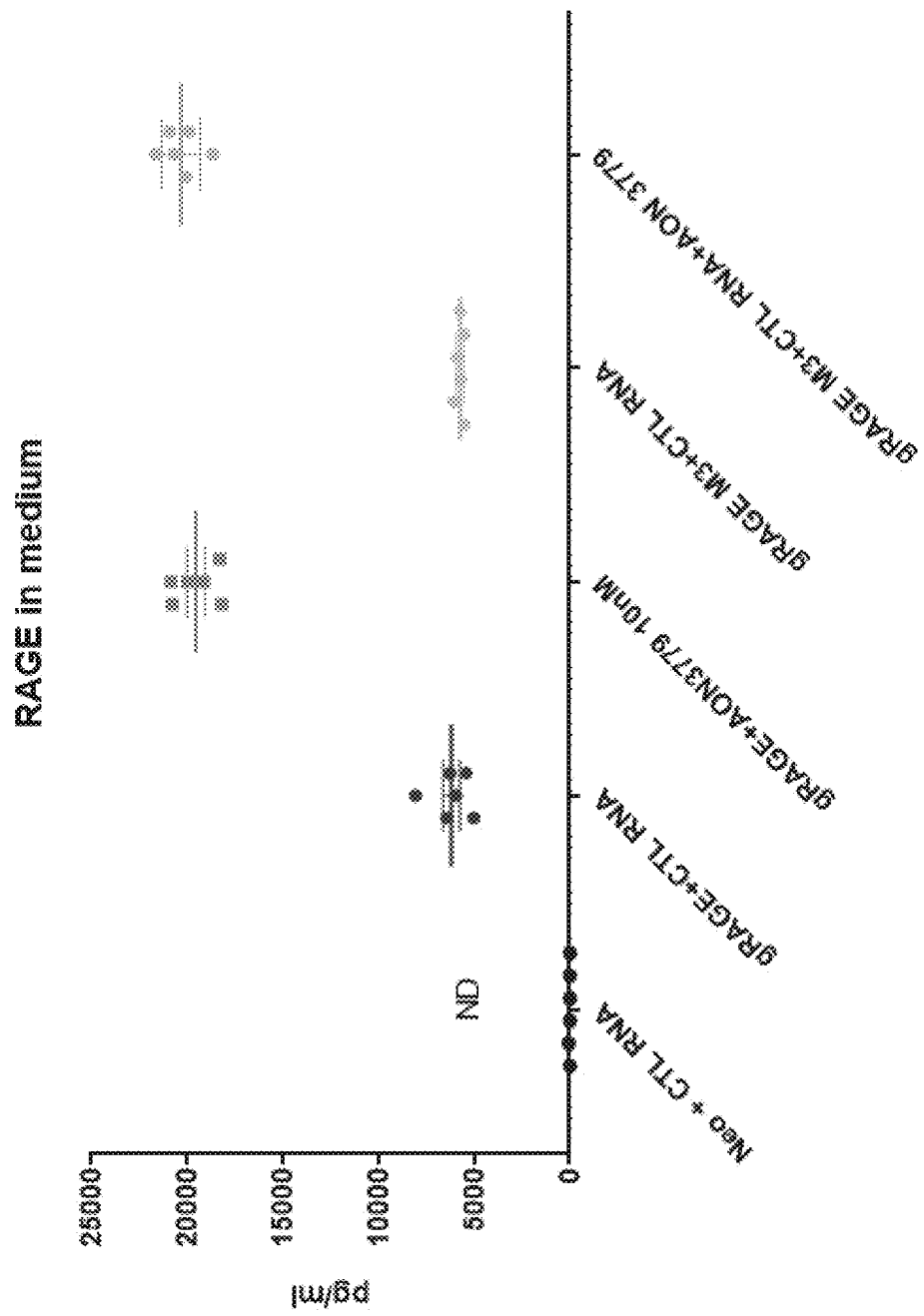

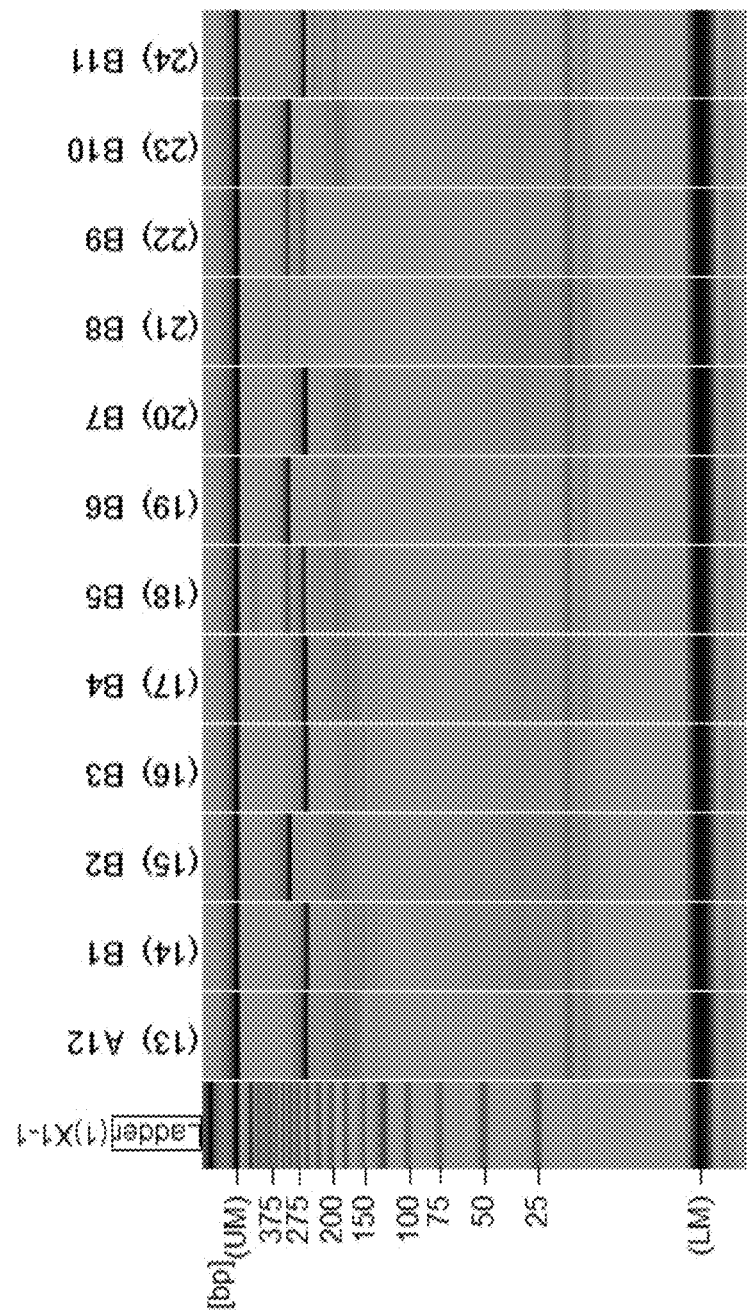

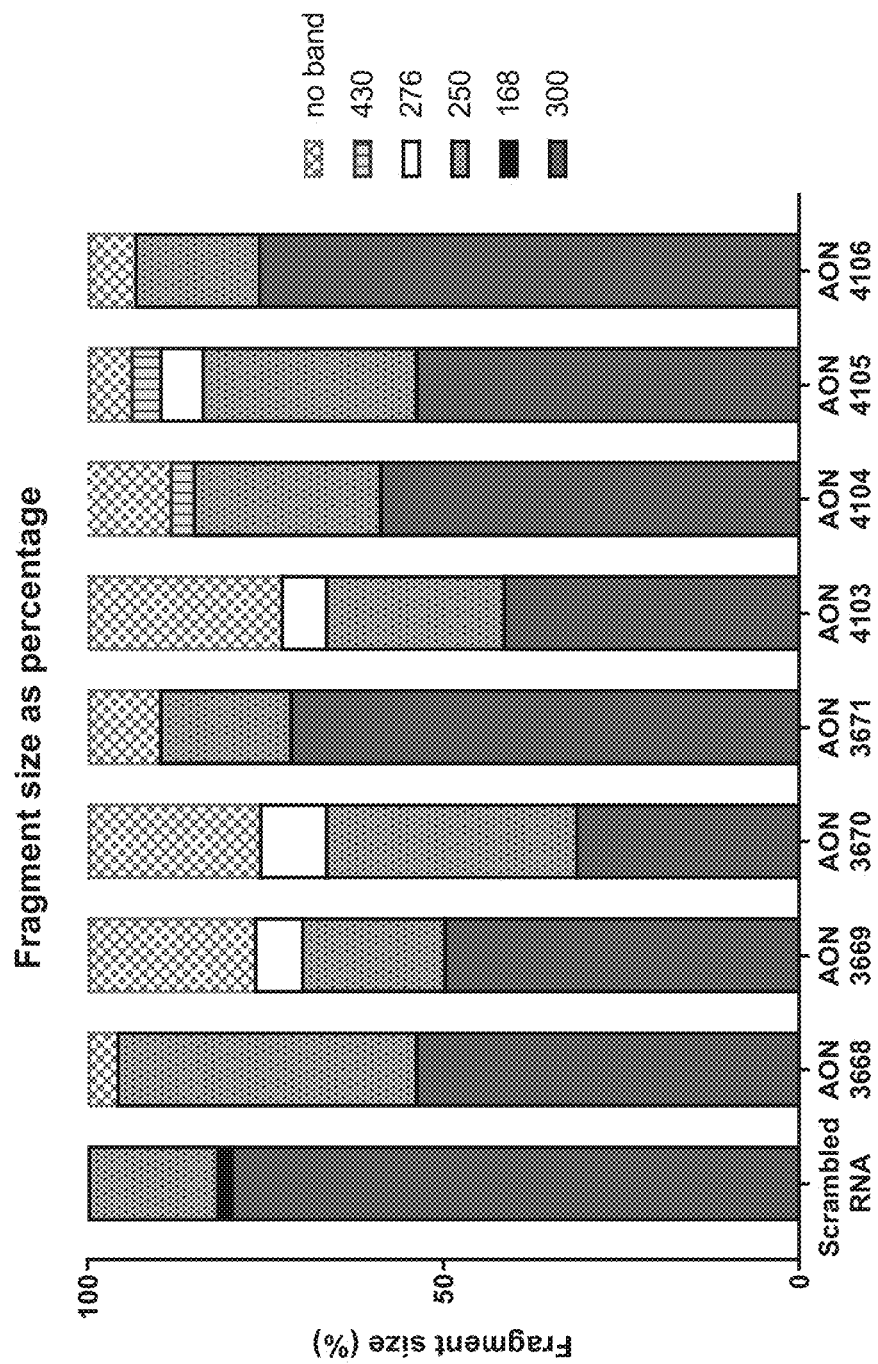

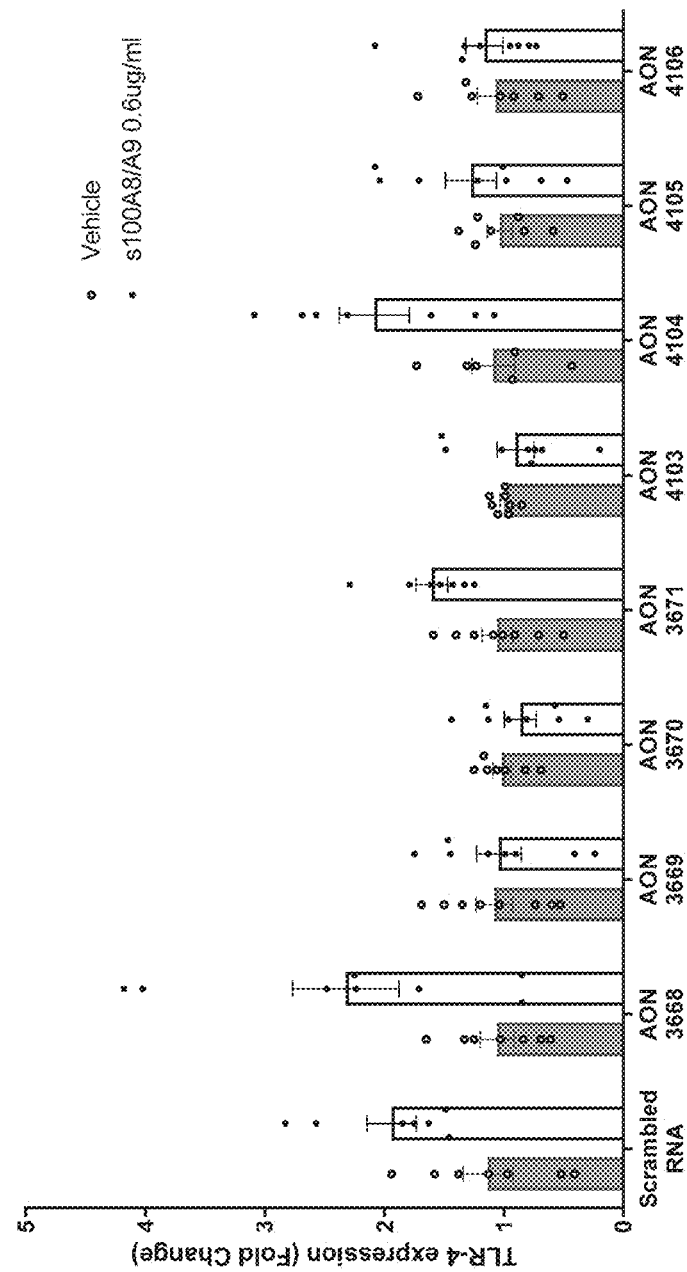

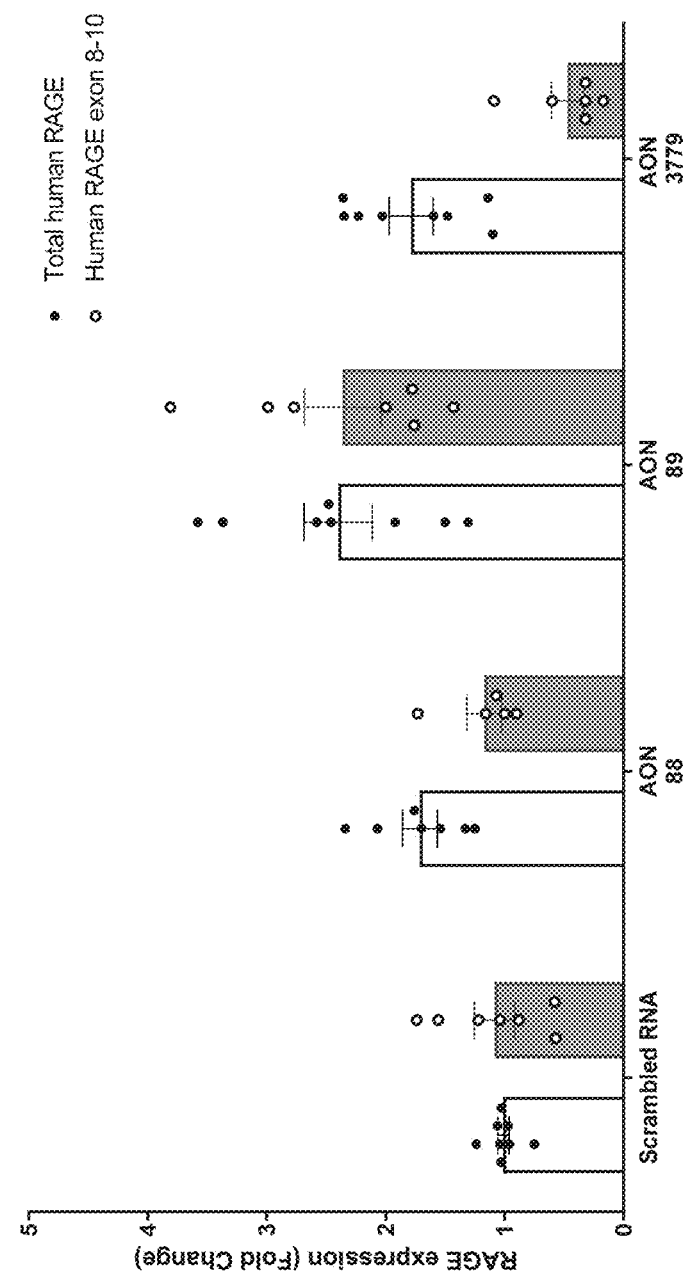

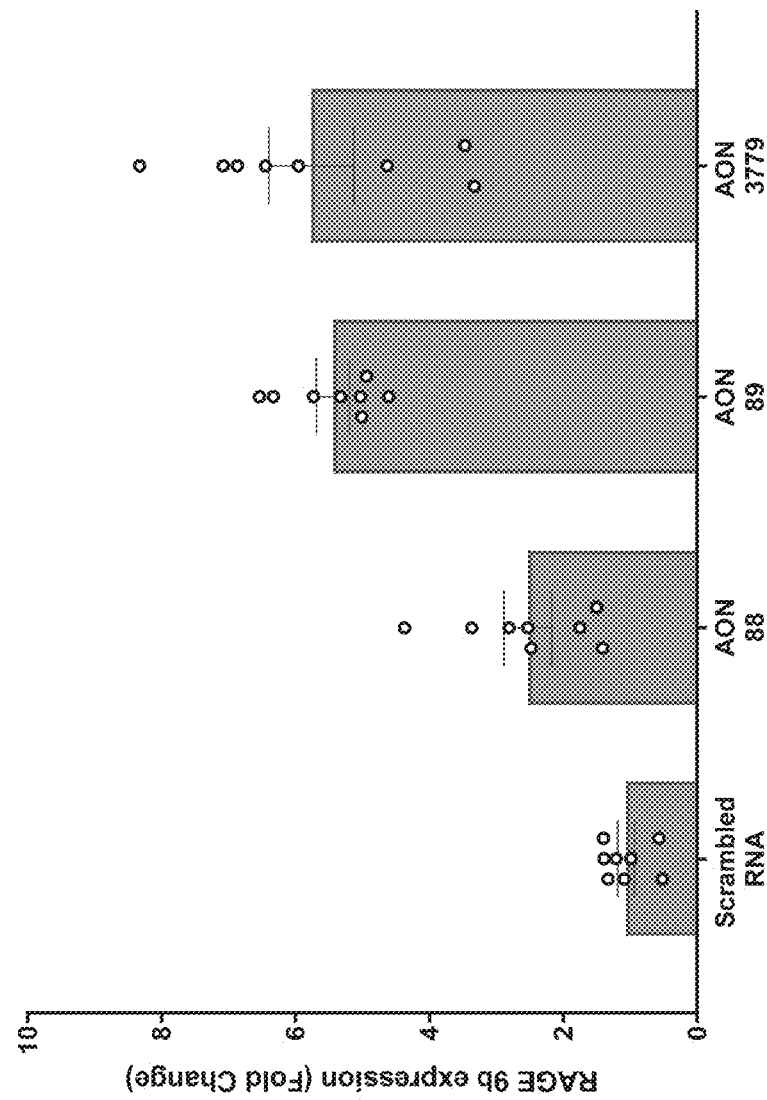

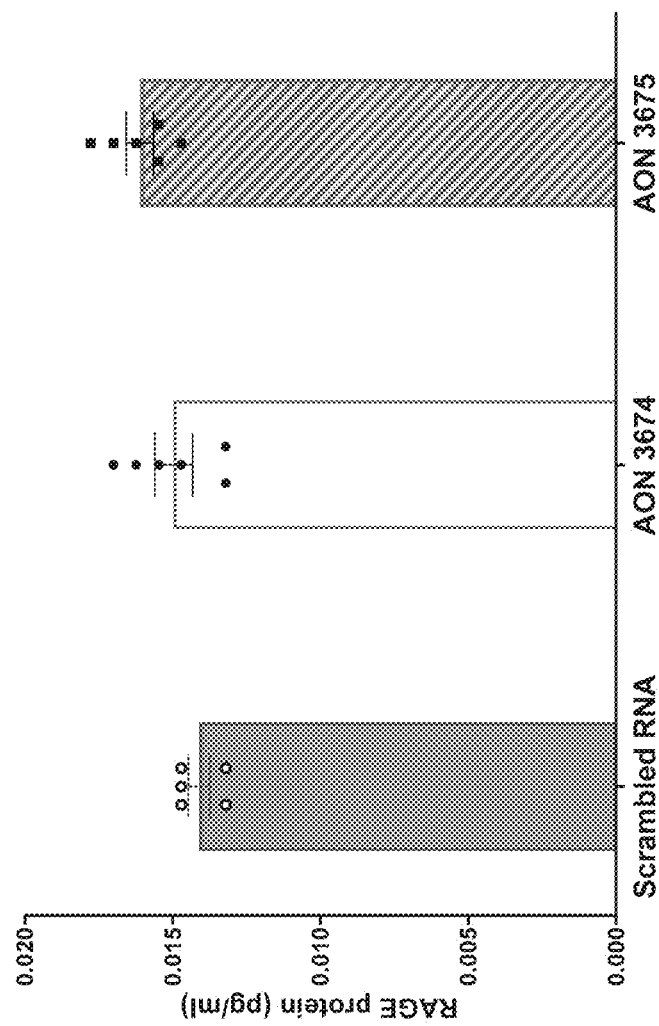

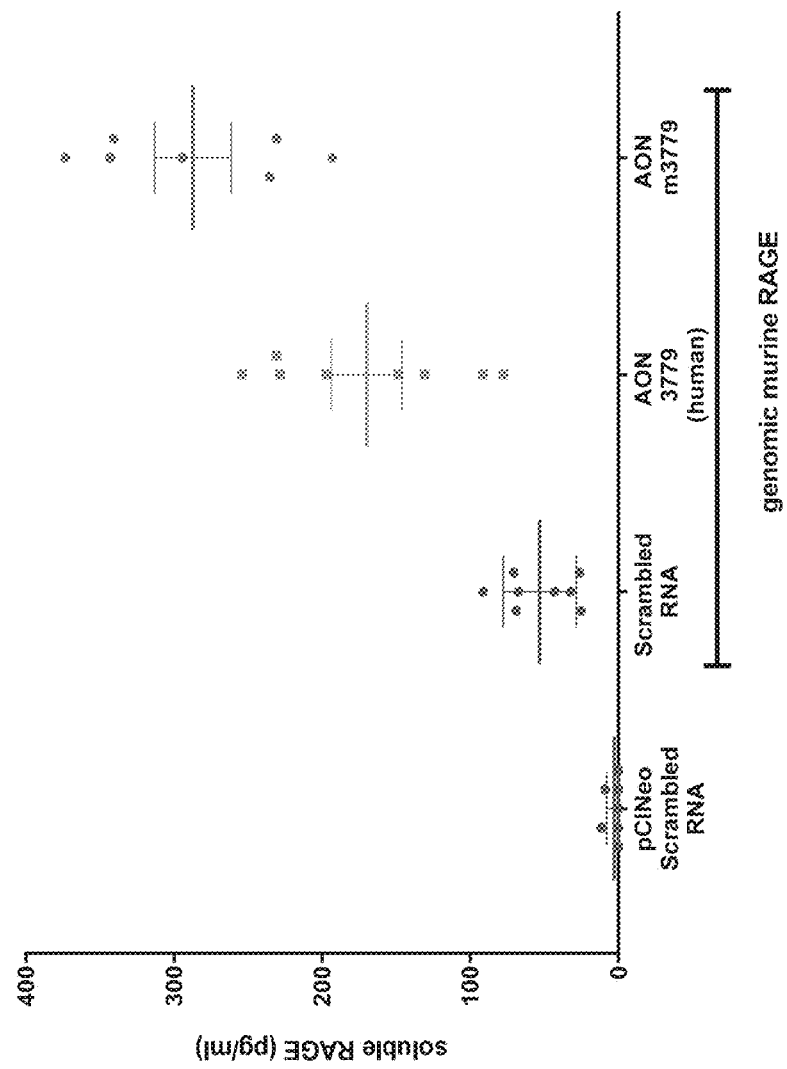

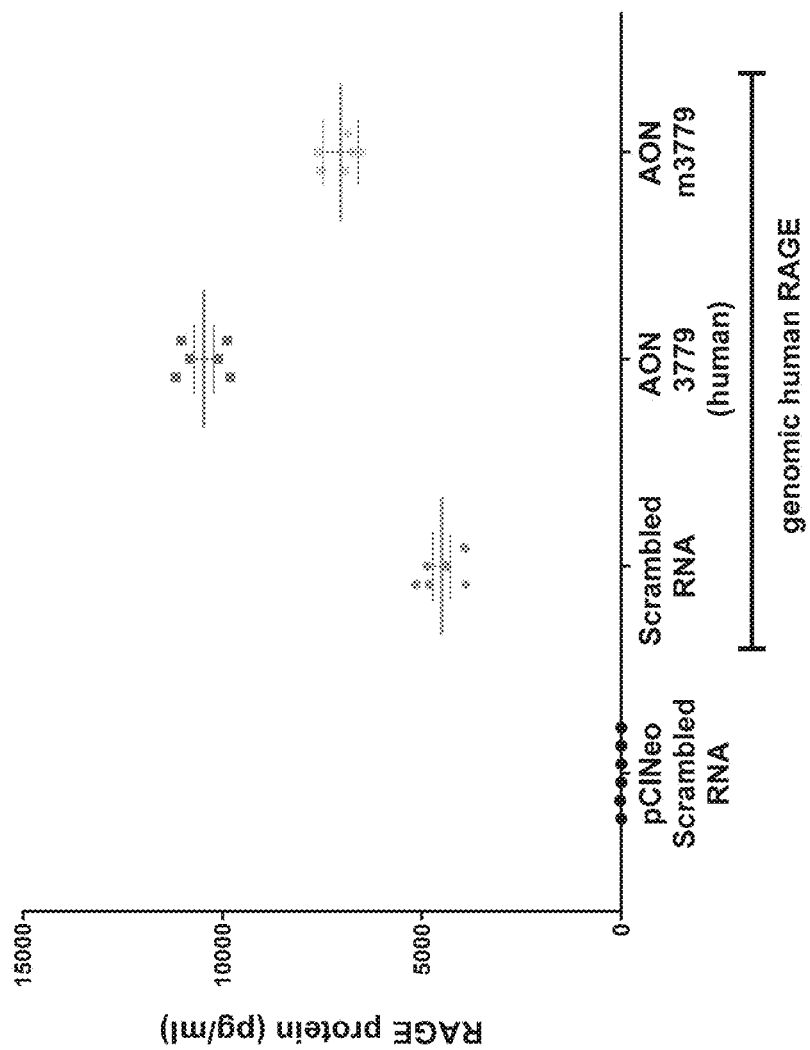

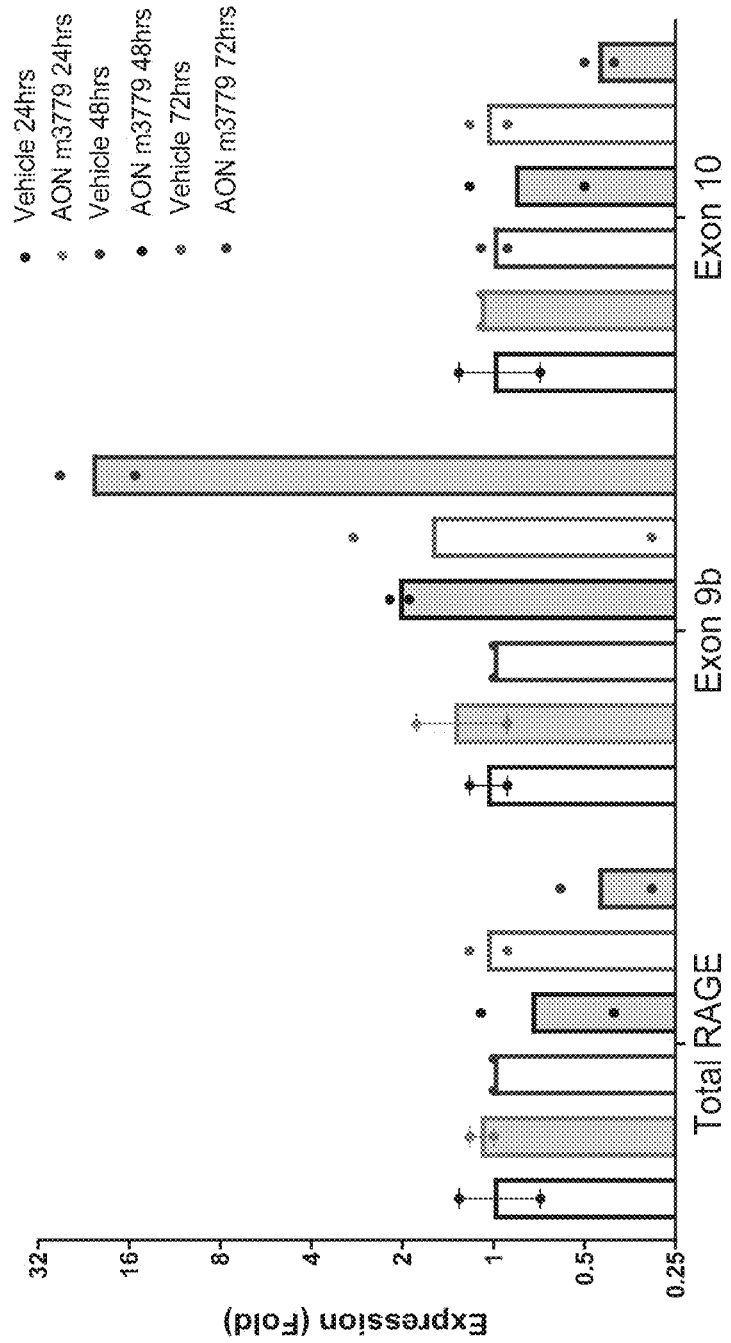

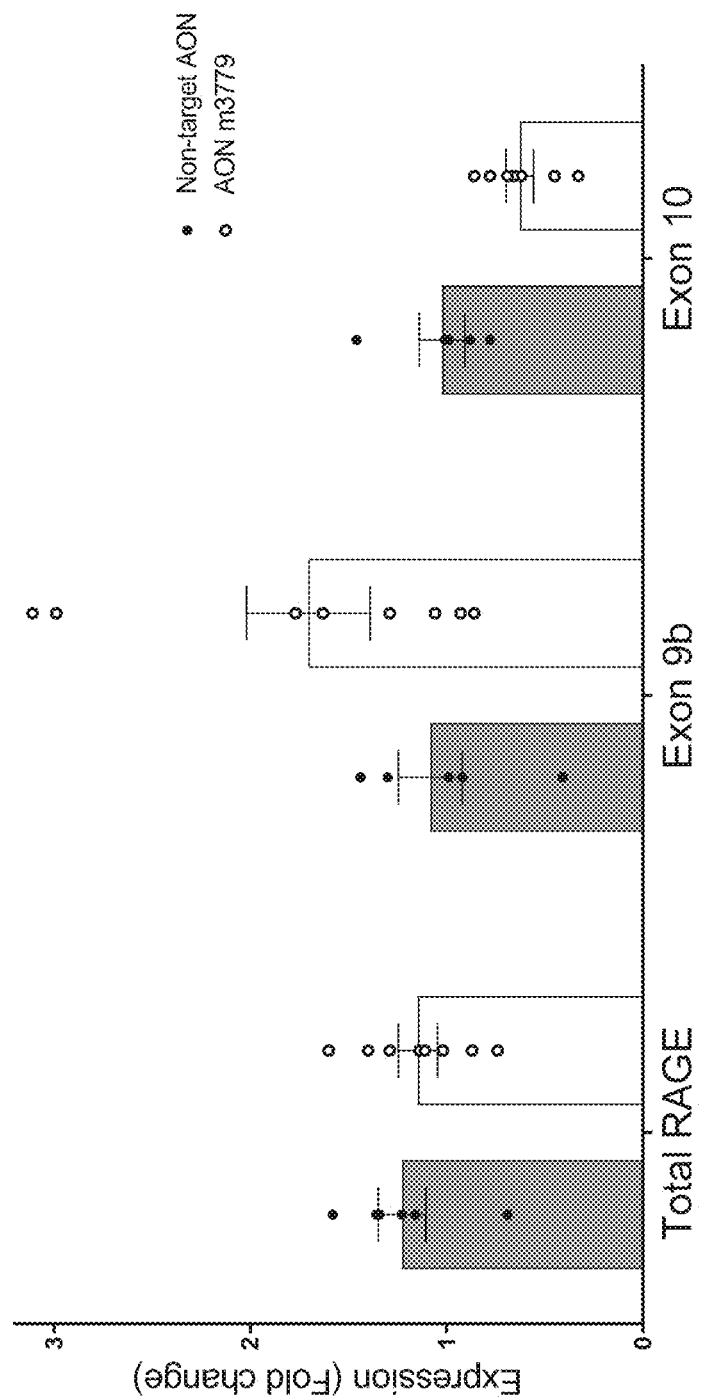

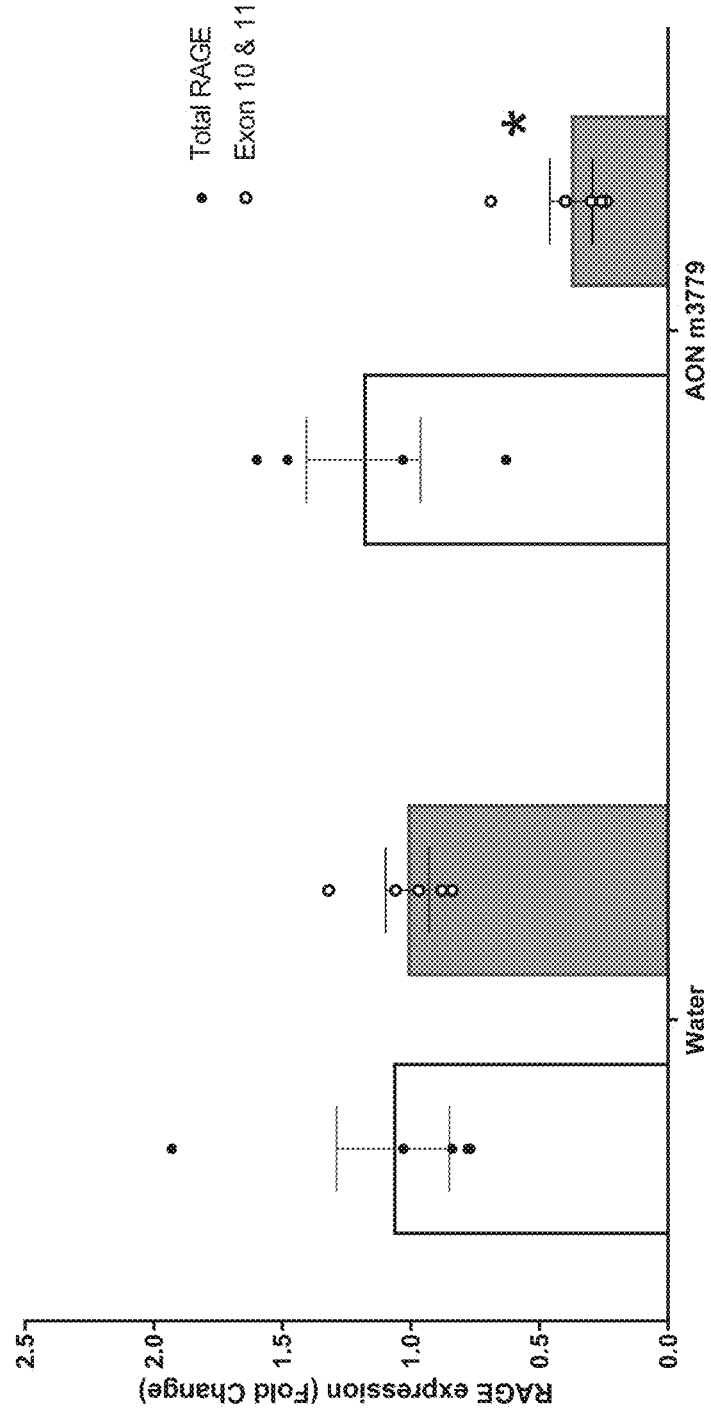

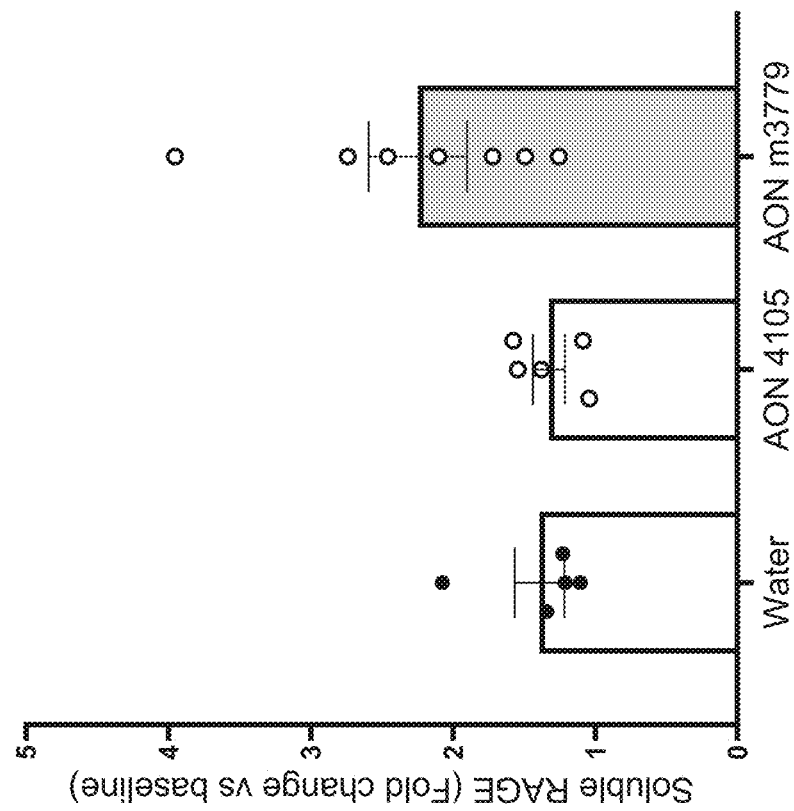

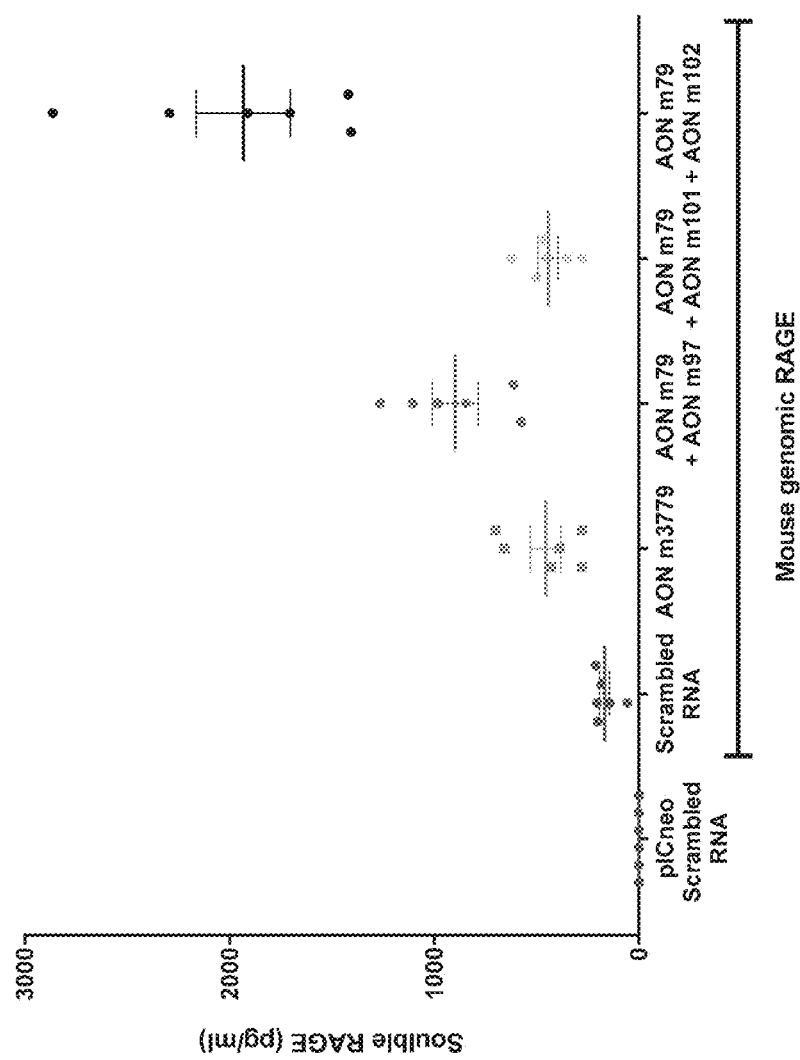

MODULATORS AND MODULATION OF THE RECEPTOR FOR ADVANCED GLYCATION END-PRODUCTS RNA

CROSS-REFERENCE TO RELATED APPLICATIONS

This application is a U.S. National Stage filed under 35 U.S.C. § 111(a), which is a continuation of and claims priority to International PCT Application No. PCT/AU2020/050449, filed May 7, 2020, which claims priority to and benefit of application numbers AU2019901641, filed May 14, 2019, AU2019902095, filed Jun. 17, 2019, AU2019902772, filed Aug. 2, 2019, and AU2019903900, filed Oct. 16, 2019, the contents of all of which are incorporated by reference in their entireties herein.

SEQUENCE LISTING

The instant application contains a Sequence Listing which has been submitted electronically in ASCII format and is hereby incorporated by reference in its entirety. Said ASCII copy, created on Aug. 6, 2021, is named 201418-010201US_SL .txt and is 17,913 bytes in size.

FIELD OF THE INVENTION

The present invention relates to a method for the modulation of alternative splicing of pre-mRNA coding for the Receptor for Advanced Glycation End-products (RAGE) or part thereof, using splice-switching antisense oligonucleotides (AONs) to modify the expression and/or activity of RAGE isoforms, and to methods of treatment of RAGE-related disorders using said modulators.

BACKGROUND ART

The Receptor for Advanced Glycation End-products (RAGE) is a multivalent type I transmembrane glycoprotein belonging to the immunoglobulin (Ig) superfamily. The human RAGE (Ager) gene lies within the major histocompatibility complex class III region on chromosome 6. It comprises 11 exons and 10 introns, and a 5' flanking region that regulates its transcription. The transcribed RAGE mRNA is ~1.4 kb, with a short 3'UTR.

The 50-55 kDa glycosylated RAGE protein is constitutively expressed in a limited range of cells (e.g. vascular endothelium, type I pneumocytes, leukocytes), although RAGE expression may be induced in most cell types and tissues following injury, stress, hypoxia or inflammation, providing a conduit for pro-inflammatory and pro-proliferative signalling. RAGE expression is consequently upregulated in inflammatory and metabolic disorders including but not limited to neurodegenerative disease, cancer, cardiovascular disease, diabetes, autoimmune and ischaemic injury in which RAGE is also implicated in the development and progression.

RAGE has been implicated in a range of brain disorders including Alzheimer's disease; amylotrophic lateral sclerosis; Huntington's disease; Creutzfeld-Jakob's disease; neurodegenerative conditions such as diabetic neuropathy, familial amyloid polyneuropathy, Charcot neuroarthropathy and vasculitic neuropathy; neuropathic pain; glioma development and progression; ischaemic brain injury/stroke, and multiple sclerosis.

RAGE has been implicated in many aspects of tumour biology including growth, migration and invasion of tumour cells. Many cancers express higher levels of RAGE (illustrative examples are breast, colon, kidney and stomach cancer). The exception is lung cancer in which RAGE expression is reduced as RAGE is lost as lung cells differentiate and become more malignant.

In C6 glioma cells, tumour volume is markedly diminished in tumours comprised of cells in which RAGE was blocked. In contrast, tumours overexpressing wild-type RAGE grew rapidly and invaded the surrounding tissue very efficiently. It would be desirable to have therapeutics to block RAGE signalling as a cancer treatment for many common cancers such as: glioma/medulloblastoma multiforme; pancreatic cancer; melanoma; prostate cancer; breast cancer; liver cancer/hepatoma; and colon cancer.

Under healthy conditions, the lungs' expression of RAGE is the highest of all tissues. However, RAGE expression in the lung is normally only seen in type I pneumocytes. Upregulation of RAGE signalling in the lung in other cells and at other sites has been implicated in a range of lung disorders including: chronic obstructive pulmonary disease (COPD)/emphysema; asthma; injury due to cigarette smoking/pollution; acute lung injury/Acute Respiratory Distress Syndrome; and pulmonary fibrosis.

RAGE is also critically involved in a number of inflammatory conditions such as inflammatory arthritis; osteoarthritis; retinal disease; atherosclerosis; vascular calcification; ischaemic cardiac disease/cardiac remodelling/fibrosis; heart failure; diabetic and non-diabetic kidney disease; inflammatory bowel disease; pre-eclampsia; polycystic ovarian syndrome; hepatic steatosis, fibrosis, ischemic and non-ischemic liver injury; muscular dystrophy; spinal cord injury; skin inflammation and ageing; and keratitis.

Human RAGE is composed of an immunoglobulin-like ecto-domain, a single transmembrane domain and a short (42 amino acid) cytosolic tail. The ecto-domain (also known as the extracellular domain) of RAGE includes three immunoglobulin-like regions: an N-terminal V-type domain followed by two C-type domains (termed C and C' or alternatively C1 and C2).

Binding of Advanced Glycation End-products (AGEs) and non-AGE ligands to the ecto-domain of RAGE activates intracellular signal transduction cascades implicated in inflammation, injury and cell proliferation and differentiation. RAGE activation also triggers a positive feedback loop in which RAGE ligand-receptor interaction increases expression of RAGE via NFκB activation, thereby augmenting subsequent RAGE-induced cellular activation. In fact, the only means the inventors know to strongly downregulate RAGE expression is to reduce activation of RAGE. This situation contrasts with other receptors, in which increased levels of ligand decrease expression of the receptor.

In humans, the cytosolic tail of RAGE is 43 amino acids long (residue 362 to residue 404). This cytosolic tail contains motifs which are critical for RAGE-dependent cellular activation but not ligand binding. The cytosolic tail of RAGE may be trans-activated following activation of co-located G-protein coupled receptors by their cognate ligands without the binding of AGEs of non-AGE ligands to the RAGE ecto-domain (also known as ligand-independent activation of RAGE) leading to activation of the same pathways (Pickering et al. J Clin Invest 2019; 129: 406-421). RAGE ligand-independent activation of the RAGE cytosolic tail by certain co-located activated G-protein coupled receptors appears to be an important pathway by which RAGE is activated in vivo.

In both ligand-dependent activation of RAGE and ligand-independent activation of RAGE, intracellular signalling is mediated by the cytosolic domain of RAGE, which interacts with a range of signalling partners.

The alternative splicing of RAGE is also important for the regulation of RAGE activity, through the generation of RAGE isoforms that have an altered ability to be activated by ligand-dependent and ligand-independent signalling pathways. The alternative splicing of RAGE is altered in disease states including malignancy, diabetes and Alzheimer's disease. But while alternative splicing appears to be important for RAGE regulation/dysregulation, there has been no way to specifically target this mechanism.

It is against this background that the present method of using splice switching AONs for the modulation of RAGE splicing towards the preferred generation of cyto-protective RAGE isoforms over full length RAGE is described.

The above discussion of the background art is intended to facilitate an understanding of the present invention only. The discussion is not an acknowledgement or admission that any of the material referred to is or was part of the common general knowledge as at the priority date of the application.

SUMMARY OF INVENTION

Broadly, according to one form of the invention, there is provided an isolated or purified AON that is used to modulate alternative splicing of pre-mRNA gene transcript coding for the Receptor for Advanced Glycation End-products (RAGE) or part thereof.

In one aspect of the invention, there is provided an AON of 10 to 50 nucleotides comprising a targeting sequence complementary to a region near or within an intron of the RAGE pre-mRNA.

In one aspect of the invention, there is provided an AON of 10 to 50 nucleotides comprising a targeting sequence complementary or adjacent to a splice site of the RAGE pre-mRNA.

Because factors such as RNA secondary structure, competition between AONs and SR proteins, heterogeneous nuclear ribonucleoproteins (hnRNPs), and/or other elements that make up the spliceosome can affect AON's' action, AONs directed at the crucial acceptor or donor splice sites will not always alter splicing. Consequently, in one aspect of the invention, there is provided an AON of 10 to 50 nucleotides comprising a targeting sequence complementary or adjacent to cis-acting RNA elements in the pre-mRNA of RAGE that act as enhancers or silencers, that, when bound by an elements of the splicosome (e.g. protein-splicing factors, uRNA, lncRNA) modulates the splicing of a nearby exon.

In one aspect of the invention, there is provided an AON of 10 to 50 nucleotides comprising a targeting sequence complementary to RAGE pre-mRNA which modulates secondary structure of said mRNA to influence splice site selection.

In one form of the invention, there is provided an isolated or purified AON for inducing exclusion (also known as skipping) of one or more exonic sequences in the RAGE gene transcript or part thereof.

In one form of the invention, there is provided an isolated or purified AON for inducing retention of intronic sequences in the RAGE gene transcript or part thereof.

In one form of the invention, the AON is chemically-modified to prevent degradation of the pre-mRNA-AON complex, including but not limited to phosphorodiamidate morpholino oligomers (PMO), 2' O-methyl phosphorothioate oligonucleotides (2OMe), and 2'-O-methoxyethyl phosphorothioate oligonucleotides (2OMe), locked nucleic acid (LNA) modified AONs, thermostable twisted intercalating nucleic acid (TINA) and peptide nucleic acids (PNAs).

In one form of the invention, AONs are conjugated to moieties to increase their delivery, including but not limited to cell-penetrating peptides (CPPs), vivo-morpholinos (VMO) or peptide phosphorodiamidate morpholino oligomers (PPMO).

Preferably, the AON is selected from the group comprising the sequences set forth in any of Tables 3a-3d. Preferably, the AON is selected from the list comprising: SEQ ID NO: 1-31. More preferably, the AON is SEQ ID NO: 11, 18, 19, or 20.

The AON of the invention may be selected to be an AON capable of binding to a selected target site, wherein the target site is a putative mRNA splicing site selected from a splice donor site, splice acceptor sites, splice enhancer sequences splice silencer sequences or sites that modulate the secondary structure of pre-mRNA. The target site may also include some flanking intronic sequences when the donor or acceptor splice sites are targeted.

More specifically, the AON may be selected from the group comprising of any one or more of SEQ ID NOs: 1-31 and/or the sequences set forth in any of Tables 3a-3d, and combinations or cocktails thereof. More preferably, the AON is SEQ ID NO: 11, 18, 19, or 20. The combination of AONs is preferably a combination of SEQ ID NO: 11 and 10, or SEQ ID NO: 11 and 13. This includes sequences which can hybridise to such sequences under stringent hybridisation conditions, sequences complementary thereto, sequences containing modified bases, modified backbones, and functional truncations or extensions thereof which possess or modulate pre-mRNA processing activity in a RAGE gene transcript.

In certain embodiments, AONs may be 100% complementary to the target sequence, or may include mismatches, e.g., to accommodate variants, as long as a hetero-duplex formed between the oligonucleotide and target sequence is sufficiently stable to withstand the action of cellular nucleases and other modes of degradation which may occur in vivo. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligonucleotide and the target sequence.

The invention extends also to a combination of two or more AONs capable of binding to a selected target to modulate alternative splicing of the RAGE pre-mRNA, including a construct comprising two or more such AONs. The constructs may be used together for a combined AON-based therapy. The combination of AONs is preferably a combination of SEQ ID NO: 11 and 10, or SEQ ID NO: 11 and 13.

The invention extends, according to a still further aspect thereof, to cDNA or cloned copies of the AON sequences of the invention, as well as to vectors containing the AON sequences of the invention. The invention extends further also to cells containing such sequences and/or vectors.

There is also provided a method for manipulating splicing of a RAGE gene transcript, the method including the step of:
a) providing one or more of the AONs as described herein and allowing the oligomer(s) to bind to a target nucleic acid site.

There is also provided a pharmaceutical, prophylactic, or therapeutic composition to treat, prevent or ameliorate the effects of a disease related to RAGE expression in a patient, the composition comprising:
  a) one or more AONs as described herein; and
  b) one or more pharmaceutically acceptable carriers and/or diluents.

The composition may comprise about 1 nM to 1000 nM of each of the desired AON(s) of the invention. Preferably, the composition may comprise about 10 nM to 500 nM, most preferably between 1 nM and 10 nM of each of the AON(s) of the invention.

There is also provided a method to treat, prevent or ameliorate the effects of a disease associated with RAGE expression, comprising the step of:
  a) administering to the patient an effective amount of one or more AONs or pharmaceutical composition comprising one or more AONs as described herein.

There is also provided the use of purified and isolated AONs as described herein, for the manufacture of a medicament to treat, prevent or ameliorate the effects of a disease associated with RAGE expression and/or activity.

There is also provided a kit to treat, prevent or ameliorate the effects of a disease associated with RAGE expression in a patient, which kit comprises at least an AON as described herein and combinations or cocktails thereof, packaged in a suitable container, together with instructions for its use.

Preferably the disease associated with RAGE expression in a patient is neurodegenerative disease, cancer, lung disorder, or an inflammatory disease.

The subject with the disease associated with RAGE expression may be a mammal, including a human.

Further aspects of the invention will now be described with reference to the accompanying non-limiting examples and drawings.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which:

FIG. 1b shows the fold change in the expression of any RAGE mRNA (total human RAGE) splicoforms and RAGE mRNA splicoforms containing the human RAGE 9b sequence in A579 cells, as detected by real time RT-PCR, following treatment with selected AONs targeting exon 10 or a control (scrambled RNA treated) cells.

FIG. 1c shows the fold change in mRNA expression of any RAGE mRNA (total human RAGE) splicoforms and human RAGE mRNA splicoforms containing exon 10, as detected by real time RT-PCR following treatment of A579 cells with selected AONs targeting exon 10 or control (scrambled RNA treated) cells.

FIG. 1e shows the percentage of RAGE clones encoding constructs containing exon 8-11 fragments of different sizes, denoting the relative expression of different RAGE mRNA splicoforms following treatment of A579 cells with specific AONs targeting exon 10 or control (scrambled RNA treated) cells. For example, the 300 band denotes a splicoform containing exon 8, 9, 10 and 11 (i.e. a signalling capable splicoforms), while the 250 band denotes a splicoform containing RAGE 9b and no band denotes a RAGE mRNA splicoform associated with the loss of exon 8.

FIG. 1h shows the concentration of endogenous soluble RAGE protein detected in the cell media following treatment of A579 cells with selected AONs targeting exon 10 compared to control (scrambled RNA treated) cells.

FIG. 1k shows the expression of soluble RAGE protein in the media following transfection of CHO cells with DNA coding for the genomic sequence of human RAGE (gRAGE), with and without selected AONs targeting exon 10 adjacent to or overlapping the site also targeted by AON 3779, as measured by ELISA.

FIG. 1m shows the induction of ICAM-1 gene expression following treatment of A549 cells with the RAGE ligand, S100A8/9 (0.6 µg/ml) and its modulation by pre-transfection with selected AONs targeting exon 10 compared to control (scrambled RNA treated) cells.

FIG. 1o shows the induction of ICAM-1 gene expression following treatment of A549 cells with Ang II, which is capable of inducing transactivation of RAGE. Notably this induction in ICAM-1 gene expression is also modulated by pre-transfection of A579 cells with selected AONs targeting exon 10 compared to control (scrambled RNA treated) cells.

FIG. 1v discloses SEQ ID NOS 65-68, 75, and 69-72, respectively, in order of appearance.

FIG. 1w shows the lack of effect following mutation of the putative polyG target of hnRNP on the alternative splicing of human RAGE expressed (mutant gRAGE M3) on the observed increase in soluble RAGE in response to transfection with AON 3779

FIG. 2a discloses SEQ ID NO: 73.

FIG. 2c is a representative gel image of DNA PCR products spanning exon 8-11 with bands of different sizes or no bands denoting the presence of different splicoforms.

FIG. 2d represents the percentage of RAGE mRNA clones encoding constructs containing exon 8-11 fragments of different sizes, denoting the relative expression of different splicoform mRNA following treatment of A579 cells with selected AONs targeting exon 10 or a scrambled RNA control (CTL). For example, the 300 band denotes a RAGE mRNA splicoform containing exon 8, 9, 10 and 11 (i.e. a signalling capable splicoforms), while the 250 band denotes a splicoform containing RAGE 9b and no band denotes a RAGE mRNA splicoform associated with the loss of exon 8.

FIG. 2f shows the induction of TLR-4 gene expression following treatment with the RAGE ligand, S100A8/9 (0.6 µg/mL) and its modulation following transfection with selected AONs targeting exon 9 compared to control (scrambled RNA treated) cells.

FIG. 3a shows the fold change in expression of any RAGE mRNA (total RAGE) splicoforms and human RAGE mRNA splicoforms containing exon 10, as detected by real time RT-PCR following treatment of A579 cells with selected AONs targeting intron 9, AON 3779 (as a positive control) or control (scrambled RNA treated) cells.

FIG. 3d shows fold change in expression of RAGE mRNA splicoforms containing the exon 9b, as detected by real time RT-PCR, following treatment of HMEC1 cells with selected AONs targeting intron 9, AON 3779 (as a positive control), or control (scrambled RNA treated) cells.

FIG. 3f discloses SEQ ID NO: 74.

FIG. 4d shows the concentration of soluble RAGE protein in the media following treatment of PMAEC cells with specific AONs (10 nM) targeting exon 9 of murine RAGE or control (scrambled RNA treated) cells.

FIG. 4f shows the concentration of soluble RAGE protein in the media following treatment of CHO cells expressing genomic murine RAGE, with AON 3779 (10 nM), AON m3779 or control (scrambled RNA treated) cells.

FIG. 4g shows the concentration of soluble RAGE protein in the media following treatment of CHO cells expressing genomic human RAGE, with AON 3779 (10 nM), AON m3779 or control (scrambled RNA treated) cells.

FIG. 4i shows the time-dependent expression of any RAGE mRNA (total RAGE) and RAGE mRNA splicoforms containing exon 9b on real time RT-PCR following treatment of precision cut lung slices from mice with AON m3779 or vehicle (saline).

FIG. 4j shows the fold change in pulmonary expression of any RAGE mRNA (total mouse RAGE) splicoforms and murine RAGE mRNA splicoforms containing exon 9b or exon 10 on real time RT-PCR, one week after daily subcutaneous injection of AON m3779 into C57Bl6 mice, compared to non-target AON control.

FIG. 4l shows the fold change in pulmonary expression of any RAGE mRNA (total mouse RAGE) splicoforms and murine RAGE mRNA splicoforms containing exon 10 and 11 on real time RT-PCR 48 hours after intratracheal instillation of a 2-0'Me formulation of AON m3779 into C57Bl6 mice, compared to vehicle control. * denotes p=0.01 vs baseline.

FIG. 4m shows the fold change (%) in circulating soluble RAGE compared to a baseline bleed two-days after intratracheal injection of AON m3779, AON4105 and sterile water control into C57Bl6 mice.

FIG. 5e shows the expression of soluble RAGE protein in the media following transfection of CHO cells with DNA coding for the murine genomic sequence of mouse RAGE, with and without combinations of selected AONs or control (scrambled RNA), as measured by ELISA.

DESCRIPTION OF INVENTION

Detailed Description of the Invention

Figure 1A:
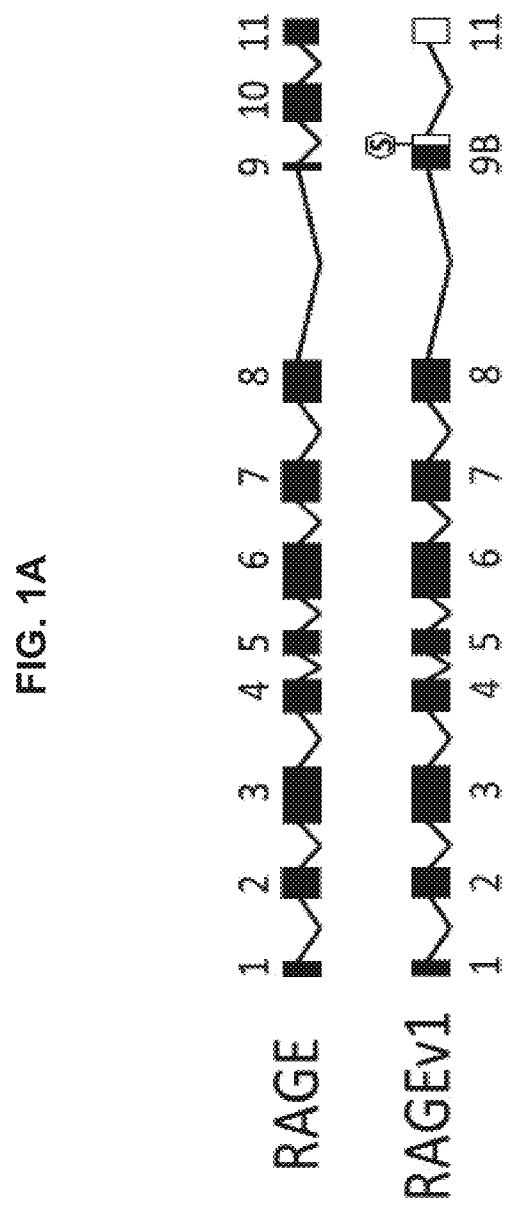
FIG. 1a shows the alternative splicing of RAGE that generates RAGE and RAGE_v1. Exons are shown as boxes. Coding sequences are black and non-coding sequence are white. Angled lines denote splicing events. S=premature termination codon.

Antisense oligonucleotide (AON) are short, synthetic, antisense, modified strands of DNA or RNA that can selectively hybridise to pre-RNA/mRNA through Watson-Crick base pairing and selectively modulate the function of the target RNA.

When AONs are used to modulate alternative splicing of mRNA, they are often referred to as splice-switching oligonucleotides (SSO). In the present invention, the terms AON and SSO may be used interchangeably. SSOs base-pair with a pre-mRNA and disrupt the normal splicing repertoire of the transcript by blocking the RNA-RNA base-pairing or protein-RNA binding interactions that occur between components of the splicing machinery and the pre-mRNA. SSOs can induce "skipping" of selected exons and/or retention of intronic sequences to modulate the product of translation. This can be achieved by targeting splice sites directly or by targeting cis-acting sequences involved in enhancing or silencing splicing by modulating binding of specific proteins or altering secondary structure of the pre mRNA.

Therapeutic SSOs may be used for the treatment of genetic disorders, to skip faulty or misaligned sections allowing for the generation of internally deleted, but now functional protein as a therapy.

Alternative splicing is recognized as an important layer of post-transcriptional gene regulation for the Receptor for Advanced Glycation End-products (RAGE). Although most RAGE is expressed in its full length isoform, a number of different coding isoforms are generated through alternative splicing (also known as splicoforms), including splicoforms with N-terminal truncations, C-terminal truncations, and splicoforms retaining intronic sequences. These different splicoforms may act as possible regulators of the full-length RAGE receptor either by competitive ligand binding or by displacing the full-length protein from binding partners. Over twenty splicoforms have been identified in different tissues such as lung, liver, kidney, smooth muscle, endothelial cells and brain.

The different RAGE gene splice variants have been named RAGE, RAGE_v1 to RAGE_v19 according to the Human Gene Nomenclature Committee. For example, (run on) retention of intron 9 (exon 9b) results in a premature stop and the complete loss of the transmembrane and cytoplasmic domains generating a C-truncated soluble splicoform (RAGE_v1, endogenous secretory RAGE or esRAGE) that constitutes ~5% of circulating RAGE in humans. Lacking any signalling elements or the transmembrane domain, esRAGE is able to act as a decoy receptor, competing with full length RAGE for ligands or increasing ligand clearance. Higher circulating levels of esRAGE are associated with improved health outcomes and longevity while lower esRAGE is associated with many disease states including but not limited to atherosclerosis, diabetes, the metabolic syndrome, cardiovascular mortality, anaemia, autism and various tumorigenic states. Treatment of diabetic mice with recombinant esRAGE reduces atherosclerosis, vascular inflammation, renal and retinal damage.

RAGEΔ (also known as DN RAGE or RAGEv20), lacks 16 amino acids of the intracellular domain, but retains ligand binding and transmembrane domains so acts a dominant-negative inhibitor of cell surface RAGE. Splicing events resulting in changes in the extracellular domain may also affect the ligand binding domain, by insertion, deletion, or removal of some or all of the Ig-V domain of RAGE. For example, N-RAGE begins at an alternate start site in exon 3, so has no signal peptide or V-domain required for ligand binding.

Aberrant splicing of RAGE (and therefore dysfunctional RAGE signalling) has been reported in diabetes, some cancers and Alzheimer's disease.

The skipping of exon 10 in esRAGE-type splicing is ascribed to the limitation of intron length in higher eukaryotes. Roughly 45 nucleotides must separate the 5' splice site and branch point, and the minimum distance between the branch point and 3' splice site appears to be approximately 18 nucleotides, respectively. Therefore introns shorter than 70 nucleotides are extremely rare in mammals and cannot be spliced out efficiently. When the esRAGE 5' splice site in intron 9 is selected, the distance between this site and the 3' splice site that borders exon 10 is 46 nucleotides, which is considerably shorter than the lower limit of the intron length. Therefore, the use of the downstream, esRAGE 5' splice site of intron 9 and the inclusion of exon 10 would be mutually exclusive. Among the known splice variants analyzed, all variants that used the downstream esRAGE 5' splice site in intron 9 skipped exon 10; in contrast, all variants that used the upstream RAGE 5' splice site in intron 9 included exon 10. Thus, the available evidence indicates that the selection of either one of the two alternative 5' splice sites in intron 9 couples with inclusion or exclusion of exon 10. The means of regulation of this splicing or an external means to modulate has been previously unknown.

The present invention uses SSOs to selectively manipulate the alternative splicing pattern of RAGE pre-mRNA, resulting in the generation of either natural RAGE mRNA splicoforms that are either non-functional or that act as a decoy receptor to antagonise ligand dependent activation and ligand-independent transactivation of full length RAGE.

Notably, there are no common RAGE polymorphisms at these splice sites. The RAGE sequence is highly conserved. Therefore personalisation or individualised sequence modification is not required, unlike the management of genetic disorders with exon skipping technologies.

The present invention provides an alternative method for the treatment, prevention or amelioration of the effects of diseases in which RAGE is implicated in the development or progression, including but not limited to neurodegenerative diseases, cancer, lung disorders, or inflammatory diseases, by developing AONs that modulate the alternative splicing of RAGE pre-mRNA or part thereof.

Broadly, according to one aspect of the invention, there is provided an isolated or purified AON for modulating pre-mRNA splicing in the Receptor for Advanced Glycation End-products (RAGE) gene transcript or part thereof. Preferably, there is provided an isolated or purified AON for inducing exon exclusion and/or intron retention in the RAGE pre mRNA or part thereof.

The invention provides an AON capable of binding to a selected target on a Receptor for Advanced Glycation End-products (RAGE) gene transcript to modulate pre-mRNA splicing in the RAGE gene transcript or part thereof.

For example, in one aspect of the invention, there is provided an AON of 10 to 50 nucleotides comprising a targeting sequence complementary to a region of the RAGE pre-mRNA or part thereof associated with the binding of a protein involved in the regulation of alternative splicing of mRNA.

TABLE 1

| | Sequence of the human RAGE gene |
|---|---|
| 5' upstream sequence | . . . aggactcttgtcccaaaggcatgaattcctagcattccctgtgacaagac (SEQ ID NO: 32) |
| Exon 1 | GACTGAAAGATGGGGGCTGGAGAGAGGGTGCAGGCCCCACCTAGGGCGGAGGCCAC AGCAGGGAGAGGGGCAGACAGAGCCAGGACCCTGGAAGGAAGCAGGATGGCAGCCG GAACAGCAGTTGGAGCCTGGGTGCTGGTCCTCAGTCTGTGGG (SEQ ID NO: 33) |
| Intron 1-2 | gtgagccactccctcaaccccactg (SEQ ID NO: 34) . . . cctctacc atggtgctatctcccag (SEQ ID NO: 35) |
| Exon 2 | GGGCAGTAGTAGGTGCTCAAAACATCACAGCCCGGATTGGCGAGCCACTGGTGCTG AAGTGTAAGGGGGCCCCCAAGAAACCACCCCAGCGGCTGGAATGGAAACTG (SEQ ID NO: 36) |
| Intron 2-3 | gtaagcggggctcctgttgcagcct (SEQ ID NO: 37) . . . ttaggccc tgcttctctgcttctag (SEQ ID NO: 38) |
| Exon 3 | AACACAGGCCGGACAGAAGCTTGGAAGGTCCTGTCTCCCCAGGGAGGAGGCCCCTG GGACAGTGTGGCTCGTGTCCTTCCCAACGGCTCCCTCTTCCTTCCGGCTGTCGGGA TCCAGGATGAGGGGATTTTCCGGTGCCAGGCAATGAACAGGAATGGAAAGGAGACC AAGTCCAACTACCGAGTCCGTGTCTACC (SEQ ID NO: 39) |
| Intron 3-4 | gtaagaattccagggtcttctccaa (SEQ ID NO: 40) . . . tctgactg gattttcctccttcag (SEQ ID NO: 41) |

TABLE 1-continued

Sequence of the human RAGE gene

| | |
|---|---|
| Exon 4 | AGATTCCTGGGAAGCCAGAAATTGTAGATTCTGCCTCTGAACTCACGGCTGGTGTT CCCAATAAG (SEQ ID NO: 42) |
| Intron 4-5 | gtagtggaagaaagcaggagaagta (SEQ ID NO: 43) . . . tctgaggt caccactctttccccag (SEQ ID NO: 44) |
| Exon 5 | GTGGGGACATGTGTGTCAGAGGGAAGCTACCCTGCAGGGACTCTTAGCTGGCACTT GGATGGGAAGCCCCTGGTGCCTAATGAGAAGG (SEQ ID NO: 45) |
| Intron 5-6 | gtgagtcctaaggtgcccccaagc (SEQ ID NO: 46) . . . aatttgt cttatcctcccatcatag (SEQ ID NO: 47) |
| Exon 6 | GAGTATCTGTGAAGGAACAGACCAGGAGACACCCTGAGACAGGGCTCTTCACACTG CAGTCGGAGCTAATGGTGACCCCAGCCCGGGGAGGAGATCCCCGTCCCACCTTCTC CTGTAGCTTCAGCCCAGGCCTTCCCCGACACCGGGCCTTGCGCACAGCCCCCATCC AGCCCCGTGTCTGGG (SEQ ID NO: 48) |
| Intron 6-7 | gtgagcataggtggggagggcccca (SEQ ID NO: 49) . . . acctcaaa acccttccaactcccag (SEQ ID NO: 50) |
| Exon 7 | AGCCTGTGCCTCTGGAGGAGGTCCAATTGGTGGTGGAGCCAGAAGGTGGAGCAGTA GCTCCTGGTGGAACCGTAACCCTGACCTGTGAAGTCCCTGCCCAGCCCTCTCCTCA AATCCACTGGATGAAGGAT (SEQ ID NO: 51) |
| Intron 7-8 | gtgagtgacctggagagagggctg (SEQ ID NO: 52) . . . gtctcctc tccccttcccccaccag (SEQ ID NO: 53) |
| Exon 8 | GGTGTGCCCTTGCCCCTTCCCCCCAGCCCTGTGCTGATCCTCCCTGAGATAGGGCC TCAGGACCAGGGAACCTACAGCTGTGTGGCCACCCATTCCAGCCACGGGCCCCAGG AAAGCCGTGCTGTCAGCATCAGCATCATCG (SEQ ID NO: 54) |
| Intron 8-9 | gtgagacctctccccaagccctaca (SEQ ID NO: 55) . . . gactggat ccaactttgtcttccag (SEQ ID NO: 56) |
| Exon 9 | AACCAGGCGAGGAGGGGCCAACTGCAG (SEQ ID NO: 57) |
| Intron 9-10 | gtgaggggtttgataaagtcaggga (SEQ ID NO: 58) . . . ctcaattt tccctgtctccgtacag (SEQ ID NO: 59) |
| Exon 10 | GCTCTGTGGGAGGATCAGGGCTGGGAACTCTAGCCCTGGCCCTGGGGATCCTGGGA GGCCTGGGGACAGCCGCCCTGCTCATTGGGGTCATCTTGTGGCAAAGGCGGCAACG CGAGGAGAGGAGAG (SEQ ID NO: 60) |
| Intron 10-11 | gtgagtggagaaagccagacccctc (SEQ ID NO: 61) . . . cattcccc ccaatctttctcctcag (SEQ ID NO: 62) |
| Exon 11 | GAAGGCCCCAGAAAACCAGGAGGAAGAGGAGGAGCGTGCAGAACTGAATCAGTCGG AGGAACCTGAGGCAGGCGAGAGTAGTACTGGAGGGCCTTGAGGGGCCCACAGACAG ATCCCATCCATCAGCTCCCTTTTCTTTTTCCCTTGAACTGTTCTGGCCTCAGACCA ACTCTCTCCTGTATAATCTCTCTCCTGTATAACCCCACCTTGCCAAGCTTTCTTCT ACAACCAGAGCCCCCCACAATGATGATTAAACACCTGACACATCTTGC (SEQ ID NO: 63) |
| 3' downstream sequence | tcttgtgtgtctgtgtgtgtatgagacacaacctcaccctatacct . . . (SEQ ID NO: 64) |

TABLE 2

Domains of the human RAGE gene

| Exon | Domain |
|---|---|
| 1 | N-terminal signal peptide |
| 2 | V-type immunoglobulin domain |
| 3 | V-type immunoglobulin domain |
| 4 | V-type immunoglobulin domain |
| 5 | C-type immunoglobulin domains 1 & 2 |
| 6 | C-type immunoglobulin domains 1 & 2 |
| 7 | C-type immunoglobulin domains 1 & 2 |
| 8 | C-type immunoglobulin domains 1 & 2 |
| 9 | C-type immunoglobulin domains 1 & 2 |
| 10 | transmembrane domain |
| 11 | hydrophobic intracellular cytoplasmic domain |

In contrast to other AON based therapies, the present invention does not induce increased degradation of RNA via recruitment of RNase H, wherein the RNase H preferentially binds and degraded RNA bound in duplex to DNA of the RAGE gene. Nor does it rely on hybridization of the AON to the RAGE genomic DNA or the binding of AONs to mRNA to modulate the amount of RAGE protein produced by interfering with normal functions such as replication, transcription, translocation and translation. Rather, the AONs are used to modulate pre-mRNA splicing in a RAGE gene transcript or part thereof and induce exon "skipping" or (run on) retention of intronic sequences. The strategy preferably reduces the expression of RAGE mRNA splicoforms capable of mediating RAGE-dependent signalling and/or increases the generation of RAGE mRNA splicoforms that lack functional domains capable of mediating RAGE-dependent signalling.

According to a first aspect of the invention, there is provided AONs capable of binding to a selected target on a RAGE gene transcript to modulate pre-mRNA splicing in a RAGE gene transcript or part thereof. Broadly, there is provided an isolated or purified AON for inducing targeted exon exclusion/intron retention in a RAGE gene transcript or part thereof.

By "isolated" is meant material that is substantially or essentially free from components that normally accompany it in its native state. For example, an "isolated polynucleotide" or "isolated oligonucleotide," as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells, refers to the purification of cells (e.g., fibroblasts, lymphoblasts) from a source subject (e.g., a subject with a polynucleotide repeat disease). In the context of DNA, mRNA or protein, "isolating" refers to the recovery of the DNA, mRNA or protein from a source, e.g., cells.

An AON can be said to be "directed to" or "targeted against" a target sequence with which it hybridizes. In certain embodiments, the target sequence includes a region including a 3' or 5' splice site of a pre-processed mRNA, a branch point, or other sequences involved in the regulation of splicing, including splice enhancers and splice silencers and sites determining the secondary structure of RNA that influence splicing. The target sequence may be within an exon or within an intron or spanning an intron/exon junction.

In certain embodiments, the AON has sufficient sequence complementarity to a target RNA (i.e., the RNA for which splice site selection is modulated) to block a region of a target RNA (e.g., pre-mRNA) in an effective manner. In exemplary embodiments, such blocking of RAGE pre-mRNA serves to modulate splicing, either by masking a binding site for a splicosomal protein that would otherwise modulate splicing and/or by altering the structure of the targeted RNA. In some embodiments, the target RNA is target pre-mRNA (e.g., RAGE gene pre-mRNA).

An AON having a sufficient sequence complementarity to a target RNA sequence to modulate splicing of the target RNA means that the AON has a sequence sufficient to trigger the masking of a binding site for a native protein that would otherwise modulate splicing and/or alters the three-dimensional structure of the targeted RNA.

Selected AONs can be made shorter, e.g., about 12 bases, or longer, e.g., about 50 bases, and include a small number of mismatches, as long as the sequence is sufficiently complementary to effect splice modulation upon hybridization to the target sequence, and optionally forms with the RNA a heteroduplex having a Tm of 45° C. or greater.

Preferably, the AON is selected from the group comprising SEQ ID NOS: 1-31 and/or the sequences set forth in any of Tables 3a-3d. More preferably, the AON is SEQ ID NO: 11, 18, 19, or 20.

In certain embodiments, the degree of complementarity between the target sequence and AON is sufficient to form a stable duplex. The region of complementarity of the AONs with the target RNA sequence may be as short as 8-11 bases, but can be 12-15 bases or more, e.g., 10-50 bases, 10-40 bases, 12-30 bases, 12-25 bases, 15-25 bases, 12-20 bases, or 15-20 bases, including all integers in between these ranges. An AON of about 16-17 bases is generally long enough to have a unique complementary sequence. In certain embodiments, a minimum length of complementary bases may be required to achieve the requisite binding Tm, as discussed herein.

In certain embodiments, oligonucleotides as long as 50 bases may be suitable, where at least a minimum number of bases, e.g., 10-12 bases, are complementary to the target sequence. In general, however, facilitated or active uptake in cells is optimized at oligonucleotide lengths of less than about 30 bases. For phosphorodiamidate morpholino oligomer (PMO) AONs described further herein, an optimum balance of binding stability and uptake generally occurs at lengths of 18-25 bases. Included are AONs (e.g., PMOs, PMO-X, PNAs, LNAs, TINA, 2'-OMe) that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 bases.

In certain embodiments, AONs may be 100% complementary to the target sequence, or may include mismatches, e.g., to accommodate variants, as long as a heteroduplex formed between the oligonucleotide and target sequence is sufficiently stable to withstand the action of cellular nucleases and other modes of degradation which may occur in vivo. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligonucleotide and the target sequence.

Mismatches, if present, are typically less destabilizing toward the end regions of the hybrid duplex than in the middle. The number of mismatches allowed will depend on the length of the oligonucleotide, the percentage of G:C base pairs in the duplex, and the position of the mismatch(es) in the duplex, according to well understood principles of duplex stability. Although such an AON is not necessarily 100% complementary to the target sequence, it is effective to stably and specifically bind to the target sequence, such that splicing of the target pre-RNA is modulated.

The stability of the duplex formed between an AON and a target sequence is a function of the binding Tm and the susceptibility of the duplex to cellular enzymatic cleavage. The Tm of an oligonucleotide with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide Hybridization Techniques, Methods Enzymol. Vol. 154 pp. 94-107. In certain embodiments, AONs may have a binding Tm, with respect to a complementary-sequence RNA, of greater than body temperature and preferably greater than about 45° C. or 50° C. Tm's in the range 60-80° C. or greater are also included.

Additional examples of variants include AONs having about or at least about 70% sequence identity or homology, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity or homology, over the entire length of any of SEQ ID NOS: 1-31 and/or the sequences set forth in any of Tables 3a-3d. More preferably, the AON is SEQ ID NO: 11, 18, 19, or 20.

More specifically, there is provided an AON capable of binding to a selected target site to modify pre-mRNA splicing in a RAGE gene transcript or part thereof. The AON is preferably selected from SEQ ID NOS: 1-31 and/or the sequences set forth in any of Tables 3a-3d. More preferably, the AON is SEQ ID NO: 11, 18, 19, or 20.

The modification of pre-mRNA splicing preferably induces "skipping", or the removal of one or more exons or retention of introns of the mRNA. The resultant protein is preferably of a shorter length when compared to the parent full-length RAGE protein due to either internal truncation or premature termination. These truncated RAGE proteins may be termed splicoforms of the full length RAGE protein.

The remaining exons of the mRNA generated may be in-frame and produce a shorter protein with a sequence that is similar to that of the parent full length protein, except that it has an internal truncation in a region between the original 3' and 5' ends. In another possibility, the exon skipping may induce a frame shift that results in a protein wherein the first part of the protein is substantially identical to the parent full length protein, but wherein the second part of the protein has a different sequence (e.g. a nonsense sequence) due to a frame-shift. Alternatively, the exon skipping may induce the production of a prematurely terminated protein due to a disruption of the reading frame and presence of a premature termination of translation. The prematurely terminated protein may be the result of mRNA that is prematurely terminated (e.g. skipping of exons 10 and/or 11) or may be the result of a run on into an intron (e.g. RAGE 9b) or missense skip which provides an mRNA that contains the exon 10 and/or 11 mRNA, but which does not provide expression of the protein encoded by these exons.

Skipping individual exons of exons 1 to 9 will preferably disrupt the reading frame of the RAGE transcript. This will lead to increased degradation of RNA through nonsense mediated decay.

Skipping individual exons of exons 1 to 11 will preferably keep the reading frame intact. This will preferably lead to translation into an internally truncated protein. The truncated protein or RAGE mRNA splicoform may have a completely ablated function, may have a reduced function or act as a decoy receptor.

Preferably, these truncated, nonsense or prematurely terminated proteins are lacking one or more functional domains involved the induction of intracellular signalling pathways by RAGE ligands or non-ligand-dependent transactivation of RAGE by collocated GPCRs. For example, Exon 10 encodes a transmembrane domain and removing this exon may generate a soluble RAGE protein, which could potentially act as a soluble decoy or competitive antagonist of ligand induced signalling via RAGE. Truncated, nonsense or prematurely terminated proteins may further lack an attachment or binding site for other factors, removal of which may lead to a reduction in interaction of the RAGE protein with relevant signalling pathways.

Alternatively, the removal of one or more exons may lead to misfolding of the RAGE protein and a reduction in the ability of the protein to be successfully transported through the membrane.

The presence of internally truncated proteins (i.e. proteins lacking the amino acids encoded by one or more exons) is preferable. If the RAGE protein is inhibited, there may be problems with elevation of RAGE transcription as the body tries to compensate for the reduction in the total amount of RAGE protein. In contrast, the presence of an internally truncated protein (preferably lacking one or more of the features of the complete RAGE protein), should be sufficient to prevent elevated transcription, but still provide a therapeutic advantage due to a reduction in the total amount of functional RAGE protein.

The AON induced exon skipping of the present invention need not completely or even substantially ablate the function of the RAGE protein. Preferably, the modulation of alternative splicing via the exon skipping process results in a reduced or compromised functionality of the RAGE protein.

The different isoforms of RAGE produced using different skipping strategies could result in proteins with ablated or reduced signalling activity that could preferably be used to treat or prevent different diseases associated with RAGE activity, such as neurodegenerative diseases, cancer, lung disorders, or inflammatory diseases. Alternative splicing strategies may form truncated proteins or proteins with reduced functions that can be preferably used as treatments for specific aspects, forms or progression of the diseases associated with RAGE expression and activity.

The skipping process of the present invention, using AONs, may exclude (skip) an individual exon, or may result in skipping two or more exons at once.

The skipping process of the present invention, using AONs, may include retention of intronic sequences with or without directly skipping one or more exons.

The AONs of the invention may be a combination of two or more AONs capable of binding to a selected target to induce exon exclusion in a RAGE gene transcript. The combination may be a cocktail of two or more AONs and/or a construct comprising two or more or two or more AONs joined together.

TABLE 3a

Sequence of AONs for modulation of alternative splicing in human RAGE Exon 9

| SEQ ID NO | AON# | Name | Sequence (5' to 3') |
|---|---|---|---|
| 1 | 3668 | H-AGERex9A(-10 +15) | CCUCCUCGCCUGGUUCUGGAAGACA |
| 2 | 3669 | H-AGERex9A(+02 -F21) | UUGGCCCCUCCUCGCCUGGU |
| 3 | 3670 | H-AGERex9A(+08 -F27) | CUGCAGUUGGCCCCUCCUCG |
| 4 | 3671 | H-AGERex9D(+07 -13) | UCAAACCCCUCACCUGCAGU |
| 5 | 4103 | H-AGERex9A(+3 +27) | CCUGCAGUUGGCCCCUCCUCGCCUG |
| 6 | 4104 | H-AGERex9A(+10 +27) | CCCCUCACCUGCAGUUGGCCCUCC |
| 7 | 4105 | H-AGERex9A(+8 +25) | GCAGUUGGCCCCUCCUC |
| 8 | 4106 | H-AGERex9D(+22 -3) | CACCUGCAGUUGGCCCCUCCUCGCC |

TABLE 3b

Sequence of AONs for modulation of alternative splicing in human RAGE Exon 10

| SEQ ID NO | AON# | Name | Sequence (5' to 3') |
|---|---|---|---|
| 9 | 3777 | AGER_H10A(-10 +15) | AUCCUCCCACAGAGCCUGUACGGAG |
| 10 | 3778 | AGER_H10A(-5 +20) | CCCUGAUCCUCCCACAGAGCCUGUA |
| 11 | 3779 | AGER_H10A(+90 +114) | GGCGUUGCCGCCUUUGCCACAAGAU |

TABLE 3b-continued

Sequence of AONs for modulation of alternative splicing in human RAGE Exon 10

| SEQ ID NO | AON# | Name | Sequence (5' to 3') |
|---|---|---|---|
| 12 | 3780 | AGER_H10D(+20 -5) | CUCACCUCUCCUCUCCUCG GCGUUG |
| 13 | 3781 | AGER_H10D(+15 -10) | CUCCACUCACCUCUCCUCU CCUCGG |
| 14 | 82 | AGER_H10A (+60 +79) | AGCAGGGCGGCUGUCCCCA G |
| 15 | 83 | AGER_H10A (+75 +99) | GCCACAAGAUGACCCCAAU GAGCAG |
| 16 | 84 | AGER_A10 (+80 +104) | CCUUUGCCACAAGAUGACC CCAAUG |
| 17 | 85 | AGER_A10 (+85 +109) | UGCCGCCUUUGCCACAAGA UGACCC |
| 18 | 87 | AGER_H10(+95 +119) | UCCUCGGCGUUGCCGCCUU UGCCAC |
| 19 | 90 | AGER_H10A(+90 -F102) | UUUGCCACAAGAU |
| 20 | 93 | AGER_H10A(+88 -F107) | CCGCCUUUGCCACAAGAUG A |

TABLE 3c

Sequence of AONs for modulation of alternative splicing in human RAGE Intron 9

| SEQ ID NO | AON# | Name | Sequence (5' to 3') |
|---|---|---|---|
| 21 | 88 | AGER_H10A(-75 -51) | UUUCUUGUUGACCAUCCCC CCAGUC |
| 22 | 89 | AGER_H10A(-86 -62) | CCAUCCCCCCAGUCACAUG UGUUGG |

TABLE 3d

Sequence of AONs for modulation of alternative splicing in murine RAGE

| SEQ ID NO | AON# | Name | Sequence (5 to 3') |
|---|---|---|---|
| 23 | 3672 | M-AgerEx9A(-10 +15) | CCUCCUCGCCUGGUUCUGGAAGACA |
| 24 | 3673 | M-AgerEx9A(+02 -F21) | CUGGCCCCUCAUCGCCGGUU |
| 25 | 3674 | M-AgerEx9A(+08 --F27) | CUUCAGCUGGCCCCUCAUCG |
| 26 | 3675 | M-AgerEx9D(+07 -13) | UCCAGUCCCUCACCUUCAGC |
| 27 | m3779 | M-AgerEx10A(+90 -F14) | UGGGUUGUCGUUUUCGCCACAGGAU |
| 28 | m97 | M-AgerEx10A(+48, -F70) | ACUACUCCCAGGCCUCCCAGGAU |
| 29 | m98 | M-AgerEx10A(+56--F79) | GCAGGGCUACUACUCCCAGGCA |
| 30 | m101 | M-AgerEx10D(-15 +10) | UCUCACUCACCUCUCCUCACGCCUG |
| 31 | m102 | M-AgerEx10A(-5 -F20) | CCCAGACUCACCCACAGAGCCUGUA |

The invention further provides a method for modulating alterative splicing in a RAGE gene transcript, the method including the step of:

providing one or more of the AONs as described herein and allowing the oligomer(s) to bind to a target nucleic acid site.

According to yet another aspect of the invention, there is provided a nucleic acid sequence target for modulating alterative splicing of RAGE pre mRNA comprising the DNA equivalents of the nucleic acid sequences selected from the group consisting of SEQ ID NOs: 1-31 and/or the sequences set forth in any of Tables 3a-3d, and sequences complementary thereto. More preferably, the AON is SEQ ID NO: 11, 18, 19, or 20. The AON may be a combination of AONs, preferably a combination of SEQ ID NO: 11 and 10, or SEQ ID NO: 11 and 13.

Designing AONs to completely mask consensus splice sites may not necessarily generate a change in splicing of the targeted exon. Furthermore, the inventors have discovered that size or length of the AON itself is not always a primary factor when designing AONs. With some targets, AONs as short as 20 bases were able to induce some exon inclusion, in certain cases more efficiently than other longer (e.g. 25 bases) oligomers directed to the same exon.

The inventors have also discovered that there does not appear to be any standard motif that can be blocked or masked by AONs to redirect splicing. It has been found that AONs must be designed and their individual efficacy evaluated empirically for each gene target.

More specifically, the AON may be selected from those set forth in any of Tables 3a-3d. The sequences are preferably selected from the group consisting of any one or more of any one or more of SEQ ID NOs: 1-31, and combinations or cocktails thereof. More preferably, the AON is SEQ ID NO: 11, 18, 19, or 20. The combination of AONs is preferably a combination of SEQ ID NO: 11 and 10, or SEQ ID NO: 11 and 13. This includes sequences which can hybridise to such sequences under stringent hybridisation conditions, sequences complementary thereto, sequences containing modified bases, modified backbones, and functional truncations or extensions thereof which possess or modulate pre-mRNA processing activity in a RAGE gene transcript.

The oligomer and the DNA, cDNA or RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or pairing such that stable and specific binding occurs between the oligomer and the DNA, cDNA or RNA target. It is understood in the art that the sequence of an AON need not be 100% complementary to that of its target sequence to be specifically hybridisable. An AON is specifically hybridisable when binding of the compound to the target DNA or RNA molecule interferes with the normal function of the target DNA or RNA product, and there is a sufficient degree of complementarity to avoid non-specific binding of the AON to non-target sequences under conditions in which specific binding is desired, i.e., under physiological conditions in the case of in vivo assays or therapeutic treatment, and in the case of in vitro assays, under conditions in which the assays are performed.

Selective hybridisation may be under low, moderate or high stringency conditions, but is preferably under high stringency. Those skilled in the art will recognise that the stringency of hybridisation will be affected by such conditions as salt concentration, temperature, or organic solvents, in addition to the base composition, length of the complementary strands and the number of nucleotide base mismatches between the hybridising nucleic acids. Stringent temperature conditions will generally include temperatures in excess of 30° C., typically in excess of 37° C., and preferably in excess of 45° C., preferably at least 50° C., and typically 60° C.-80° C. or higher. Stringent salt conditions will ordinarily be less than 1000 mM, typically less than 500 mM, and preferably less than 200 mM. However, the combination of parameters is much more important than the measure of any single parameter. An example of stringent hybridisation conditions is 65° C. and 0.1×SSC (1×SSC=0.15 M NaCl, 0.015 M sodium citrate pH 7.0). Thus, the AONs of the present invention may include oligomers that selectively hybridise to the sequences provided in any of Tables 3a-3d, or SEQ ID NOs:1-31. More preferably, the AON is SEQ ID NO: 11, 18, 19, or 20.

It will be appreciated that the codon arrangements at the end of exons in structural proteins may not always break at the end of a codon, consequently there may be a need to delete more than one exon from the pre-mRNA to ensure in-frame reading of the mRNA. In such circumstances, a plurality of AONs may need to be selected by the method of the invention wherein each is directed to a different region responsible for inducing inclusion of the desired exon and/or intron. At a given ionic strength and pH, the Tm is the temperature at which 50% of a target sequence hybridizes to a complementary polynucleotide. Such hybridization may occur with "near" or "substantial" complementarity of the AON to the target sequence, as well as with exact complementarity.

Typically, selective hybridisation will occur when there is at least about 55% identity over a stretch of at least about 14 nucleotides, preferably at least about 65%, more preferably at least about 75% and most preferably at least about 90%, 95%, 98% or 99% identity with the nucleotides of the AON. The length of homology comparison, as described, may be over longer stretches and in certain embodiments will often be over a stretch of at least about nine nucleotides, usually at least about 12 nucleotides, more usually at least about 20, often at least about 21, 22, 23 or 24 nucleotides, at least about 25, 26, 27 or 28 nucleotides, at least about 29, 30, 31 or 32 nucleotides, at least about 36 or more nucleotides.

Thus, the AON sequences of the invention preferably have at least 75%, more preferably at least 85%, more preferably at least 86, 87, 88, 89 or 90% homology to the sequences shown in the sequence listings herein. More preferably there is at least 91, 92, 93 94, or 95%, more preferably at least 96, 97, 98% or 99%, homology. Generally, the shorter the length of the AON, the greater the homology required to obtain selective hybridisation. Consequently, where an AON of the invention consists of less than about 30 nucleotides, it is preferred that the percentage identity is greater than 75%, preferably greater than 85, 86, 87, 88, 89, 90, 91, 92, 93, 94, 95%, 96, 97, 98% or 99% compared with the AONs set out in the sequence listings herein. Nucleotide homology comparisons may be conducted by sequence comparison programs such as the GCG Wisconsin Bestfit program or GAP (Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

The AON of the present invention may have regions of reduced homology, and regions of exact homology with the target sequence. It is not necessary for an oligomer to have exact homology for its entire length. For example, the oligomer may have continuous stretches of at least 4 or 5 bases that are identical to the target sequence, preferably continuous stretches of at least 6 or 7 bases that are identical to the target sequence, more preferably continuous stretches of at least 8 or 9 bases that are identical to the target sequence. The oligomer may have stretches of at least 10, 11, 12, 13, 14, 15, 16, 17, 18, 19, 20, 21, 22, 23, 24, 25 or 26 bases that are identical to the target sequence. The remaining stretches of oligomer sequence may be intermittently identical with the target sequence; for example, the remaining sequence may have an identical base, followed by a non-identical base, followed by an identical base. Alternatively (or as well) the oligomer sequence may have several stretches of identical sequence (for example 3, 4, 5 or 6 bases) interspersed with stretches of less than perfect homology. Such sequence mismatches will preferably have no or very little loss of splice switching activity.

The term "modulate" or "modulates" includes to "increase" or "decrease" one or more quantifiable parameters, optionally by a defined and/or statistically significant amount. The terms "increase" or "increasing," "enhance" or "enhancing," or "stimulate" or "stimulating" refer generally to the ability of one or AONs or compositions to produce or cause a greater physiological response (i.e., downstream effects) in a cell or a subject relative to the response caused by either no AON or a control compound. The terms "decreasing" or "decrease" refer generally to the ability of one or AONs or compositions to produce or cause a reduced physiological response (i.e., downstream effects) in a cell or a subject relative to the response caused by either no AON or a control compound.

Relevant physiological or cellular responses (in vivo or in vitro) will be apparent to persons skilled in the art, and may include increases in the exclusion of specific exons in a RAGE-coding pre-mRNA, decreases in the amount of RAGE-coding pre-mRNA or decreases in the expression of functional RAGE protein in a cell, tissue, or subject in need thereof. An "increased" or "enhanced" amount is typically a statistically significant amount, and may include an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1, e.g., 1.5, 1.6, 1.7, 1.8) the amount produced by no AON (the absence of an agent) or a control compound. The term "reduce" or "inhibit" may relate generally to the ability of one or more AONs or compositions to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in the symptoms or pathology of a disease such as cancer, neurodegenerative diseases, lung disorders, and other inflammatory diseases. A "decrease" in a response may be statistically significant as compared to the response produced by no AON or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

The length of an AON may vary, as long as it is capable of binding selectively to the intended location within the pre-mRNA molecule. The length of such sequences can be determined in accordance with selection procedures described herein. Generally, the AON will be from about 10 nucleotides in length, up to about 50 nucleotides in length. It will be appreciated, however, that any length of nucleotides within this range may be used in the method. Preferably, the length of the AON is between 10 and 40, 10 and 35, 15 to 30 nucleotides in length or 20 to 30 nucleotides in length, most preferably about 25 to 30 nucleotides in length. For example, the oligomer may be 20, 21, 22, 23, 24, 25, 26, 27, 28, 29 or 30 nucleotides in length.

As used herein, an "AON" refers to a linear sequence of nucleotides, or nucleotide analogs, that allows the nucleobase to hybridize to a target sequence in an RNA by Watson-Crick base pairing, to form an oligonucleotide:RNA heteroduplex within the target sequence. The terms "AON", "AON", "oligomer" and "antisense compound" may be used interchangeably to refer to an oligonucleotide. The cyclic subunits may be based on ribose or another pentose sugar or, in certain embodiments, a morpholino group (see description of morpholino oligonucleotides below). Also contemplated are peptide nucleic acids (PNAs), locked nucleic acids (LNAs), and 2'-O-Methyl oligonucleotides, among other antisense agents known in the art.

Included are non-naturally-occurring AONs, or "oligonucleotide analogs", including AONs or oligonucleotides having (i) a modified backbone structure, e.g., a backbone other than the standard phosphodiester linkage found in naturally-occurring oligo- and polynucleotides, and/or (ii) modified sugar moieties, e.g., morpholino moieties rather than ribose or deoxyribose moieties. Oligonucleotide analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

One method for producing AONs is the methylation of the 2' hydroxyribose position and the incorporation of a phosphorothioate backbone produces molecules that superficially resemble RNA but that are much more resistant to nuclease degradation, although persons skilled in the art of the invention will be aware of other forms of suitable backbones that may be useable in the objectives of the invention.

To avoid degradation of pre-mRNA during duplex formation with the AONs, the AONs used in the method may be adapted to minimise or prevent cleavage by endogenous RNase H. This property is highly preferred, as the treatment of the RNA with the unmethylated oligomers, either intracellular or in crude extracts that contain RNase H, leads to degradation of the pre-mRNA:AON duplexes. Any form of modified AONs that is capable of by-passing or not inducing such degradation may be used in the present method. The nuclease resistance may be achieved by modifying the AONs of the invention so that it comprises partially unsaturated aliphatic hydrocarbon chain and one or more polar or charged groups including carboxylic acid groups, ester groups, and alcohol groups.

An example of AONs which when duplexed with RNA are not cleaved by cellular RNase H is 2'-O-methyl derivatives. Such 2'-O-methyl-oligoribonucleotides are stable in a cellular environment and in animal tissues, and their duplexes with RNA have higher Tm values than their ribo- or deoxyribo-counterparts. Alternatively, the nuclease resistant AONs of the invention may have at least one of the last 3'-terminus nucleotides fluoridated. Still alternatively, the nuclease resistant AONs of the invention have phosphorothioate bonds linking between at least two of the last 3'-terminus nucleotide bases, preferably having phosphorothioate bonds linking between the last four 3'-terminal nucleotide bases.

Increased splice-switching may also be achieved with alternative oligonucleotide chemistry. For example, the AON may be chosen from the list comprising: phosphoramidate or phosphorodiamidate morpholino oligomer (PMO); PMO-X; PPMO; peptide nucleic acid (PNA); a locked nucleic acid (LNA) and derivatives including alpha-L-LNA, 2'-amino LNA, 4'-methyl LNA and 4'-O-methyl LNA; ethylene bridged nucleic acids (ENA) and their derivatives; phosphorothioate oligomer; tricyclo-DNA oligomer (tcDNA); tricyclophosphorothioate oligomer; 2'O-Methyl-modified oligomer (2'-OMe); 2'-O-methoxy ethyl (2'-MOE); 2'-fluoro, 2'-fluroarabino (FANA); unlocked nucleic acid (UNA); thermostable twisted intercalating nucleic acid (TINA), hexitol nucleic acid (HNA); cyclohexenyl nucleic acid (CeNA); 2'-amino (2'-NH2); 2'-O-ethyl-eneamine or any combination of the foregoing as mixmers or as gapmers. To further improve the delivery efficacy, the above mentioned modified nucleotides are often conjugated with fatty acids/lipid/cholesterol/amino acids/carbohydrates/polysaccharides/nanoparticles etc. to the sugar or nucleobase moieties. These conjugated nucleotide derivatives can also be used to construct exon skipping AONs. Antisense oligonucleotide-induced splice modification of the huma RAGE gene transcripts have generally used either oligoribonucleotides, PNAs, 2OMe or MOE modified bases on a phosphorothioate backbone. Although 2OMeAOs are used for oligo design, due to their efficient uptake in vitro when delivered as cationic lipoplexes, these compounds are susceptible to nuclease degradation and are not considered ideal for in vivo or clinical applications. When alternative chemistries are used to generate the AONs of the present invention, the uracil (U) of the sequences provided herein may be replaced by a thymine (T).

Included within the AONs of the present invention are non-naturally-occurring oligomers, or "oligonucleotide analogues," including oligomers having (i) a modified backbone structure, e.g., a backbone other than the standard phosphodiester linkage found in naturally-occurring oligo- and polynucleotides, and/or (ii) modified sugar moieties, e.g., morpholino moieties rather than ribose or deoxyribose moieties. Oligomer analogues support bases capable of hydrogen bonding by Watson-Crick base pairing to standard polynucleotide bases, where the analogue backbone presents the bases in a manner to permit such hydrogen bonding in a sequence-specific fashion between the oligomer analogue molecule and bases in a standard polynucleotide (e.g., single-stranded RNA or single-stranded DNA). Preferred analogues are those having a substantially uncharged, phosphorus containing backbone.

Antisense oligonucleotides that do not activate RNase H can be made in accordance with known techniques (see, e.g., U.S. Pat. No. 5,149,797). Such AONs, which may be deoxyribonucleotide or ribonucleotide sequences, simply contain any structural modification which sterically hinders or prevents binding of RNase H to a duplex molecule containing the oligomer as one member thereof, which structural modification does not substantially hinder or disrupt duplex formation. Because the portions of the oligomer involved in duplex formation are substantially different from those portions involved in RNase H binding thereto, numerous AONs that do not activate RNase H are available. For example, such AONs may be oligomers wherein at least one, or all, of the inter-nucleotide bridging phosphate residues are modified phosphates, such as methyl phosphonates, methyl phosphorothioates, phosphoromorpholidates, phosphoropiperazidates boranophosphates, amide linkages and phosphoramidates. For example, every other one of the internucleotide bridging phosphate residues may be modified as described. In another non-limiting example, such AONs are molecules wherein at least one, or all, of the nucleotides contain a 2' lower alkyl moiety (such as, for example, $C_1$-$C_4$, linear or branched, saturated or unsaturated alkyl, such as methyl, ethyl, ethenyl, propyl, 1-propenyl, 2-propenyl, and isopropyl). For example, every other one of the nucleotides may be modified as described.

While the AONs described above are a preferred form of the AONs of the present invention, the present invention includes other oligomeric antisense molecules, including but not limited to oligomer mimetics such as are described below.

Specific examples of preferred AONs useful in this invention include oligomers containing modified backbones or non-natural inter-nucleoside linkages. As defined in this specification, oligomers having modified backbones include those that retain a phosphorus atom in the backbone and those that do not have a phosphorus atom in the backbone. For the purposes of this specification, and as sometimes referenced in the art, modified oligomers that do not have a phosphorus atom in their inter-nucleoside backbone can also be considered to be AONs.

In other preferred oligomer mimetics, both the sugar and the inter-nucleoside linkage, i.e., the backbone, of the nucleotide units are replaced with novel groups. The base units are maintained for hybridization with an appropriate nucleic acid target compound. One such oligomeric compound, an oligomer mimetic that has been shown to have excellent hybridization properties, is referred to as a peptide nucleic acid (PNA). In PNA compounds, the sugar-backbone of an oligomer is replaced with an amide containing backbone, in particular an aminoethylglycine backbone. The nucleo-bases are retained and are bound directly or indirectly to aza nitrogen atoms of the amide portion of the backbone.

Another preferred chemistry is the phosphorodiamidate morpholino oligomer (PMO) oligomeric compounds, which are not degraded by any known nuclease or protease. These compounds are uncharged, do not activate RNase H activity when bound to a RNA strand and have been shown to exert sustained splice modulation after in vivo administration (Summerton and Weller, Antisense Nucleic Acid Drug Development, 7, 187-197).

Modified oligomers may also contain one or more substituted sugar moieties. Oligomers may also include nucleobase (often referred to in the art simply as "base") modifications or substitutions. Certain nucleobases are particularly useful for increasing the binding affinity of the oligomeric compounds of the invention. These include 5-substituted pyrimidines, 6-azapyrimidines, and N-2, N-6 and O-6 substituted purines, including 2-aminopropyladenine, 5-propynyluracil and 5-propynylcytosine.5-methylcytosine substitutions have been shown to increase nucleic acid duplex stability by 0.6-1.2° C., even more particularly when combined with 2'-O-methoxyethyl sugar modifications.

Another modification of the oligomers of the invention involves chemically linking to the oligomer one or more moieties or conjugates that enhance the activity, cellular distribution or cellular uptake of the oligomer. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, myristyl, or an octadecylamine or hexylamino-carbonyl-oxycholesterol moiety.

Cell penetrating peptides have been added to phosphorodiamidate morpholino oligomers to enhance cellular uptake and nuclear localization. Different peptide tags have been shown to influence efficiency of uptake and target tissue specificity, as shown in Jearawiriyapaisarn et al. (2008), Mol. Ther. 16 9, 1624-1629.

It is not necessary for all positions in a given compound to be uniformly modified, and in fact more than one of the aforementioned modifications may be incorporated in a single compound or even at a single nucleoside within an oligomer. The present invention also includes AONs that are chimeric compounds. "Chimeric" AONs or "chimeras," in the context of this invention, are AONs, particularly oligomers, which contain two or more chemically distinct regions, each made up of at least one monomer unit, i.e., a nucleotide in the case of an oligomer compound. These oligomers typically contain at least one region wherein the oligomer is modified so as to confer upon the oligomer or AON increased resistance to nuclease degradation, increased cellular uptake, and an additional region for increased binding affinity for the target nucleic acid.

The activity of AONs and variants thereof can be assayed according to routine techniques in the art. For example, splice forms and expression levels of surveyed RNAs and proteins may be assessed by any of a wide variety of well-known methods for detecting splice forms and/or expression of a transcribed nucleic acid or protein. Non-limiting examples of such methods include RT-PCR of spliced forms of RNA followed by size separation of PCR products, nucleic acid hybridization methods e.g., Northern blots and/or use of nucleic acid arrays; nucleic acid amplification methods; immunological methods for detection of proteins; protein purification methods; and protein function or activity assays.

RNA expression levels can be assessed by preparing mRNA/cDNA (i.e., a transcribed polynucleotide) from a cell, tissue or organism, and by hybridizing the mRNA/cDNA with a reference polynucleotide, which is a complement of the assayed nucleic acid, or a fragment thereof. cDNA can, optionally, be amplified using any of a variety of polymerase chain reaction or in vitro transcription methods prior to hybridization with the complementary polynucleotide; preferably, it is not amplified. Expression of one or more transcripts can also be detected using quantitative PCR to assess the level of expression of the transcript(s).

The present invention provides AON induced splice-switching of the RAGE gene transcript, clinically relevant oligomer chemistries and delivery systems to direct RAGE splice manipulation to therapeutic levels. Substantial decreases in the amount of full length RAGE mRNA, and hence RAGE protein from RAGE gene transcription, are achieved by:
  a) oligomer refinement in vitro using fibroblast cell lines, through experimental assessment of (i) intronic-enhancer target motifs, (ii) AON length and development of oligomer cocktails, (iii) choice of chemistry, and (iv) the addition of cell-penetrating peptides (CPP) to enhance oligomer delivery; and
  b) detailed evaluation of a novel approach to generate RAGE transcripts with one or more missing exons.

As such, it is demonstrated herein that alternative splicing of RAGE pre-mRNA can be modulated with specific AONs. In this way functionally significant decreases in the amount of full length (signalling capable) RAGE protein can be obtained, and or increases in the non-signalling decoy-receptor RAGE mRNA splicoform (RAGE_v1) or other decoy receptors can be achieved, thereby reducing the severe pathology associated with diseases such as such as neurodegenerative diseases, cancer, lung disorders, and other inflammatory diseases.

The AONs used in accordance with this invention may be conveniently made through the well-known technique of solid phase synthesis. Equipment for such synthesis is sold by several vendors including, for example, Applied Biosystems (Foster City, Calif.). One method for synthesising oligomers on a modified solid support is described in U.S. Pat. No. 4,458,066.

Any other means for such synthesis known in the art may additionally or alternatively be employed. It is well known to use similar techniques to prepare oligomers such as the phosphorothioates and alkylated derivatives. In one such automated embodiment, diethyl-phosphoramidites are used as starting materials and may be synthesized as described by Beaucage, et al., (1981) Tetrahedron Letters, 22:1859-1862.

The AONs of the invention are synthesised in vitro and do not include antisense compositions of biological origin, or genetic vector constructs designed to direct the in vivo synthesis of AONs. The molecules of the invention may also be mixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption.

The AONs of the present invention also can be used as a prophylactic or therapeutic, which may be utilised for the purpose of treatment of a disease. Accordingly, in one embodiment the present invention provides AONs that bind to a selected target in the RAGE pre-mRNA to induce efficient and consistent exon skipping as described herein, in a therapeutically effective amount, admixed with a pharmaceutically acceptable carrier, diluent, or excipient.

The invention therefore provides a pharmaceutical, prophylactic, or therapeutic composition to treat, prevent or ameliorate the effects of a disease associated with RAGE expression in a patient, the composition comprising:
  a) one or more AONs as described herein, and
  b) one or more pharmaceutically acceptable carriers and/or diluents.

Preferably the disease associated with RAGE expression is chosen from the list comprising: neurological disorders, cancers; cardiovascular disorders; digestive disorders; respiratory disorders, musculoskeletal, connective tissue disorders, kidney disorders, genital disorders, skin disorders, eye disorders and endocrine disorders.

In one form of the invention, the RAGE-related disorder is a cardiovascular disorder selected from the group: atherosclerosis, ischaemic heart disease, myocarditis, endocarditis, cardiomyopathy, acute rheumatic fever, chronic rhematic heart disease, cerebrovascular disease/stroke, heart failure, vascular calcification, peripheral vascular disease, and lymphangitis.

In one form of the invention, the RAGE-related disorder is a digestive system disorder selected from the group: periodontitis, oesophagitis, gastritis, gastro-duodenal ulceration, Crohn disease, ulcerative colitis, ischaemic colitis, enteritis and enterocolitis, peritonitis, alcoholic liver disease, hepatitis, toxic liver disease, biliary cirrhosis, hepatic fibrosis/cirrhosis, non-alcoholic fatty liver disease/non-alcoholic steatohepatitis (NAFLD/NASH), liver trauma and recovery from liver injury, trauma or surgery.

In one form of the invention, the RAGE-related disorder is a cancer selected from the group: malignant neoplasms of lip, oral cavity and pharynx, malignant neoplasms of digestive organs, malignant neoplasms of respiratory and intrathoracic organs, malignant neoplasms of bone and articular cartilage, melanoma and other malignant neoplasms of skin, malignant neoplasms of mesothelial and soft tissue, malignant neoplasm of breast, malignant neoplasms of female genital organs, malignant neoplasms of male genital organs, malignant neoplasms of urinary tract, malignant neoplasms of eye, brain and other parts of central nervous system, malignant neoplasms of thyroid and other endocrine glands, malignant neoplasms of lymphoid, haematopoietic and related tissue, malignant neoplasms of ill-defined, secondary and/or unspecified sites.

In one form of the invention, the RAGE-related disorder is a neurological disorder and is selected from the group: inflammatory diseases of the central nervous system, systemic atrophies primarily affecting the central nervous system, extrapyramidal and movement disorders, Parkinson's disease, demyelinating diseases of the central nervous system, Alzheimer's disease, circumscribed brain atrophy, Lewy body disease, epilepsy, migraine, neuropathic pain, diabetic neuropathy, polyneuropathies, glioma development and progression, spinal cord trauma, and ischaemic brain injury/stroke, brain trauma and recovery from brain injury, trauma or surgery.

In one form of the invention, the RAGE-related disorder is a muscluloskeletal disorder and is selected from the group: muscular dystrophy, congenital and storage myopathy, polymyositis, myasthaemic gravis, dermatomyositis, inclusion body myositis, muscle atrophy and muscle injury.

In one form of the invention, the RAGE-related disorder is a mental disorder and is selected from the group: dementia, Alzheimer's disease, vascular dementia, addiction, schizophrenia, major affective disorder, depression, mania, bipolar disorder, and anxiety disorder.

In one form of the invention, the RAGE-related disorder is a respiratory (pulmonary) disorder and is selected from the group: Acute upper respiratory infections, rhinitis, nasopharyngitis, sinusitis, laryngitis, influenza and pneumonia, acute bronchitis, acute bronchiolitis, asthma, chronic obstructive pulmonary disease (COPD), bronchiectasis, emphysema, chronic lung diseases due to external agents, Acute Respiratory Distress Syndrome (ARDS), pulmonary eosinophilia, and pleuritic, lung trauma and recovery from lung injury, trauma or surgery.

In one form of the invention, the RAGE-related disorder is a connective tissue disorder and is selected from the group: osteoarthritis, infectious arthritis, rheumatoid arthritis, psoriatic and enteropathic arthropathies, juvenile arthritis, gout and other crystal arthropathies, diabetic arthropathy, polyarteritis nodosa, Churg-Strauss, mucocutaneous lymph node syndrome [Kawasaki], hypersensitivity angiitis, Goodpasture syndrome, thrombotic microangiopathy, Wegener granulomatosis, Aortic arch syndrome [Takayasu], giant cell arteritis, polymyalgia rheumatica, microscopic polyangiitis, hypocomplementaemic vasculitis, systemic lupus erythematosus, dermatopolymyositis, polymyositis, systemic sclerosis, CR(E)ST syndrome, Sicca syndrome [Sjögren], mixed connective tissue disease, Behcet disease, traumatic muscle damage, sprain, strain, and fracture.

In one form of the invention, the RAGE-related disorder is a kidney disorder and is selected from the group: glomerulonephritis, nephritis, diabetic kidney disease, interstitial nephritis, obstructive and reflux nephropathy, acute renal failure, and chronic kidney disease.

In one form of the invention, the RAGE-related disorder is a genital disorder and is selected from the group: prostatitis, prostatic hypertrophy, prostatic dysplasia, salpingitis, oophoritis, pelvic inflammatory disease (PID), polycystic ovarian syndrome, cervicitis, cervical dysplasia, vaginitis, vulvitis.

In one form of the invention, the RAGE-related disorder is a skin disorder selected from the group: dermatitis, eczema, pemphigus/pemphygoid, psoriasis, pityriasis rosea, lichen planus, urticarial, erythrema multiforme, erythema nordosum, sunburn, keratosis, photoageing skin ulceration, superficial skin injury, and open wound.

In one form of the invention, the RAGE-related disorder is an eye disorder selected from the group: keratitis, conjunctivitis, retinitis, glaucoma, scleritis, episcleritis, chorioretinal inflammation, diabetic retinopathy, macular oedema, retinopathy of prematurity, and optic neuritis, eye trauma and recovery from eye injury, trauma or surgery.

In one form of the invention, the RAGE-related disorder is an endocrine disorder selected from the group: diabetes mellitus, insulin resistance, impaired glucose tolerance and thyroiditis.

The composition may comprise about 1 nM to 1000 nM of each of the desired AON(s) of the invention. Preferably, the composition may comprise about 1 nM to 500 nM, 10 nM to 500 nM, 50 nM to 750 nM, 10 nM to 500 nM, 1 nM to 100 nM, 1 nM to 50 nM, 1 nM to 40 nM, 1 nM to 30 nM, 1 nM to 20 nM, most preferably between 1 nM and 10 nM of each of the AON(s) of the invention.

The composition may comprise about 1 nm, 2 nm, 3 nm, 4 nm, 5 nm, 6 nm, 7 nm, 8 nm, 9 nm, 10 nm, 20 nm, 50 nm, 75 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm or 1000 nm of each of the desired AON(s) of the invention.

The present invention further provides one or more AONs adapted to aid in the prophylactic or therapeutic treatment, prevention or amelioration of symptoms of a disease such as a RAGE expression related disease or pathology in a form suitable for delivery to a patient.

The phrase "pharmaceutically acceptable" refers to molecular entities and compositions that are physiologically tolerable and do not typically produce an allergic or similarly untoward reaction, such as gastric upset and the like, when administered to a patient. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in Martin, *Remington's Pharmaceutical Sciences*, 18th Ed., Mack Publishing Co., Easton, Pa., (1990).

In a more specific form of the invention there are provided pharmaceutical compositions comprising therapeutically effective amounts of one or more AONs of the invention together with pharmaceutically acceptable diluents, preservatives, solubilizers, emulsifiers, adjuvants, and/or carriers. Such compositions include diluents of various buffer content (e.g. Tris-HCl, acetate, phosphate), pH and ionic strength and additives such as detergents and solubilizing agents (e.g. Tween 80, Polysorbate 80), anti-oxidants (e.g., ascorbic acid, sodium metabisulfite), preservatives (e.g. Thimersol, benzyl alcohol) and bulking substances (e.g., lactose, mannitol). The material may be incorporated into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, for example, Martin, *Remington's Pharmaceutical Sciences*, 18th Ed. (1990, Mack Publishing Co., Easton, Pa. 18042) pages 1435-1712 that are herein incorporated by reference. The compositions may be prepared in liquid form, or may be in dried powder, such as a lyophilised form.

It will be appreciated that pharmaceutical compositions provided according to the present invention may be administered by any means known in the art. Preferably, the pharmaceutical compositions for administration are administered by injection, orally, topically or by the pulmonary or nasal route. The appropriate route may be determined by one of skill in the art, as appropriate to the condition of the subject under treatment.

In certain embodiments, the AONs of the disclosure can be delivered by pulmonary or nasal routes (e.g., via nebulised saline incorporating the AONs). The highest endogenous expression of RAGE mRNA in the healthy human tissues is found in the lung and is accessible via the airways. Inhaled oligonucleotides are an emerging therapeutic modality for respiratory diseases. The airways are uniquely lined with pulmonary surfactants, which are primarily composed of zwitterionic lipids. These surfactant lipids possess cationic properties at the pH of the respiratory tract. When anionic oligonucleotides are inhaled, they tend to be adsorbed by the surfactants, resulting in reformulated particles that have been hypothesised to be efficiently taken up by bronchial and alveolar epithelial cells into the pulmonary cells. Of note, AONs have been shown to be able to withstand the nebulization process.

In certain embodiments, the AONs are more preferably delivered by intravenous, intra-arterial, intraperitoneal, intramuscular or subcutaneous routes of administration. Vascular or extravascular circulation, the blood or lymph system, and the cerebrospinal fluid are some non-limiting sites where the AON may be introduced.

In certain embodiments, direct CNS delivery may be employed, for instance, intracerebral ventribular or intrathecal administration may be used as routes of administration.

Formulations for topical administration include those in which the oligomers of the disclosure are in admixture with a topical delivery agent such as lipids, liposomes, fatty acids, fatty acid esters, steroids, chelating agents and surfactants. Lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). For topical or other administration, oligomers of the disclosure may be encapsulated within liposomes or may form complexes thereto, in particular to cationic liposomes. Alternatively, oligomers may be complexed to lipids, in particular to cationic lipids. Fatty acids and esters, pharmaceutically acceptable salts thereof, and their uses are further described in U.S. Pat. No. 6,287,860 and/or U.S. patent application Ser. No. 09/315,298 filed on May 20, 1999.

In certain embodiments, the AONs of the disclosure can be delivered by transdermal methods (e.g., via incorporation of the AONs into, e.g., emulsions, with such AONs optionally packaged into liposomes). Such transdermal and emulsion/liposome-mediated methods of delivery are described for delivery of AONs in the art, e.g., in U.S. Pat. No. 6,965,025.

The AONs described herein may also be delivered via an implantable device. Design of such a device is an art-recognized process, with, e.g., synthetic implant design described in, e.g., U.S. Pat. No. 6,969,400.

Compositions and formulations for oral administration include powders or granules, microparticulates, nanoparticulates, suspensions or solutions in water or non-aqueous media, capsules, gel capsules, sachets, tablets or minitablets. Thickeners, flavouring agents, diluents, emulsifiers, dispersing aids or binders may be desirable. Oral formulations are those in which oligomers of the disclosure are administered in conjunction with one or more penetration enhancers surfactants and chelators. Surfactants include fatty acids and/or esters or salts thereof, bile acids and/or salts thereof. Bile acids/salts and fatty acids and their uses are further described in U.S. Pat. No. 6,287,860. In some embodiments, the present disclosure provides combinations of penetration enhancers, for example, fatty acids/salts in combination with bile acids/salts. An exemplary combination is the sodium salt of lauric acid, capric acid and UDCA. Further penetration enhancers include polyoxyethylene-9-lauryl ether, polyoxyethylene-20-cetyl ether. Oligomers of the disclosure may be delivered orally, in granular form including sprayed dried particles, or complexed to form micro or nanoparticles. Oligomer complexing agents and their uses are further described in U.S. Pat. No. 6,287,860. Oral formulations for oligomers and their preparation are described in detail in U.S. Pat. No. 6,887,906, Ser. No. 09/315,298 filed May 20, 1999 and/or US20030027780.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

The delivery of a therapeutically useful amount of AONs may be achieved by methods previously published. For example, intracellular delivery of the AON may be via a composition comprising an admixture of the AON and an effective amount of a block copolymer. An example of this method is described in US patent application US20040248833. Other methods of delivery of AONs to the nucleus are described in Mann C J et al. (2001) Proc, Natl. Acad. Science, 98(1) 42-47, and in Gebski et al. (2003) Human Molecular Genetics, 12(15): 1801-1811. A method for introducing a nucleic acid molecule into a cell by way of an expression vector either as naked DNA or complexed to lipid carriers, is described in U.S. Pat. No. 6,806,084.

It may be desirable to deliver the AON in a colloidal dispersion system. Colloidal dispersion systems include macromolecule complexes, nanocapsules, microspheres, beads, and lipid-based systems including oil-in-water emulsions, micelles, mixed micelles, and liposomes or liposome formulations. These colloidal dispersion systems can be used in the manufacture of therapeutic pharmaceutical compositions.

Liposomes are artificial membrane vesicles, which are useful as delivery vehicles in vitro and in vivo. These formulations may have net cationic, anionic, or neutral charge characteristics and have useful characteristics for in vitro, in vivo and ex vivo delivery methods. It has been shown that large unilamellar vesicles can encapsulate a substantial percentage of an aqueous buffer containing large macromolecules. RNA and DNA can be encapsulated within the aqueous interior and be delivered to cells in a biologically active form (Fraley, et al., Trends Biochem. Sci. 6:77, 1981).

In order for a liposome to be an efficient gene transfer vehicle, the following characteristics should be present: (1) encapsulation of the AON of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988). The composition of the liposome is usually a combination of phospholipids, particularly high phase-transition-temperature phospholipids, usually in combination with steroids, especially cholesterol. Other phospholipids or other lipids may also be used. The physical characteristics of liposomes depend on pH, ionic strength, and the presence of divalent cations. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is a derivative with one or more hydrophilic polymers, such as a polyethylene glycol (PEG) moiety. Liposomes and their uses are further described in U.S. Pat. No. 6,287,860.

The AONs described herein may also be delivered via an implantable device. Design of such a device is an art-recognized process, with, e.g., synthetic implant design described in, e.g., U.S. Pat. No. 6,969,400, the contents of which are incorporated in their entirety by reference herein.

Antisense oligonucleotides can be introduced into cells using art-recognized techniques (e.g., transfection, electroporation, fusion, liposomes, colloidal polymeric particles and viral and non-viral vectors as well as other means known in the art). The method of delivery selected will depend at least on the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

As known in the art, AONs may be delivered using, for example, methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49, incorporated by reference in its entirety).

The AON may also be combined with other pharmaceutically acceptable carriers or diluents to produce a pharmaceutical composition. Suitable carriers and diluents include isotonic saline solutions, for example phosphate-buffered saline. The composition may be formulated for parenteral, intramuscular, intravenous, subcutaneous, intraocular, oral, or transdermal administration.

The routes of administration described are intended only as a guide since a skilled practitioner will be able to readily determine the optimum route of administration and any dosage for any particular animal and condition.

Multiple approaches for introducing functional new genetic material into cells, both in vitro and in vivo have been attempted (Friedmann (1989) Science, 244:1275-1280). These approaches include integration of the gene to be expressed into modified retroviruses (Friedmann (1989) supra; Rosenberg (1991) Cancer Research 51(18), suppl.: 5074S-5079S); integration into non-retrovirus vectors (Rosenfeld, et al. (1992) Cell, 68:143-155; Rosenfeld, et al. (1991) Science, 252:431-434); or delivery of a transgene linked to a heterologous promoter-enhancer element via liposomes (Friedmann (1989), supra; Brigham, et al. (1989) Am. J. Med. Sci., 298:278-311; Nabel, et al. (1990) Science, 249:1285-1288; Hazinski, et al. (1991) Am. J. Resp. Cell Molec. Biol., 4:206-209; and Wang and Huang (1987) Proc. Natl. Acad. Sci. (USA), 84:7851-7855); coupled to ligand-specific, cation-based transport systems (Wu and Wu (1988) J. Biol. Chem., 263:14621-14624) or the use of naked DNA, expression vectors (Nabel et al. (1990), supra); Wolff et al. (1990) Science, 247:1465-1468). Direct injection of transgenes into tissue produces only localized expression (Rosenfeld (1992) supra; Rosenfeld et al. (1991) supra; Brigham et al. (1989) supra; Nabel (1990) supra; and Hazinski et al. (1991) supra). The Brigham et al. group (Am. J. Med. Sci. (1989) 298:278-311 and Clinical Research (1991) 39 (abstract)) have reported in vivo transfection only of lungs of mice following either intravenous or intratracheal administration of a DNA liposome complex. An example of a review article of human gene therapy procedures is: Anderson, Science (1992) 256:808-813; Barteau et al. (2008), Curr Gene Ther; 8(5):313-23; Mueller et al. (2008). Clin Rev Allergy Immunol; 35(3):164-78; Li et al. (2006) Gene Ther., 13(18):1313-9; Simoes et al. (2005) Expert Opin Drug Deliv; 2(2):237-54.

The AONs of the invention encompass any pharmaceutically acceptable salts, esters, or salts of such esters, or any other compound which, upon administration to an animal including a human, is capable of providing (directly or indirectly) the biologically active metabolite or residue thereof. Accordingly, as an example, the disclosure is also drawn to prodrugs and pharmaceutically acceptable salts of the compounds of the invention, pharmaceutically acceptable salts of such pro-drugs, and other bioequivalents.

The term "pharmaceutically acceptable salts" refers to physiologically and pharmaceutically acceptable salts of the compounds of the invention: i.e. salts that retain the desired biological activity of the parent compound and do not impart undesired toxicological effects thereto. For oligomers, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. The pharmaceutical compositions of the present invention may be administered in a number of ways depending upon whether local or systemic treatment is desired and upon the area to be treated. Administration may be topical (including ophthalmic and mucous membranes, as well as rectal delivery), pulmonary, e.g., by inhalation or insufflation of powders or aerosols (including by nebulizer, intratracheal, intranasal, epidermal and transdermal), oral or parenteral. Parenteral administration includes intravenous, intra-arterial, subcutaneous, intraperitoneal or intramuscular injection or infusion; or intracranial, e.g., intrathecal or intraventricular, administration. Oligomers with at least one 2'-O-methoxyethyl modification are believed to be particularly useful for oral administration. Preferably, the AON is delivered via the subcutaneous or intravenous route.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

In one embodiment, the AON is administered in an amount and manner effective to result in a peak blood concentration of at least 200-400 nM AON. Typically, one or more doses of AON are administered, generally at regular intervals, for a period of about one to two weeks. Preferred doses for oral administration are from about 1 mg to 1000 mg oligomer per 70 kg. In some cases, doses of greater than 1000 mg oligomer/patient may be necessary. For i.v. administration, preferred doses are from about 0.5 mg to 1000 mg oligomer per 70 kg. For intra venous or sub cutaneous administration, the AON may be administered at a dosage of about 120 mg/kg daily or weekly.

The AON may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on EC50s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligomer is administered in maintenance doses, ranging from 0.01 µg to 100 g per kg of body weight, once or more daily, to once every 20 years.

An effective in vivo treatment regimen using the AONs of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of disorder under treatment, and corresponding adjustments in the dose or treatment regimen, in order to achieve an optimal therapeutic outcome.

Treatment may be monitored, e.g., by general indicators of disease known in the art. The efficacy of an in vivo administered AONs of the invention may be determined from biological samples (tissue, blood, urine etc.) taken from a subject prior to, during and subsequent to administration of the AON. Assays of such samples include (1) monitoring the presence or absence of heteroduplex formation with target and non-target sequences, using procedures known to those skilled in the art, e.g., an electrophoretic gel mobility assay; (2) monitoring the amount of a mutant mRNA in relation to a reference normal mRNA or protein as determined by standard techniques such as RT-PCR, Northern blotting, ELISA or Western blotting.

Intranuclear oligomer delivery is a major challenge for AONs. Different cell-penetrating peptides (CPP) localize PMOs to varying degrees in different conditions and cell lines, and novel CPPs have been evaluated by the inventors for their ability to deliver PMOs to the target cells. The terms CPP or "a peptide moiety which enhances cellular uptake" are used interchangeably and refer to cationic cell penetrating peptides, also called "transport peptides", "carrier peptides", or "peptide transduction domains". The peptides, as shown herein, have the capability of inducing cell penetration within about or at least about 30%, 40%, 50%, 60%, 70%, 80%, 90%, or 100% of cells of a given cell culture population and allow macromolecular translocation within multiple tissues in vivo upon systemic administration. CPPs are well-known in the art and are disclosed, for example in U.S. Application No. 2010/0016215, which is incorporated by reference in its entirety.

The present invention therefore provides AONs of the present invention win combination with cell-penetrating peptides for manufacturing therapeutic pharmaceutical compositions.

According to a still further aspect of the invention, there is provided one or more AONs as described herein for use in an AON-based therapy. Preferably, the therapy is for a condition related to RAGE expression. More preferably, the therapy for a condition related to RAGE expression is therapy for a disease chosen from: cancer, neurodegenerative diseases, lung disorders, and inflammatory diseases.

More specifically, the AON may be selected from the group consisting of any one or more of the AONs listed in any of Tables 3a-3d and/or SEQ ID NOs: 1-31, and combinations or cocktails thereof. More preferably, the AON is SEQ ID NO: 11, 18, 19, or 20. This includes sequences which can hybridise to such sequences under stringent hybridisation conditions, sequences complementary thereto, sequences containing modified bases, modified backbones, and functional truncations or extensions thereof which possess or modulate pre-mRNA processing activity in a RAGE gene transcript.

The invention extends also to a combination of two or more AONs capable of binding to a selected target to induce exon exclusion in a RAGE gene transcript. The combination may be a cocktail of two or more AONs, a construct comprising two or more or two or more AONs joined together for use in an AON-based therapy. The combination of AONs is preferably a combination of SEQ ID NO: 11 and 10, or SEQ ID NO: 11 and 13.

The invention provides a method to treat, prevent or ameliorate the effects of a disease associated with RAGE expression, comprising the step of:
  a) administering to the patient an effective amount of one or more AONs or pharmaceutical composition comprising one or more AONs as described herein.

Furthermore, the invention provides a method to treat, prevent or ameliorate the effects of cancer, neurodegenerative diseases, lung disorders, and inflammatory diseases comprising the step of:
  a) administering to the patient an effective amount of one or more AONs or pharmaceutical composition comprising one or more AONs as described herein.

Preferably, the therapy is used to reduce the levels of functional RAGE protein via an exon skipping strategy. The reduction in levels of RAGE is preferably achieved by reducing the transcripts level through modifying pre-mRNA splicing in the RAGE gene transcript or part thereof.

The reduction in RAGE will preferably lead to a reduction in the quantity, duration or severity of the symptoms of a RAGE-related condition or pathology, such as neurodegenerative diseases, cancer, lung disorders, and inflammatory diseases.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment"

or "prophylaxis" does not necessarily indicate complete eradication, cure, or prevention of the disease or condition, or associated symptoms thereof.

According to another aspect of the invention there is provided the use of one or more AONs as described herein in the manufacture of a medicament for the modulation or control of a disease associated with RAGE expression.

The invention also provides for the use of purified and isolated AONs as described herein, for the manufacture of a medicament for treatment of a disease associated with RAGE expression.

There is provided the use of purified and isolated AONs as described herein for the manufacture of a medicament to treat, prevent or ameliorate the effects of a disease associated with RAGE expression.

Preferably, the RAGE-related pathology or disease is neurodegenerative diseases, cancer, lung disorders, or inflammatory diseases.

The invention extends, according to a still further aspect thereof, to cDNA or cloned copies of the AON sequences of the invention, as well as to vectors containing the AON sequences of the invention. The invention extends further also to cells containing such sequences and/or vectors.

The AON of the present invention may be co-adminstered with another therapeutic molecule. For example, the AON may be administered with a second therapeutic agent that is a compound, such as a peptide, that is able to modulate the RAGE cytosolic tail. Such compounds include: IQGAP-1, diaphanous-1, protein kinase C zeta (PKCζ), Dock7, MyD88, TIRAP, ERK1/2, olfactory receptor 2T2, ADP/ATP translocase 2, Protein phosphatase 1G, IRAK4, Protein DJ-1 (PARK7), Calponin-3, Drebrin, Filamin B, Ras-related protein Rab-13, Radixin/Ezrin/Moesin, Proteolipid protein 2, Coronin, S100 A11, Succinyl-CoA ligase [GDP-forming] subunit alpha, Hsc70-interacting protein, Apoptosis Inhibitor 5, neuropilin, cleavage stimulation factor, growth factor receptor-bound protein 2, sec61 beta subunit, or Nck1.

The invention also provides kits to treat, prevent or ameliorate a disease or condition associated with RAGE expression in a patient, which kit comprises at least an isolated or purified AON for modifying pre-mRNA splicing in a RAGE gene transcript or part thereof, packaged in a suitable container, together with instructions for its use.

In a preferred embodiment, the kits will contain at least one AON as described herein, any one or more of SEQ ID NOs: 1-31 and/or the sequences set forth in any of Tables 3a-3d, or a cocktail of AONs, as described herein. The kits may also contain peripheral reagents such as buffers, stabilizers, etc. More preferably, the AON is SEQ ID NO: 11, 18, 19, or 20.

There is therefore provided a kit to treat, prevent or ameliorate a disease or condition associated with RAGE expression in a patient, which kit comprises at least an AON described herein, any one or more of SEQ ID NOs: 1-31 and/or the sequences set forth in any of Tables 3a-3d and combinations or cocktails thereof, packaged in a suitable container, together with instructions for its use. More preferably, the AON is SEQ ID NO: 11, 18, 19, or 20. The combination of AONs is preferably a combination of SEQ ID NO: 11 and 10, or SEQ ID NO: 11 and 13.

Preferably, the disease or condition is chosen from the list comprising: cancer, neurodegenerative diseases, lung disorders, or inflammatory diseases.

The contents of the kit can be lyophilized and the kit can additionally contain a suitable solvent for reconstitution of the lyophilized components. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale for human administration.

When the components of the kit are provided in one or more liquid solutions, the liquid solution can be an aqueous solution, for example a sterile aqueous solution. For in vivo use, the expression construct may be formulated into a pharmaceutically acceptable syringeable composition. In this case the container means may itself be an inhalant, syringe, pipette, eye dropper, or other such like apparatus, from which the formulation may be applied to an affected area of the animal, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle.

Those of ordinary skill in the field should appreciate that applications of the above method has wide application for identifying AONs suitable for use in the treatment of many other diseases.

The AONs of the present invention may also be used in conjunction with alternative therapies, such as drug therapies.

The present invention therefore provides a method of treating, preventing or ameliorating the effects of a disease or condition associated with RAGE expression, wherein the AONs of the present invention and administered sequentially or concurrently with another alternative therapy associated with treating, preventing or ameliorating the effects of a disease or condition associated with RAGE expression. Preferably, the disease or condition is chosen from the list comprising: neurodegenerative diseases, cancer, lung disorders, or inflammatory diseases.

General

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

As used herein the term "derived" and "derived from" shall be taken to indicate that a specific integer may be obtained from a particular source albeit not necessarily directly from that source.

As used herein, the singular forms "a," "an" and "the" include plural references unless the context clearly dictates otherwise.

Throughout this specification, unless the context requires otherwise, the word "comprise", or variations such as "comprises" or "comprising", will be understood to imply the inclusion of a stated integer or group of integers but not the exclusion of any other integer or group of integers.

Other than in the operating example, or where otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the specification and claims are approximations that may vary depending upon the desired properties sought to be obtained by the present invention. Hence "about 80%" means "about 80%" and also "80%". At the very least, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value; however, inherently contains certain errors necessarily resulting from the standard deviation found in their respective testing measurements Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Sequence identity numbers ("SEQ ID NO:") containing nucleotide and amino acid sequence information included in this specification are collected at the end of the description and have been prepared using the program Patent In Version 3.0. Each nucleotide or amino acid sequence is identified in the sequence listing by the numeric indicator <210> followed by the sequence identifier (e.g. <210>1, <210>2, etc.). The length, type of sequence and source organism for each nucleotide or amino acid sequence are indicated by information provided in the numeric indicator fields <211>, <212> and <213>, respectively.

An antisense oligomer nomenclature system was proposed and published to distinguish between the different antisense oligomers (see Mann et al., (2002) J Gen Med 4, 644-654). This nomenclature became especially relevant when testing several slightly different antisense oligomers, all directed at the same target region, as shown below:

H #A/D (x:y)
the first letter designates the species (e.g. H: human, M: murine)
"#" designates target exon number
"A/D" indicates acceptor or donor splice site at the beginning/end of the exon, respectively
(x y) represents the annealing coordinates where "−" or "+" indicate intronic or exonic sequences respectively. As an example, A(−6+18) would indicate the last 6 bases of the intron preceding the target exon and the first 18 bases of the target exon. The closest splice site would be the acceptor so these coordinates would be preceded with an "A". Describing annealing coordinates at the donor splice site could be D(+2−18) where the last 2 exonic bases and the first 18 intronic bases correspond to the annealing site of the antisense oligomer. Entirely exonic annealing coordinates that would be represented by A(+65+85), that is the site between the 65th and 85th nucleotide, inclusive, from the start of that exon.

The following examples more fully describe the manner of using the above-described invention, as well as to set forth the best modes for carrying out various aspects of the invention. It is understood that these methods do not limit the scope of this invention, but rather are presented for illustrative purposes.

EXAMPLES

In each of the following examples, the following general materials and methods apply, unless the context requires otherwise.

Human microvascular endothelial cells (HMEC1) were cultured in MCDB 131 medium (10% FCS with 10 mM glutamine, EGF and hydrocortisone). Human lung epithelial cells (A549) (carcinoma) were cultured in F-12K medium (10% FBS with 2 mM glutamine). Primary aortic endothelial cells (PMAEC) were isolated from the aortae of (wild-type) C57bl6 mice and AGER KO mice and cultured in Dulbecco's modified Eagle's medium (DMEM)/F12 endothelial cell growth supplement (ECGS) supplemented media.

For transfection with AONs, epithelial or endothelial cells were seeded into 48-well plates for 24 or 48-hours and then transfected using lipofectamine 3000 reagent (0.15 ul/well of lipofectamine 3000; 0.4 ul/well P3000/well) with either AONs targeting exon 9 of the human AGER (for HMEC1 and A549) and murine AGER for mouse PMAEC cells or respective controls (Tables 3a-3d). Cells were incubated with AON/cationic lipoplexes at 37° C. for 24 hrs after which time, cells were lysed, RNA extracted and cDNA generated using either the TRIZOL technique or Cells to CT method.

To measure the effect on alternative splicing of human RAGE pre-mRNA, expression was determined using real-time RT-PCR primers to either the 11th exon, exon 9b or spanning exons 8-10 of RAGE, denoting expression (mRNA) retained in all RAGE mRNA splice variants, retention of exon 9b or expression of the RAGEv1 isoform encoding the transmembrane-cytosolic tail, respectively. A reduction in the PCR signal of exon 8-10 of the cytosolic tail relative to exon 11 indicates that less fewer RAGE mRNA splicoforms contain exon 10 and less full-length RAGE protein isoforms (signalling capable) is produced by the cell. In murine cells and tissues, primers spanning exon 10-11 of murine RAGE mRNA were used to denote the expression of RAGE mRNA splicoforms containing exon 10.

Media was also collected and levels of soluble RAGE determined by ELISA. Media (6 ml) was concentrated using a molecular weight cut off filter prior to testing by ELISA.

Chinese Hamster Ovary (CHO) cell express recombinant proteins in high levels making them an ideal system to interrogate the regulation of pre-mRNA splicing with altered protein secretion as the endpoint. As a model system to better explore the effect of AONs on the splicing of RAGE leading to the expression and secretion of extracellular soluble RAGE, CHO cells grown in F12 media (supplemented with 10% FBS) were transfected with a plasmid encoding the Human genomic AGER (gRAGE) sequence (excluding the native 5' and 3' untranslated regions) along with AONs using Lipofectamine 2000. After 2 days the media was collected, concentrated using a molecular weight cut off filter and examined by western blot using anti-hRAGE antibody (R&D systems).

To determine the exact sequence of the RAGE variants detected after AON administration, RNA was extracted using the Trizol method and cDNA generated using oligo dT primers before PCR using RAGE specific primers to the 5' and 3'UTR sequences of RAGE and semi-nested PCR to amplify a mixture of RAGE sequences. Gel purified RAGE bands were cloned into TA cloning vectors before transformation into *E. coli* Top10 cells. Greater than 50 colonies were selected for characterisation using MultiNA sequence analyser using primers spanning exons 8-11 to determine the size of the RAGE insert. Five clones of each size were sent for sanger sequencing to confirm the RAGE sequence splicoforms corresponded with band size.

To measure the functional impact of intervention of ligand dependent and ligand independent activation of RAGE, cells were exposed to the AT1R cognate ligand, Ang II (1 µM) or the RAGE ligand, S100A8/A9 (0.6 µg/mL) cells for 4 hours. Cells were then stored frozen until extraction of mRNA extracted and cDNA synthesized using the Cells to Ct method. Changes in the gene expression of the NFκB subunit, p65 (RelA) or NFκB-activated target genes (e.g. ICAM-1) were estimated by quantitative real-time RT-PCR, performed using the TaqMan system based on real-time detection of accumulated fluorescence (ABI Prism 7700, Perkin-Elmer Inc, PE Biosystems, Foster City, Calif. USA). Gene expression was normalized to 18 S mRNA and reported as fold change compared to the level of expression in untreated control mice/cells, which were given an arbitrary value of 1.

Example 1. Modulation of Alternative Splicing of Rage in Humans Cells Using Antisense Oligonucleotides Targeting Cis-Acting RNA Elements in Exon 10

This example demonstrates that the splicing of RAGE pre-mRNA can be modulated using AONs targeting cis-acting RNA elements in exon 10 of RAGE pre-mRNA.

RAGE pre-mRNA is naturally subject to alternative splicing, generating a range of mRNA splicoforms. The majority of these RAGE splicoforms contain both exon 10 and 11, coding for the transmembrane and cytosolic domains of RAGE respectively, and the protein isoforms that are produced are therefore capable of being activated by RAGE ligands and transactivated by a collocated GPCR, to induce pro-inflammatory and pro-proliferative signalling. Alternative 5' splice site selection in exon 9 can also lead to an 83-nucleotide extension of exon 9 (exon 9B; FIG. 1*a*).

Because the distance between this alternative splice site and the 3' (acceptor) splice site at the start of exon 10 is only 46 nucleotides, much shorter than the lower limit of the intron length in eukaryotes, exon 10 is consequently skipped, and the 3' (acceptor) site at the start of exon 11 is selected instead. This alternative splicing also introduces a premature termination codon but is not subject to nonsense mediated decay due to its close (29 bp) proximity to the last exon-exon junction. The mature mRNA resulting from this alternative splicing (RAGE_v1, FIG. 1*a*), therefore codes for a protein isoform that lacks the elements required for membrane retention and cytoplasmic signalling encoded by exon 10 and 11 respectively, so is secreted and naturally found in the circulation, broncho-alvelolar and cerebrospinal fluids. This esRAGE can act as a decoy receptor, competing with cell-surface full-length RAGE for ligands or increasing ligand clearance. The novel 17-amino acid C-terminal encoded by exon 9b may also have independent actions on RAGE signalling or multimerization.

Transfection of Human lung epithelial cells (A549) with 10 nM AONs targeting exon 10, resulted in changes in the expression of RAGE mRNA splicoforms containing exon 9b (FIG. 1*b*). Some AONs, in particular AON 3779, increased the expression of RAGE mRNA splicoforms containing exon 9b compared to the control (scrambled RNA treated) cells, as measured by real time RT-PCR. Other AONs also targeting exon 10, in particular AON 3777 and 3781 had no effect.

Figure 1D:
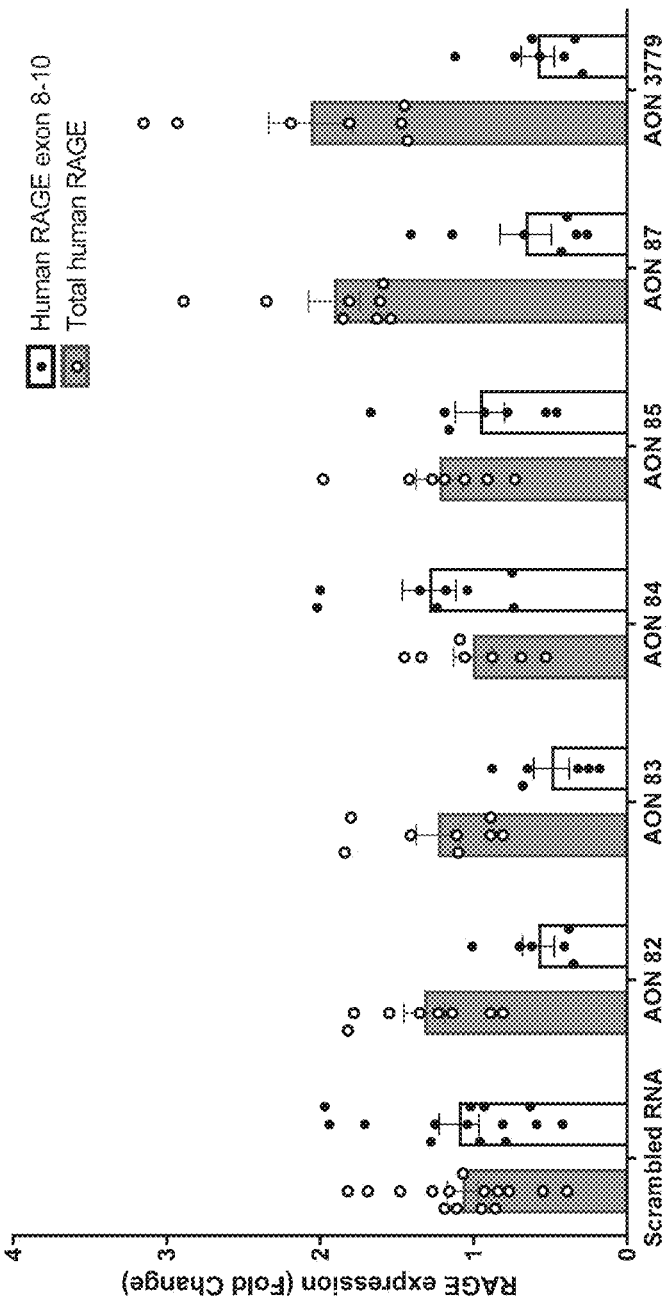
FIG. 1d shows the fold change in mRNA expression of any RAGE (total human RAGE) splicoforms and human RAGE mRNA splicoforms containing exon 10, as detected by real time RT-PCR following treatment of A579 cells with selected AONs also targeting exon 10 adjacent to the putative hnRNPF binding site or control (scrambled RNA treated) cells.

Transfection of Human lung epithelial cells (A549) with 10 nM concentrations AONs targeting exon 10, also resulted in changes in the expression of RAGE mRNA splicoforms such that some AONs, in particular AONs 3779, 3780, 3781, 82, 83 and 87 reduced the expression of RAGE mRNA splicoforms containing exon 10 (i.e. coding for the signalling elements of the cytosolic tail) when compared to the control (scrambled RNA treated) cells, as measured by real time RT-PCR (FIGS. 1*c* & 1*d*). Other AONs also targeting exon 10, in particular AON 3777, 84 and 85, had no effect.

All RAGE mRNA splicoforms expressed in human lung epithelial cells (A549) in the presence and absence of selected AONs targeting exon 10, were then isolated and cloned into *E. coli* Top10 cells. Using primers spanning between exon 8 and exon 11, the size of each RAGE insert was determined. Treatment with selected AONs targeting exon 10, in particular AONs 3779 and 3778, resulted in the increased expression of RAGE mRNA splicoforms containing fragments 250 kB in size (FIG. 1*e*), denoting the retention of exon 9b.

Figure 1F:
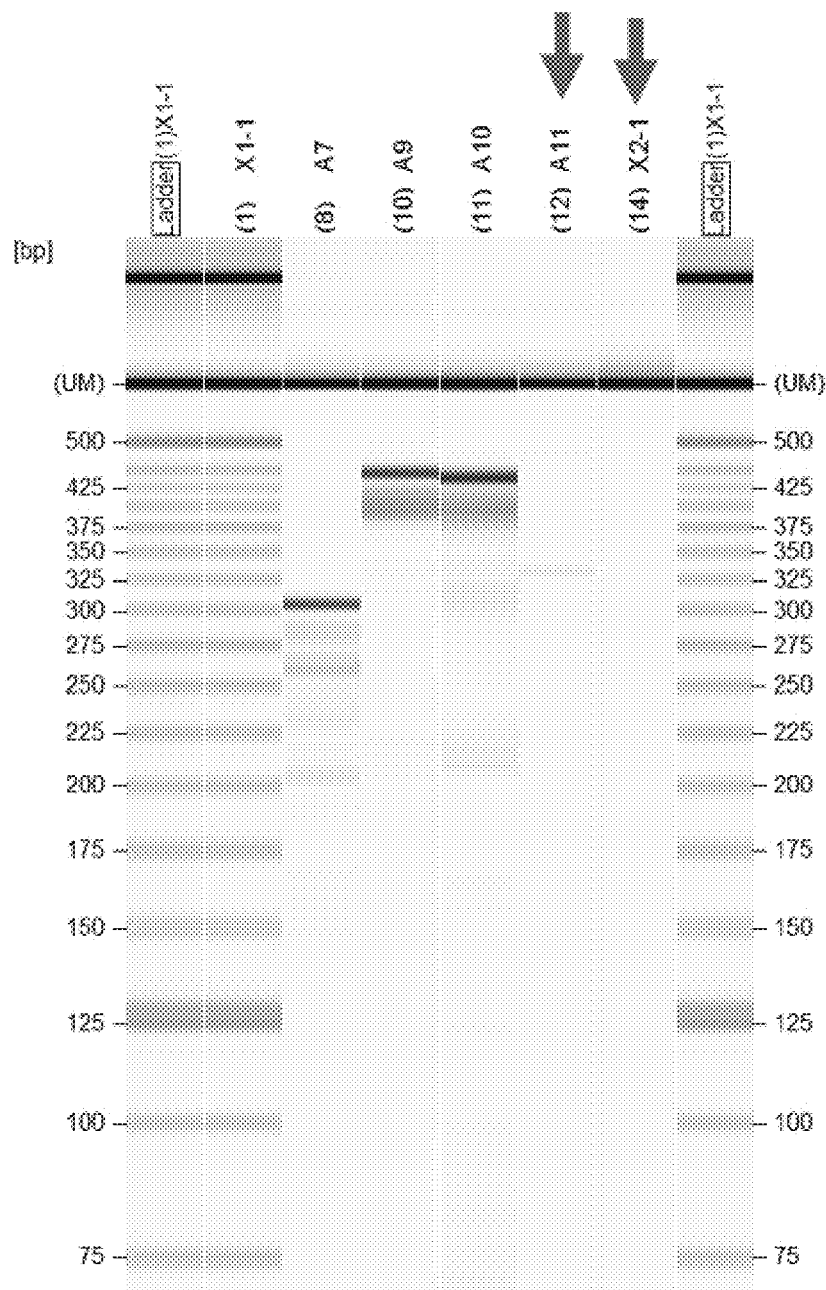
FIG. 1f is a representative gel image of DNA PCR products spanning exon 8-11 with bands of different sizes or no bands (arrows) denoting the presence of different splicoforms.

All AONs targeting exon 10 also reduced the expression of percentage of mRNA clones expressing the 300 kB band, denoting full expression of signalling capable elements contained in exons 8-10. In particular, AON 3779 resulted in a 49% reduction in RAGE mRNA splicoforms containing fragments 300 kB in size (FIG. 1*f*).

All AONs targeting exon 10 also induced the de novo expression of RAGE mRNA splicoforms completely missing exon 8 (confirmed by Sanger sequencing and denoted by empty lane on the MultiNA analyser indicated by the arrows on the gel; FIG. 1*f*) and 'no band' fragment (FIG. 1*e*).

Transfection of Human lung epithelial cells (A549) with AONs targeting exon 10, in particular, AON 3777 and 3778 also resulted in the de novo expression of RAGE mRNA splicoforms containing fragments 276 and 430 kB in size (FIG. 1*e*), denoting the atypical removal of exon 9, and retention of exon 9, 9b and exon 10 respectively.

Figure 1G:
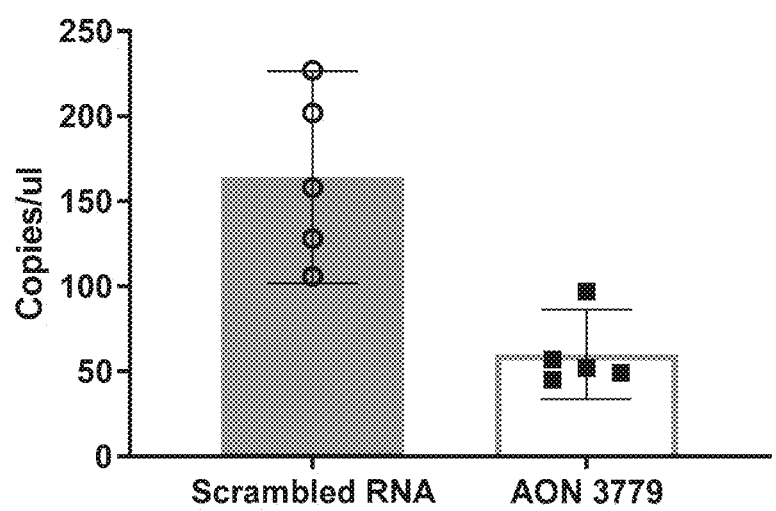
FIG. 1g shows the copy numbers of RAGE mRNA that contain exon 10, as measured by digital PCR, following treatment of A579 cells with AON 3779 compared to control (scrambled RNA treated) cells.

Transfection of Human lung epithelial cells (A549) with 10 nM AONs targeting exon 10, in particular AON 3779, also resulted in changes in the number of copies of the RAGE mRNA splicoforms containing exon 10 than control (scrambled RNA treated) cells, as measured on digital PCR (FIG. 1g).

Transfection of Human lung epithelial cells (A549) with 10 nM AONs targeting exon 10, in particular AON 3779, also increased the release of endogenous soluble RAGE into the media (FIG. 1h), consistent with increased expression of a RAGE mRNA splicoform containing exon 9b.

Figure 1I:
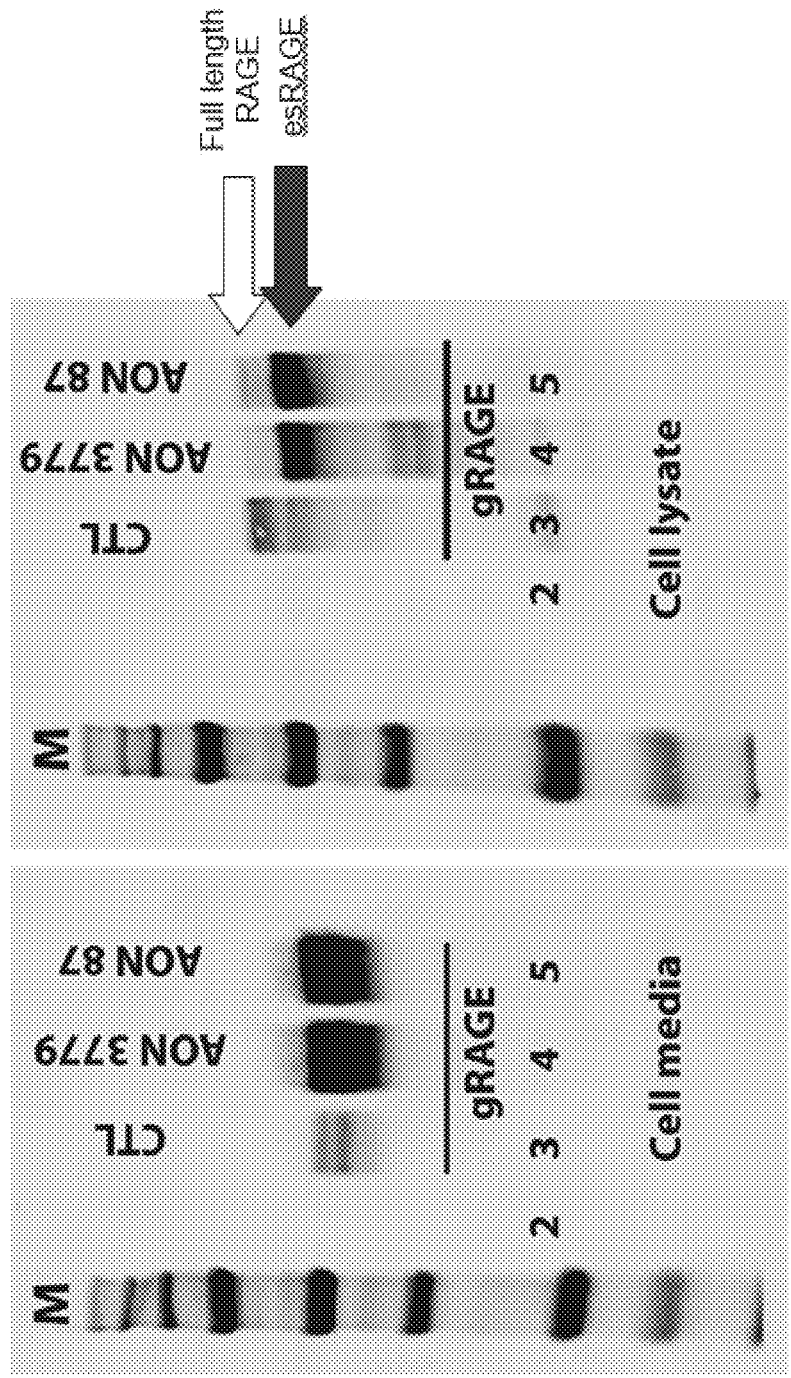
FIG. 1i shows the expression of RAGE protein in the cell media (left) and cell lysate (right) following transfection of CHO cells with DNA coding for the genomic sequence of human RAGE (gRAGE), with and without AON3779 or AON87 or control (CTL) RNA, by western blot detected using a RAGE specific antibody. Lane M is the Marker, lane 2 is the vector control (no endogenous RAGE is expressed), lane 3 is the gRAGE+ control (scrambled) RNA, lane 3 is gRAGE+AON3779, and lane 4 is gRAGE+AON87. Arrows denote the size of smaller soluble RAGE in cell media (red) and larger full-length RAGE in cell lysate (white).

Transfection of CHO cells with a plasmid encoding the genomic sequence of human RAGE (gDNA) resulted in alternative splicing of the gene product, including a small amount of endogenous RAGE secreted into the cell media (red arrow) as detected by Western Blot, consistent with normal splicing pattern of RAGE (FIG. 1i). The amount of endogenous soluble RAGE (esRAGE) secreted into the media was increased when these CHO cells expressing genomic human RAGE were co-transfected with AON 3779 or AON 87 (FIG. 1i). At the same time, full length RAGE expressed and retained in cells (white arrow) was reduced when CHO cells expressing genomic human RAGE were co-transfected with AON 3779 or AON 87. Cells also contained increased amount of C-truncated RAGE intracellularly.

Figure 1J:
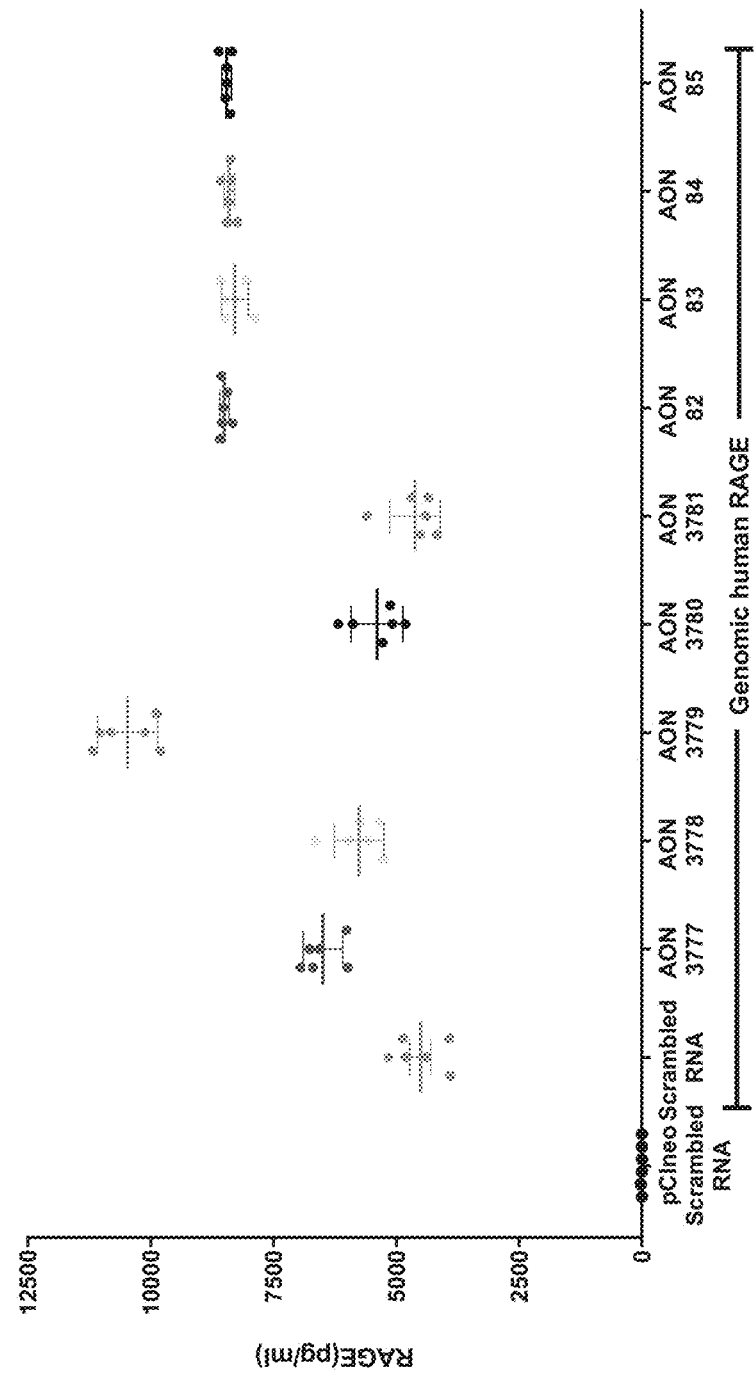
FIG. 1j shows the expression of soluble RAGE protein in the media following transfection of CHO cells with DNA coding for the genomic sequence of human RAGE (gRAGE), with and without transfection with AONs targeting exon 10, as measured by ELISA.

The quantitative amount of soluble RAGE, as measured on ELISA, was also increased in CHO cells expressing genomic human RAGE following transfection with selected AONs targeting exon 10, including AON 3779, AON 82, 83, 84 and 85 (FIG. 1j). Of these, AON 3779 had the greatest effect.

Figure 1L:
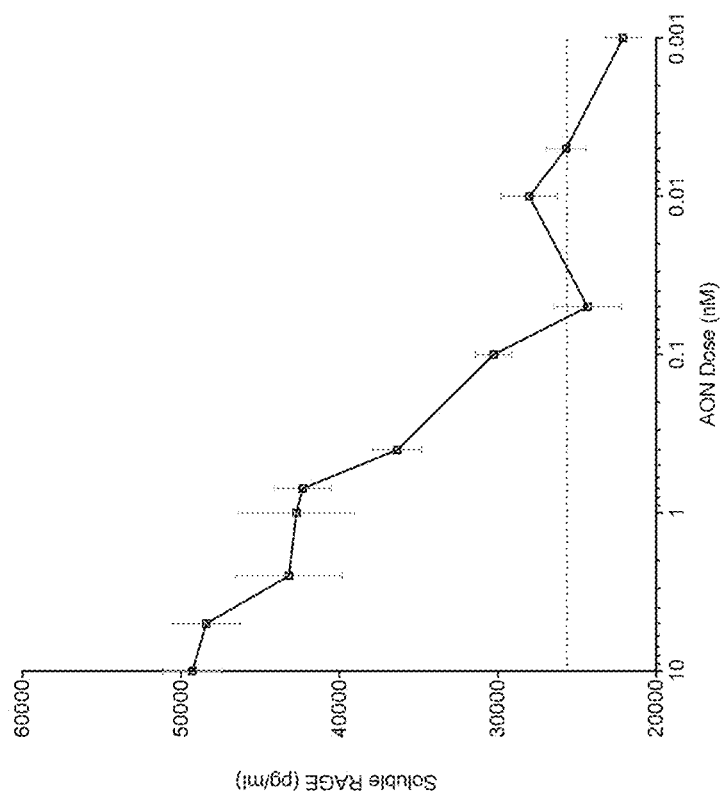
FIG. 1l shows the dose dependent induction of expression of soluble RAGE in the media following transfection of CHO cells with DNA coding for the genomic sequence of human RAGE with and without AON 3779, as measured by ELISA. The dotted line represents the expression of soluble RAGE in CHO cells transfected with scrambled RNA (10 nM).

The quantitative amount of soluble RAGE, as measured on ELISA, was also increased by some other AONs targeting exon 10 in a similar region to AON 3779, including AON 90 and 93 (FIG. 1k), by a similar amount to AON 3779 (10 nM). The quantitative amount of soluble RAGE released from in CHO cells expressing genomic human RAGE was increased following transfection with AON 3779, in a dose dependent manner (FIG. 1l).

Transfection of Human lung epithelial cells (A549) with 10 nM AONs targeting exon 10, in particular AON 3779, also modulated the induction of pro-inflammatory signalling following activation of RAGE with the RAGE-ligand S100A8/A9 (0.6 µg/mL) leading to the induction of ICAM-1 expression (FIG. 1m).

Figure 1N:
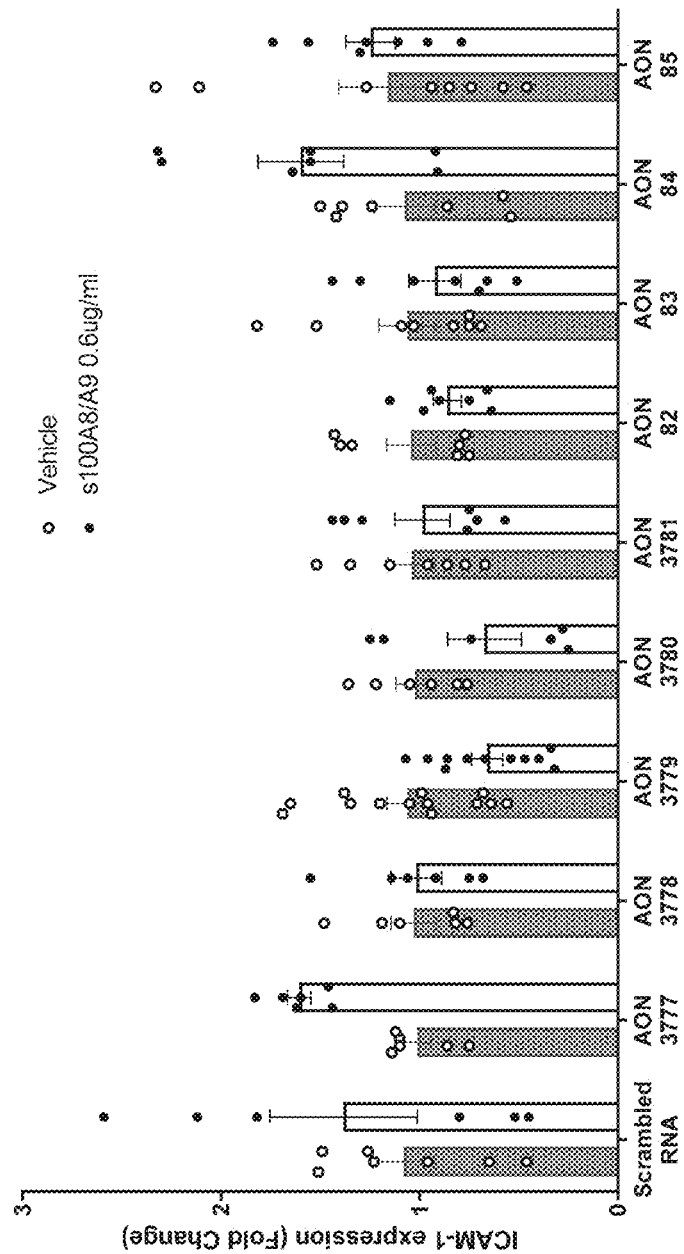
FIG. 1n shows the induction of ICAM-1 gene expression following treatment of primary human aortic endothelial cells (HAEC) cells with the RAGE ligand, S100A8/9 (0.6 µg/ml) and its modulation by pre-transfection with selected AONs targeting exon 10 compared to control (scrambled RNA treated) cells.
Figure 10:
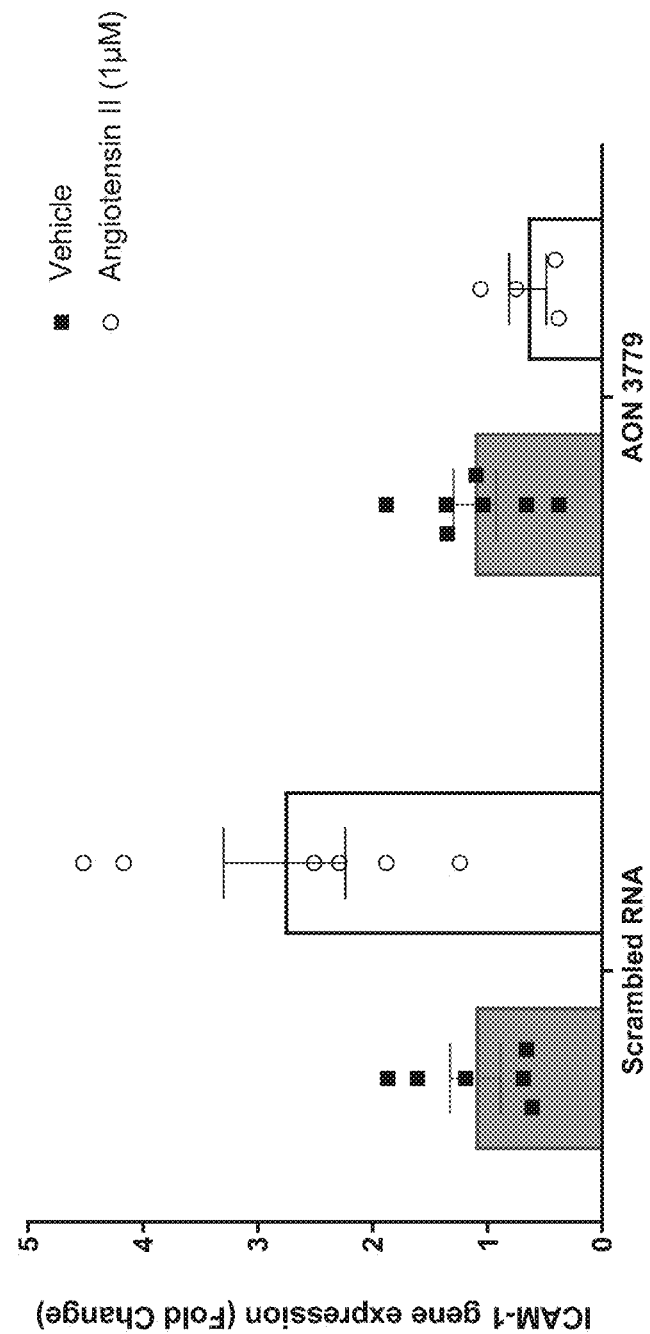

Transfection of human aortic endothelial cells (HAEC) with 10 nM AONs targeting exon 10, in particular AON 3779, 3780, 81, 82 and 83 also prevented the induction of ICAM-1 expression following exposure to the RAGE ligand S100A8/A9 (0.6 µg/mL; FIG. 1n)

Transfection of Human lung epithelial cells (A549) with 10 nM AONs targeting exon 10, in particular AON 3779, also modulated the induction of pro-inflammatory signalling following transactivation of RAGE following activation of AT1 receptor by angiotensin II (1 µM) leading to the induction of ICAM-1 expression (FIG. 1o).

Figure 1P:
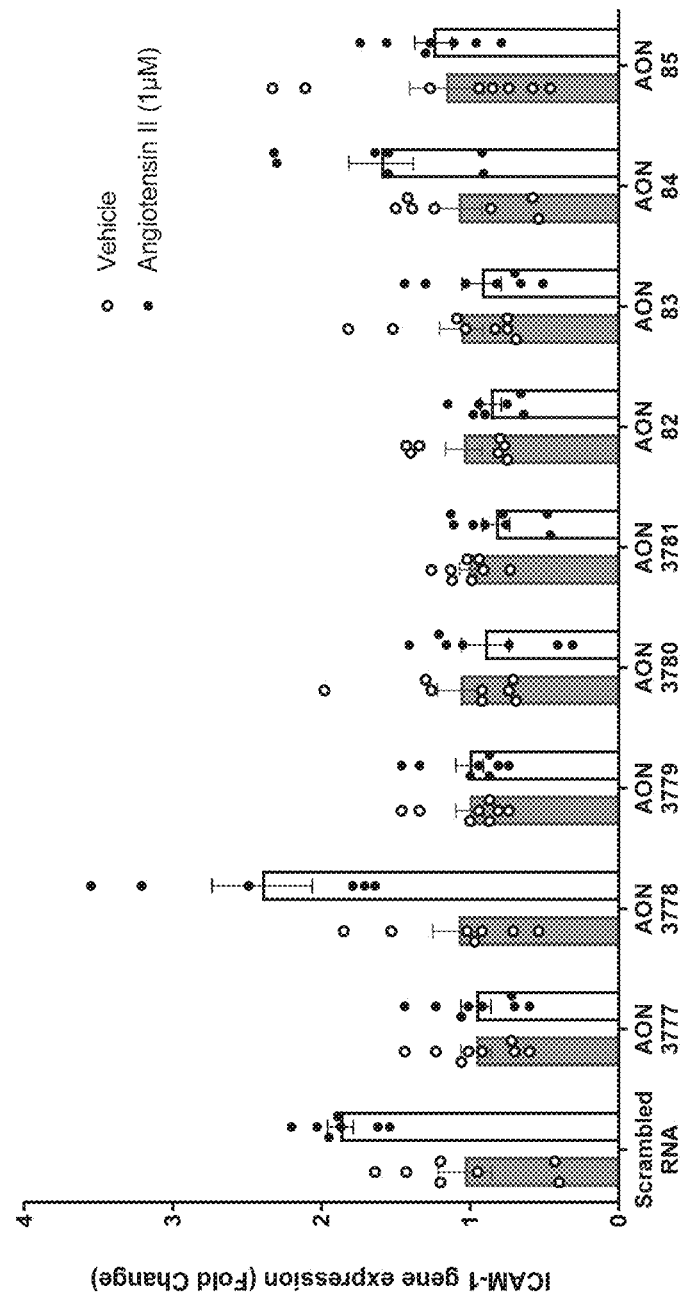
FIG. 1p shows the induction of ICAM-1 gene expression following treatment of primary human aortic endothelial cells (HAEC) with Angiotensin II (1 µM) and its modulation by pre-transfection with selected AONs targeting exon 10 compared to control (scrambled RNA treated) cells.

Transfection of Human aortic endothelial cells (HAEC) with 10 nM AONs targeting exon 10, in particular AONs 3777, 3779, 3780, 3780, 3782 and 3783, also modulated the induction of pro-inflammatory signalling including the induction of ICAM-1 expression following ligand independent transactivation of RAGE following activation of AT1 receptor by angiotensin (1 µM; FIG. 1p). Other AONs targeting exon 10, in particular AON 3778 and 84 had no effect.

Figure 1Q:
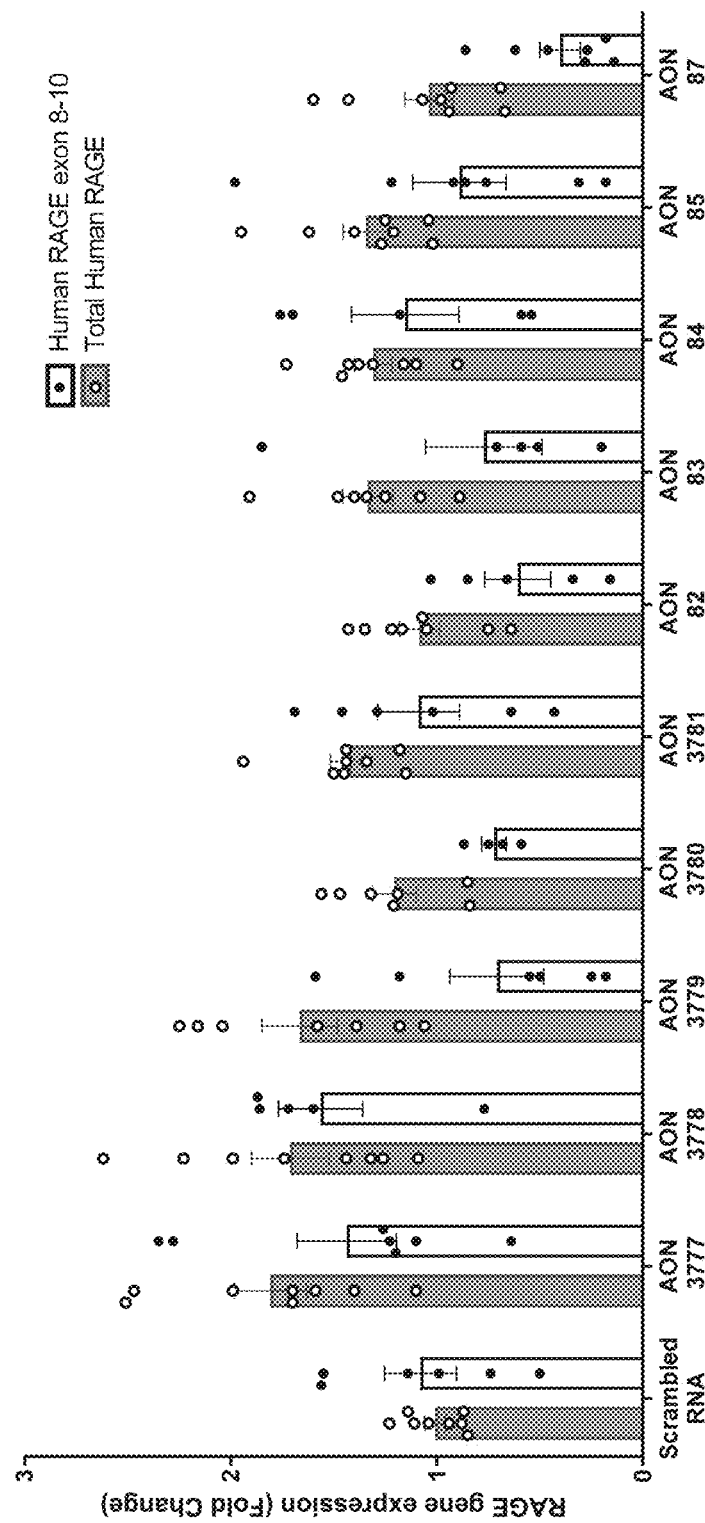
FIG. 1q shows the fold change in expression of any RAGE mRNA (total human RAGE) splicoforms and human RAGE mRNA splicoforms containing exon 10, as detected by real time RT-PCR following treatment of HMEC with AONs specifically targeting exon 10 adjacent to the putative hnRNP-F/H1 binding site or control (scrambled RNA treated) cells.
Figure 1R:
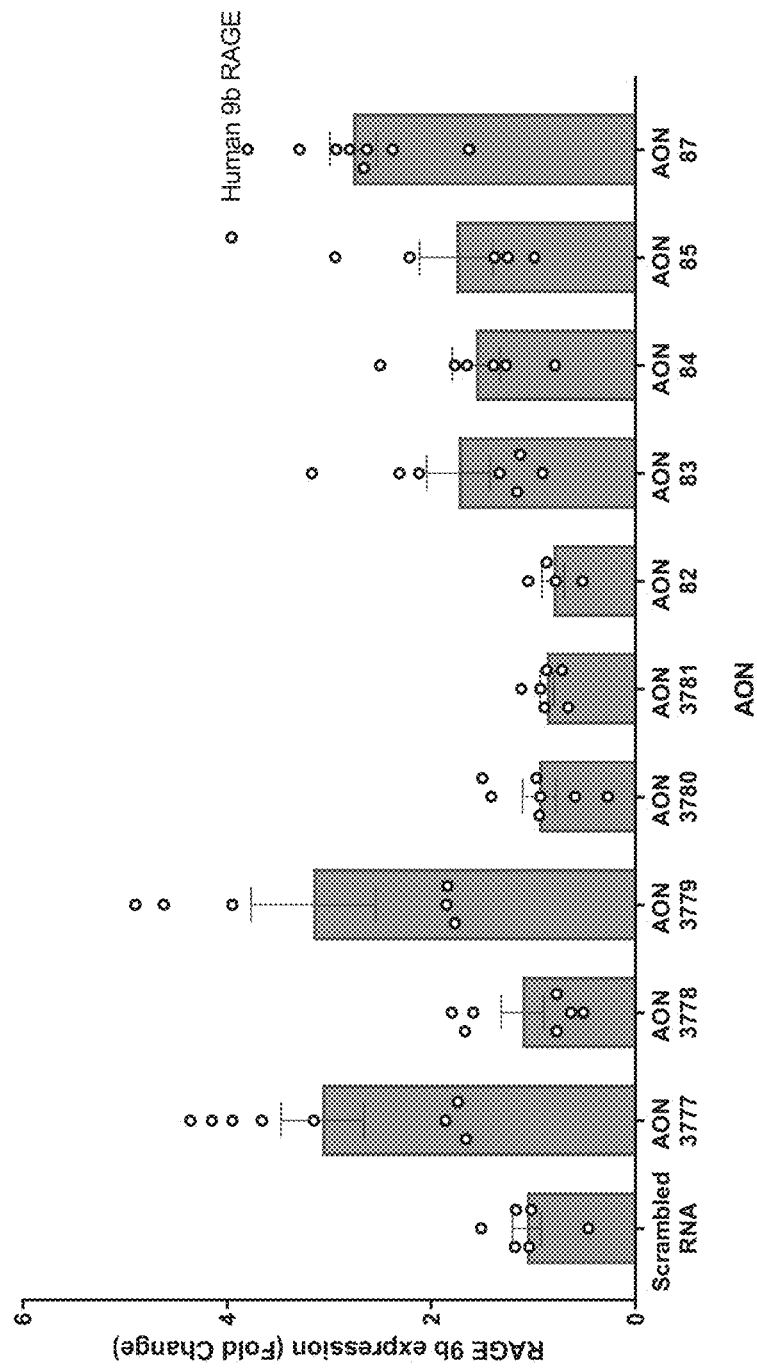
FIG. 1r shows the fold change in mRNA expression of RAGE mRNA splicoforms containing the human RAGE 9b sequence following treatment of HMEC with AONs targeting exon 10 adjacent to the putative hnRNPF binding site or control (scrambled RNA treated) cells.

Transfection of Human microvascular endothelial cells (HMEC1) with 10 nM AONs targeting exon 10, in particular AONs 3779, 3780, 82, 83 and 87, resulted in changes in the expression of RAGE mRNA splicoforms, including a reduction in the expression of RAGE mRNA splicoforms containing exon 10 (FIG. 1q). Transfection of Human microvascular endothelial cells (HMEC1) with 10 nM AONs targeting exon 10, in particular AON 3779 and 87, also induced an increase in the expression of RAGE mRNA splicoforms containing exon 9b, (FIG. 1r).

Figure 1S:
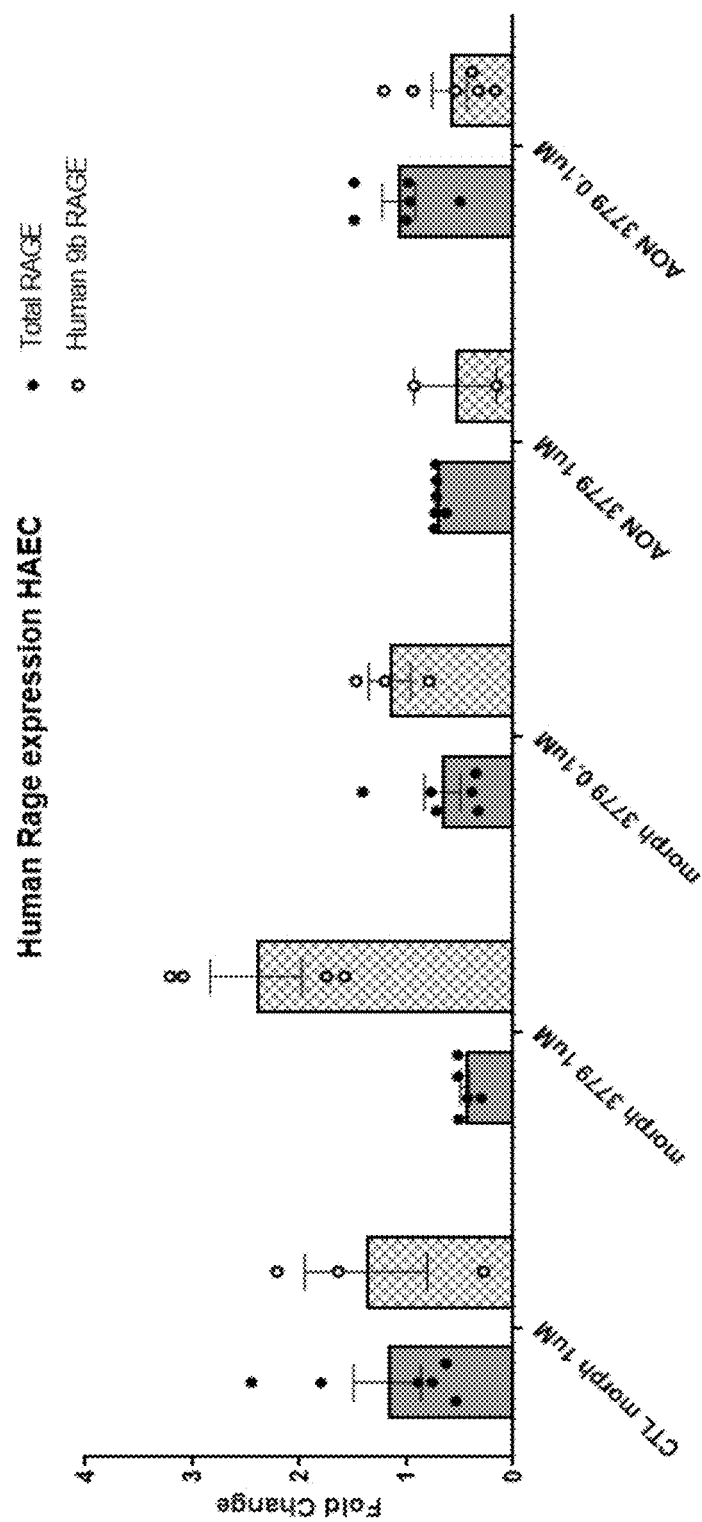
FIG. 1s shows the effect of treatment of primary human aortic endothelial cells (HAEC) with a vivo-morpholino formulation of AON 3779 (0.1-1 µM) on the expression of the RAGE mRNA splicoforms containing exon 9b, compared a non-target morpholino AON control.
Figure 1T:
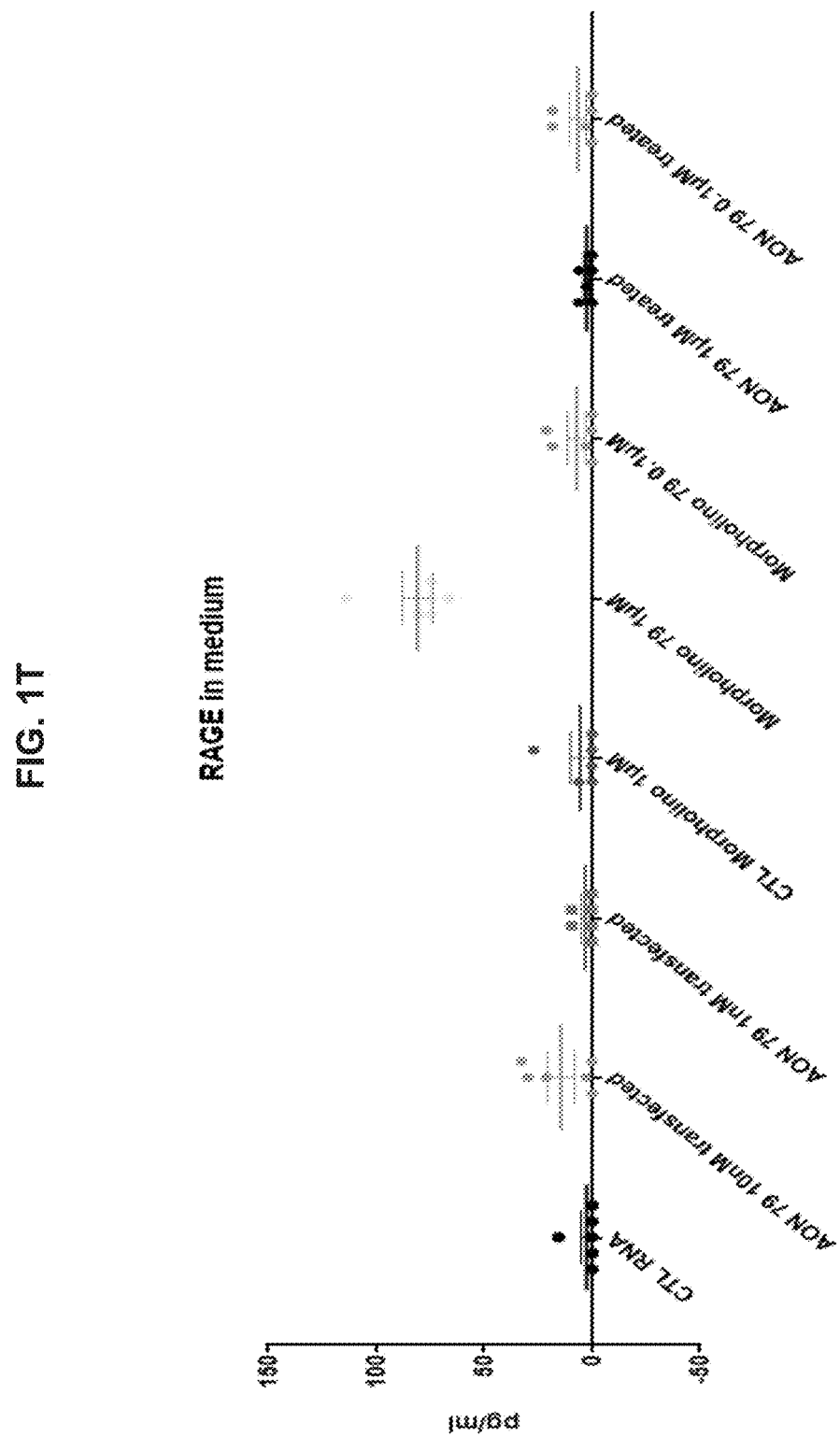
FIG. 1t shows the effect of treatment of primary human aortic endothelial cells (HAEC) with a vivo-morpholino formulation of AON 3779 (0.1-1 µM) on the expression of soluble RAGE protein in the culture medium, compared a non-target morpholino AON control.

Morpholino-oligonucleotides with a covalently linked octa-guanidine dendrimer (known as vivo-morpholinos) can be used in vitro and in vivo without the need for transfection reagents. Treatment of human aortic endothelial cells (HAEC) with an vivo-morpholino formulation of AON 3779 (1 µM) resulted in changes in the expression of RAGE mRNA splicoforms, including an increase in RAGE mRNA splicoforms containing exon 9b, as measured by RT-PCR (FIG. 1s). In addition, the expression of esRAGE in the cell medium was also increased compared to cells treated with a control morpholino AON (FIG. 1t). Treatment with AON 79 without transfection reagents had no effect. Transfection of AON 3779 with transfection reagents is show as the positive control.

Figure 1U:
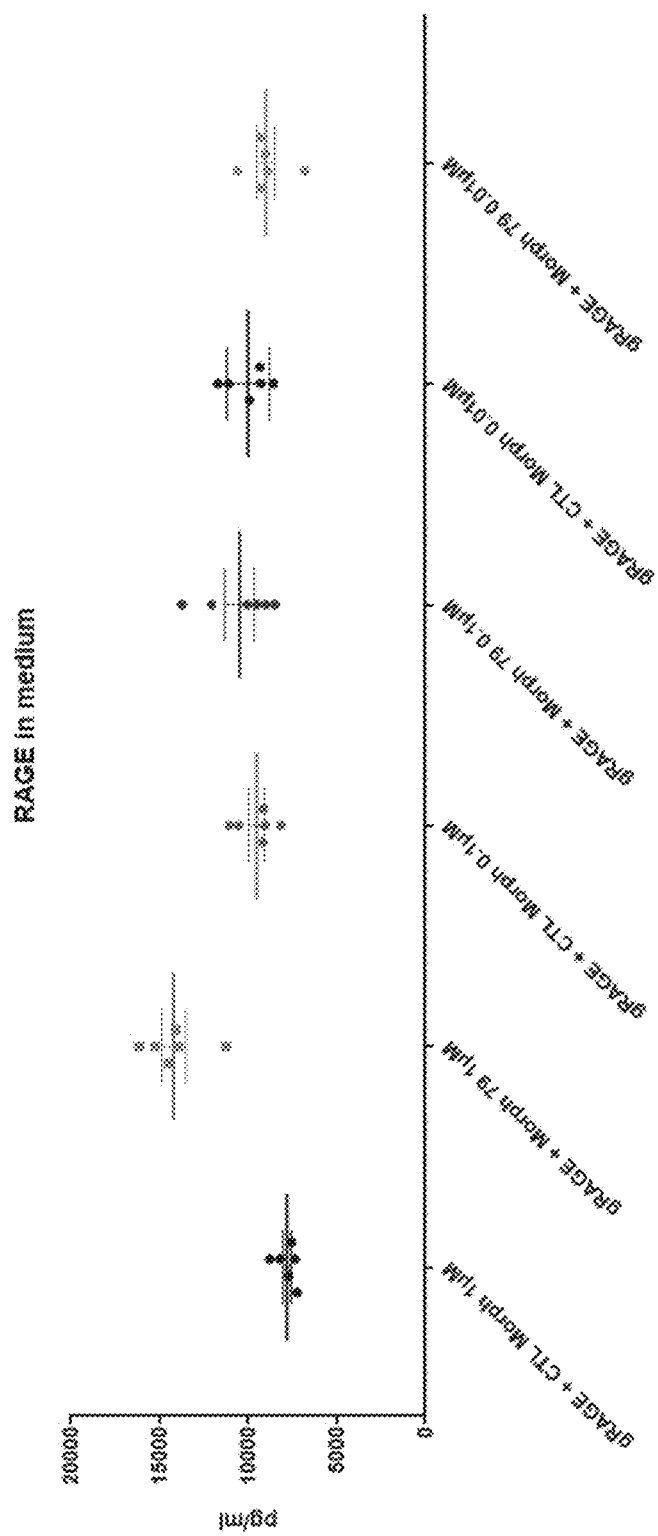
FIG. 1u shows the effect of treatment of CHO cells expressing genomic human RAGE with a vivo-morpholino formulation of AON 3779 (1 µM) on the expression of soluble RAGE protein in the culture medium, compared a non-target morpholino AON control.

Treatment of CHO cells expressing genomic human RAGE with an vivo-morpholino formulation of AON 3779 (1 µM) also increased expression of soluble RAGE, as measured on ELISA (FIG. 1u).

Figure 1V:
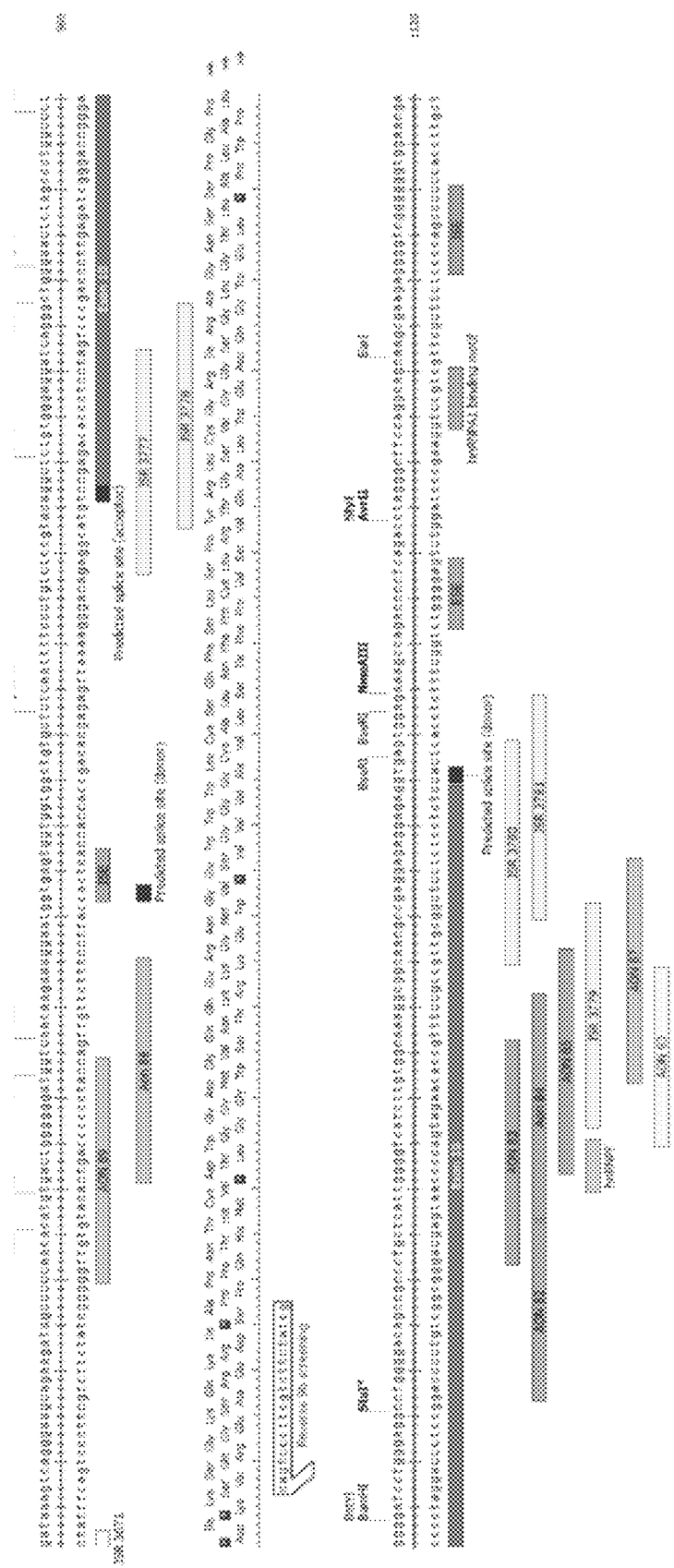
FIG. 1v shows the sequence of human RAGE DNA including and bounding exon 10, denoting the different AONs employed in above experiments and their complementary targets. The purple box denotes the putative polyG target of hnRNPF binding.

It is known that poly(G) stretches, especially the GGGG motifs can act as expression silencers, and they are often bound by hnRNP H and F (Sohail et al., BMC Genomics. 2014). It is hypothesised that RAGE splicing is partly regulated by G-rich cis-elements and heterogenous nuclear ribonucleoprotein H within intron 9/exon 9b, which are required for the preferential utilization of the upstream RAGE 5' splice site. Poly(G) stretches favour exon skipping as the binding of hnRNP H requires a continuous G stretch. AONs generally have poor affinity and reduced efficacy in G-rich regions. Exon 10 contains three GGGG motifs, one of which is recognised as an hnRNPF binding target and is flanked by AON 3779, 3787 and AON 3782 (FIG. 1v). However, mutating this region (RAGE mutant M3) had no effect on exon splicing or the response to AON3779 (FIG. 1w), suggesting we are modulating a novel silencer of RAGE splicing by targeting these regions with AONs to modulate splicing of RAGE, that could not have been predicted from prior art.

Example 2. Modulation of Alternative Splicing of Rage in Humans Cells Using Antisense Oligonucleotides Targeting Cis-Acting RNA Elements in Exon 9

Figure 2A:
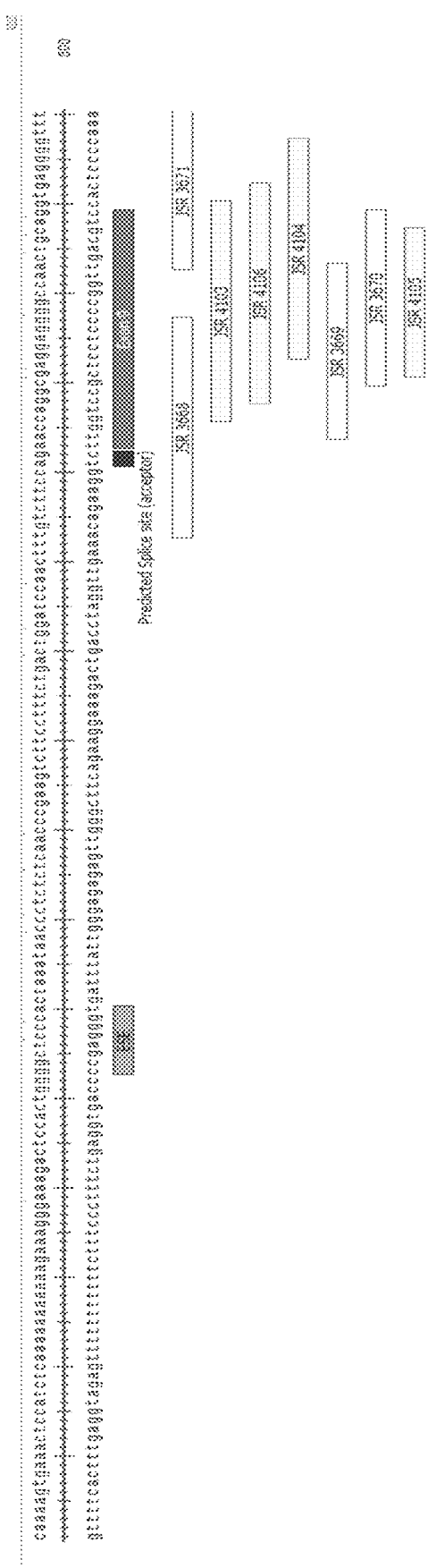
FIG. 2a shows the genetic sequence of human AGER including and bounding exon 9, denoting the different AONs utilised below and their complementary targets on RAGE pre-mRNA.

This example demonstrates that the alternative splicing of RAGE pre-mRNA can be modulated using AONs targeting cis-acting RNA elements in exon 9 of the pre-mRNA of RAGE (FIG. 2a).

Figure 2B:
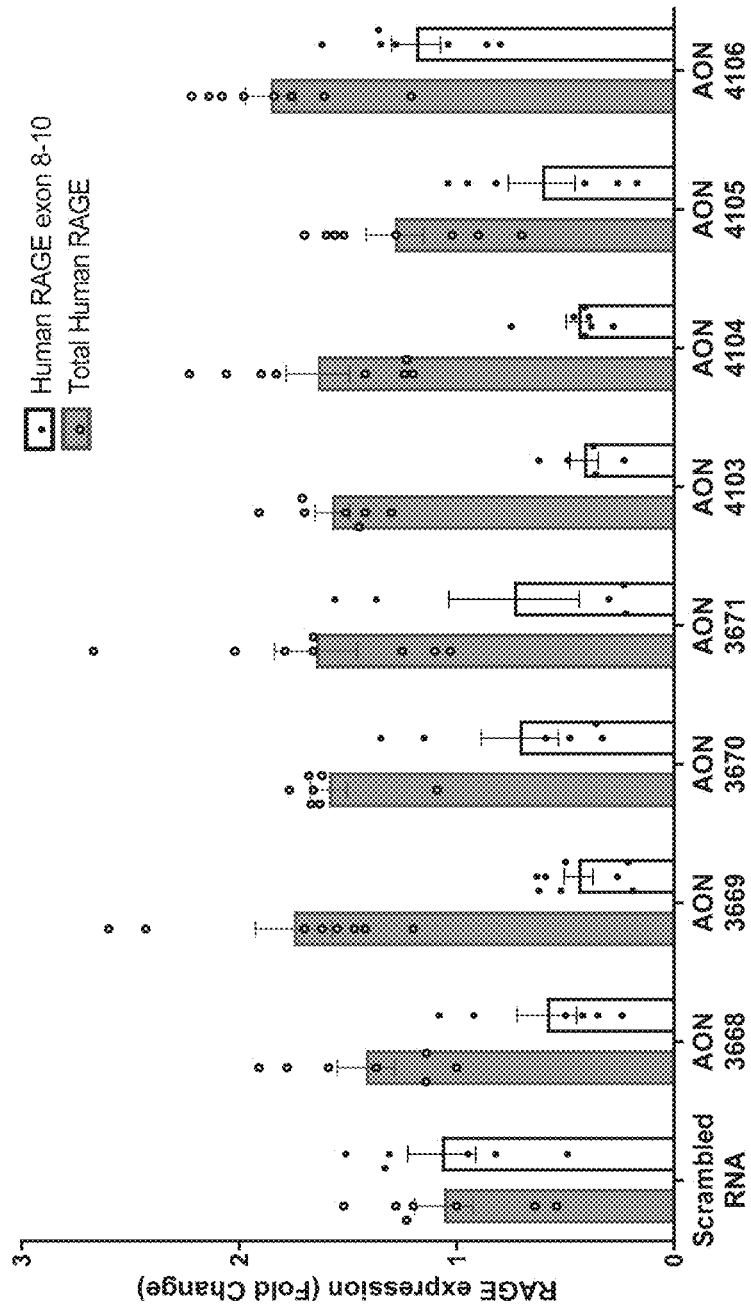
FIG. 2b shows the expression of any RAGE mRNA (total human RAGE) splicoforms and human RAGE mRNA splicoforms containing exon 10, as detected by real time RT-PCR following treatment of A579 cells with selected AONs targeting exon 9 or control (scrambled RNA treated) cells.

Transfection of Human lung epithelial cells (A549) with 10 nM concentrations some AONs targeting exon 9, in particular AONs 3668, 3669, 3670, 4103, 4104, 4105, reduced the expression of RAGE mRNA splicoforms containing exon 10, when compared to control (scrambled RNA treated) cells, as measured by real time RT-PCR (FIG. 2b). Another AONs targeting exon 9, in particular AON 4106, had no effect. However, the overall expression of RAGE mRNA was slightly elevated after treatment with all AONs targeting exon 9.

All RAGE mRNA splicoforms expressed in human lung epithelial cells (A549) in the presence and absence of selected AONs targeting exon 9, were isolated and cloned into *E. coli* Top10 cells. Using primers spanning exons 8-11, the size of each RAGE insert was determined (FIG. 2c). All AONs targeting exon 9 reduced the expression of percentage of mRNA clones expressing the 300 kB band (FIG. 2d), denoting full expression of signalling capable elements contained in exon 10 and 11. In particular, AON 3670 resulted in a reduction in RAGE mRNA splicoforms containing fragments 300 kB in size (FIG. 2d).

Transfection of Human lung epithelial cells (A549) with AONs targeting exon 9, in particular AONs 3669, 3670, 4103 also induced the de novo expression of RAGE mRNA splicoforms in which exon 8 was skipped (denoted by empty lanes on multiNA analyser; FIG. 2c)

Transfection of Human lung epithelial cells (A549) with AONs targeting exon 9, in particular, AON 3669, 3670, 4103 and 4105 also resulted in the de novo expression of RAGE mRNA splicoforms containing 276 kB fragments, denoting removal of exon 9 from splicoforms (FIG. 2d).

Figure 2E:
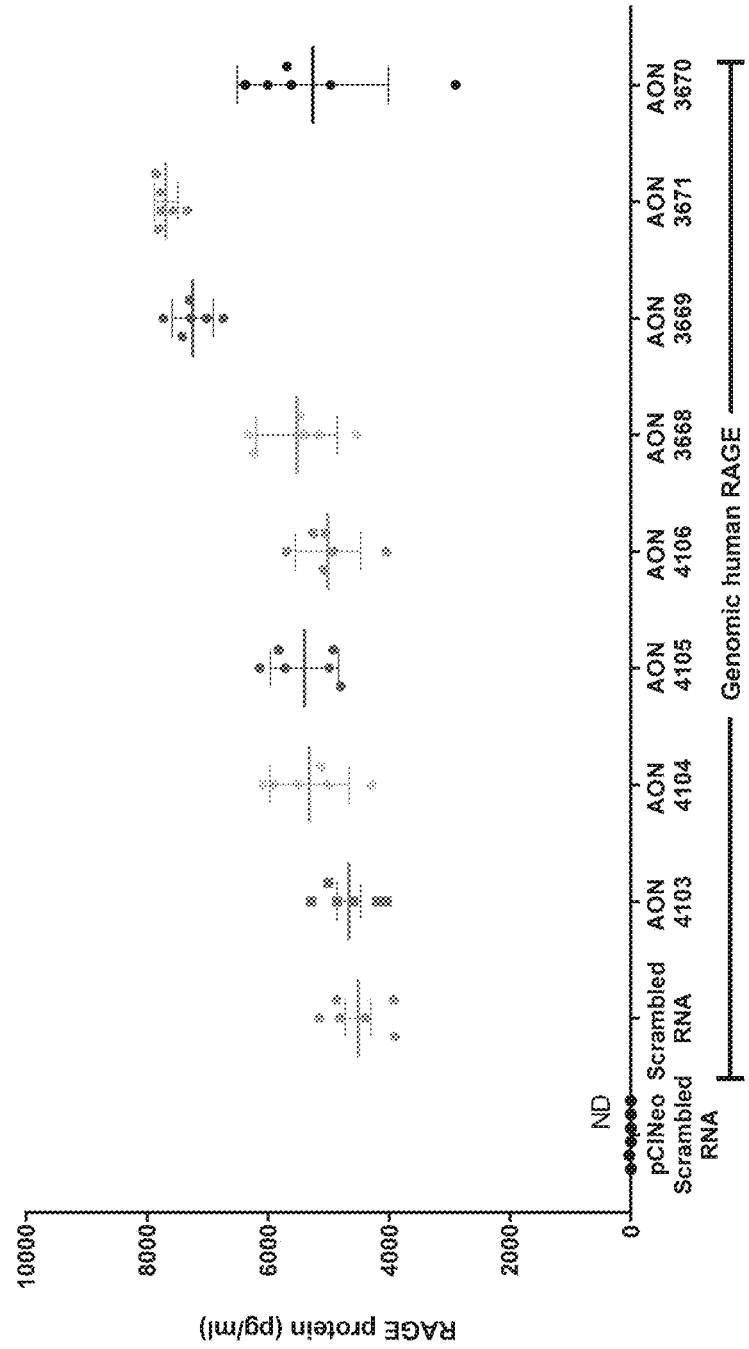
FIG. 2e shows the expression of soluble RAGE protein in the media following transfection of CHO cells with DNA coding for the genomic sequence of human RAGE, with and without selected AONs targeting exon 9, as measured by ELISA, control (scrambled RNA treated) cells. ND=not detected

In CHO cells transfected with a plasmid containing the genomic sequence of human RAGE (gRAGE), the amount of soluble RAGE secreted into the media, as measured on ELISA, was modestly increased by some AONs targeting the RAGE splice site in exon 9, specifically AON 3669 and 3671 (FIG. 2e), when compared to control (scrambled RNA treated) cells.

Transfection of Human lung epithelial cells (A549) with different concentrations AONs targeting exon 9, in particular AON 3669, 3670 and 4103 also inhibited the induction of pro-inflammatory signalling following activation of RAGE with the RAGE-ligand S100A8/A9 (0.6 µg/mL) including the induction of TLR-4 gene expression (FIG. 2f). Other AONs targeting exon 9, in particular AON 3668 and 4104 had no effect.

Figure 2G:
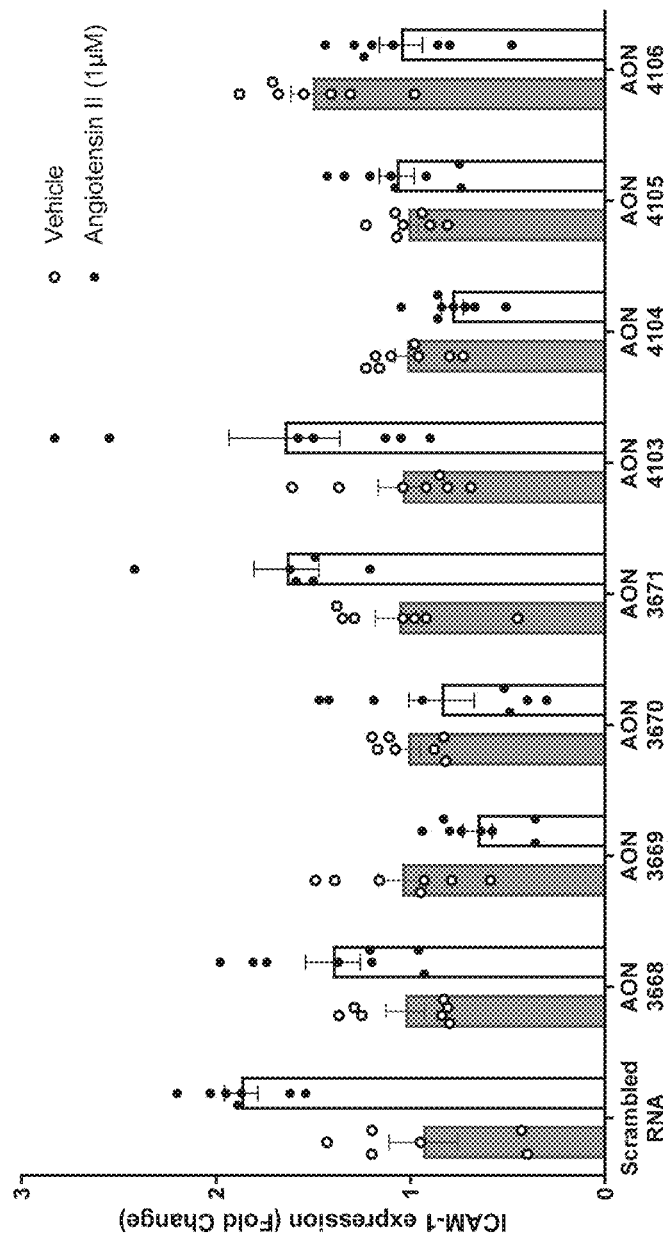
FIG. 2g shows the induction of ICAM-1 gene expression following treatment with Ang II (1 µM), which is capable of inducing transactivation of RAGE. Notably this induction in ICAM-1 gene expression is modulated following transfection of A579 cells with selected AONs targeting exon 9 compared to control (scrambled RNA treated) cells.

Transfection of Human lung epithelial cells (A549) with 10 nM AONs targeting exon 9, in particular AONs 3669, 3670, and 4104 also modulated the induction of proinflammatory signalling via ligand-independent transactivation of RAGE following activation of AT1 receptor by angiotensin II (1 µM; FIG. 2g). Other AONs targeting exon 9, in particular AON 3668, 3671 and 4103, had no effect.

Figure 2H:
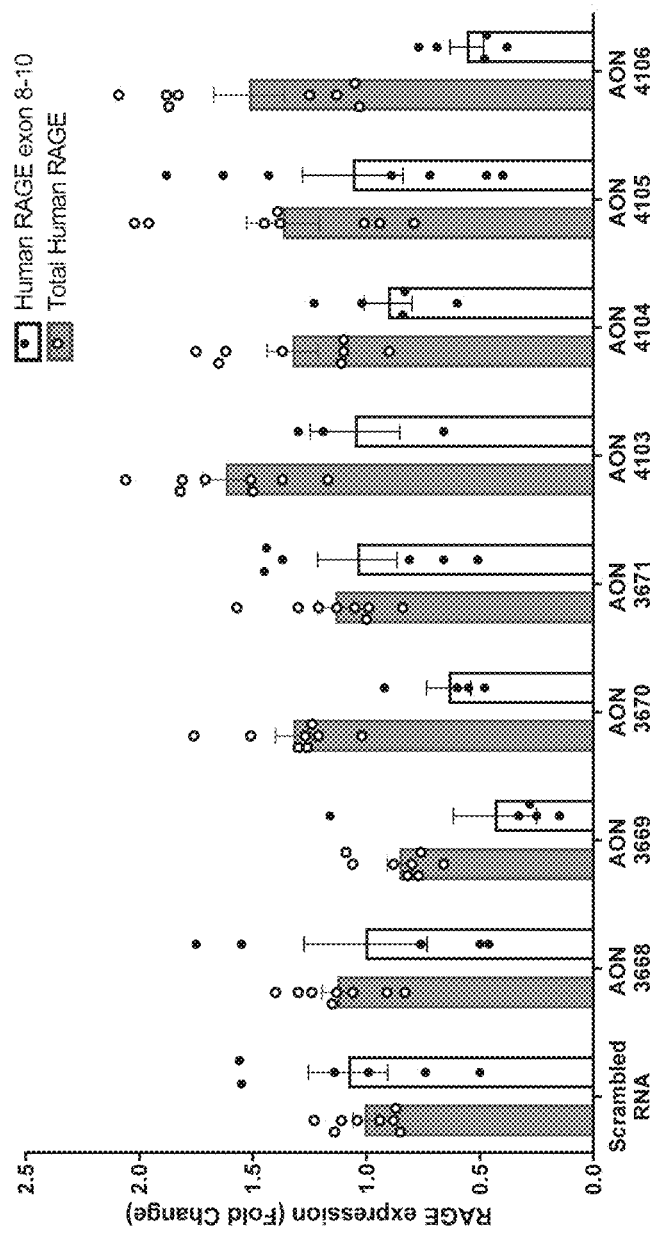
FIG. 2h shows the fold change in expression of any RAGE mRNA (total human RAGE) splicoforms and human RAGE mRNA splicoforms containing exon 10, as detected by real time RT-PCR following treatment of HMEC1 cells with selected AONs targeting exon 9 or a control (scrambled RNA) treated cells.

Transfection of Human microvascular endothelial cells (HMECs) with 10 nM AONs targeting exon 9, in particular AONs 3669 and 3670 also reduced the expression of endogenous RAGE mRNA splicoforms containing exon 10 (FIG. 2h).

Example 3. Modulation of Alternative Splicing of Rage in Humans Cells Using Antisense Oligonucleotides Targeting Cis-Acting RNA Elements in Exon 9B This example demonstrates that the alternative splicing of RAGE can be modulated using AONs targeting RNA elements within Exon 9b in the pre-mRNA of RAGE.

Exon 9b is removed by alternative splicing in most RAGE isoforms (FIG. 1e). This removal potentially requires the interaction of the splicosome with motifs in exon 9b. We hypothesised that modulating these binding elements using AONs could also modulate the alternative splicing of RAGE pre-mRNA.

Figure 3B:
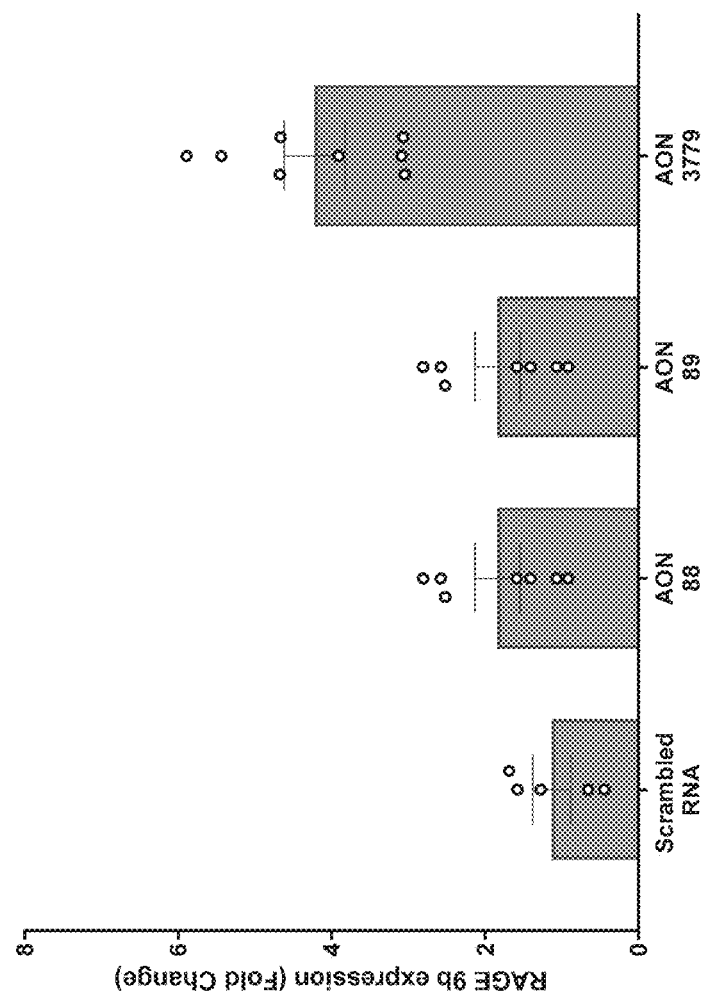
FIG. 3b shows the fold change in expression of RAGE mRNA splicoforms containing expn 9b sequence, as detected by real time RT-PCR, following treatment of A549 cells with selected AONs targeting intron 9, AON 3779 (as a positive control) or control (scrambled RNA treated) cells.

Transfection of Human lung epithelial cells (A549) with 10 nM concentrations AONs targeting exon 9b resulted in changes in the mRNA expression of RAGE mRNA splicoforms. The overall expression of RAGE was slightly elevated after treatment with both AONs targeting exon 9b (FIG. 3a). In addition, the expression of RAGE mRNA splicoforms containing exon 10 was modestly reduced after transfection with AON 88 compared to the scrambled control treated cells, as measured by real time RT-PCR (FIG. 3a). Expression of RAGE mRNA splicoforms containing exon 9b were also modestly increased by AONs 88 and 89 (FIG. 3b). Transfection with AON 3779 targeting exon 10 is shown as a positive control.

Figure 3C:
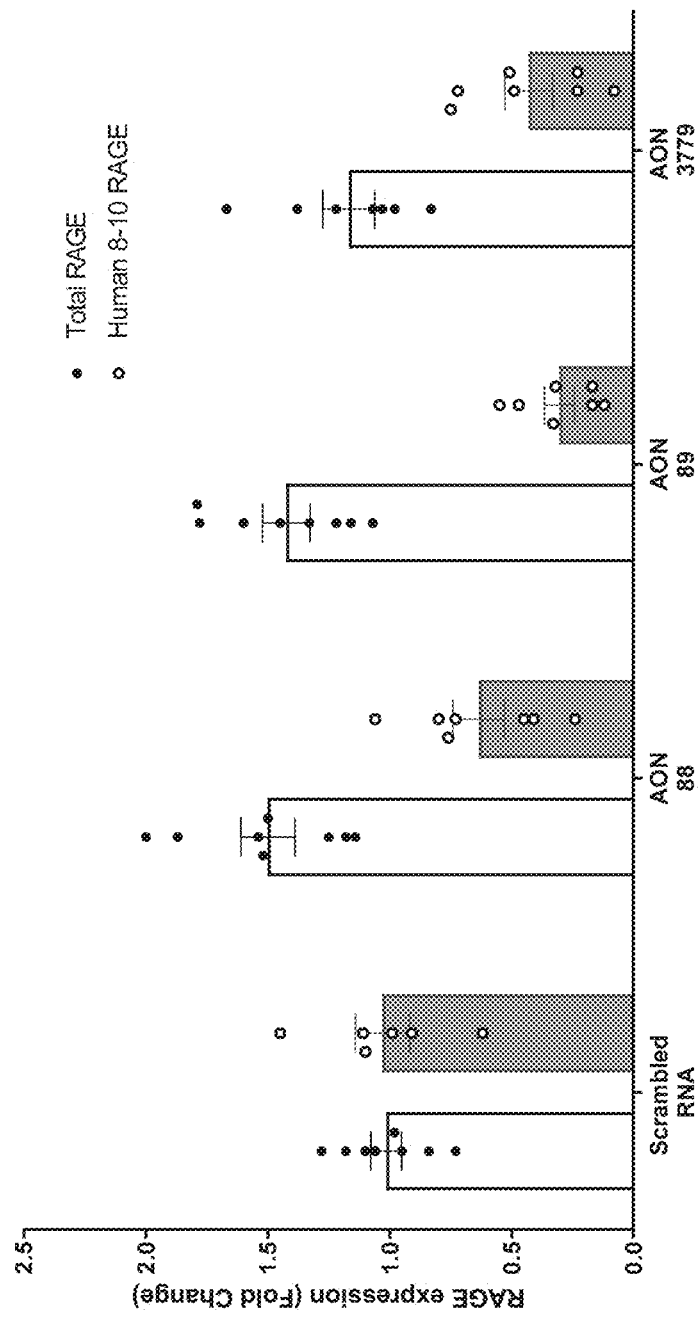
FIG. 3c shows the expression of any RAGE mRNA (total human RAGE) splicoforms and human RAGE mRNA splicoforms containing exon 10, as detected by real time RT-PCR following treatment of HMEC1 cells with selected AONs targeting intron 9, AON 3779 (as a positive control), or control (scrambled RNA treated) cells.

Transfection of Human microvascular endothelial cells (HMECs) with 10 nM concentrations AONs targeting exon 9b also resulted in reduced expression of RAGE mRNA splicoforms containing exon 10 (FIG. 3c) and increased expression of RAGE mRNA splicoforms containing exon 9b (FIG. 3d). Again, the overall expression of the RAGE mRNA was slightly elevated after treatment with both AONs targeting exon 9b (FIG. 3c). Transfection with AON 3779 targeting exon 10 is shown as a positive control.

Figure 3E:
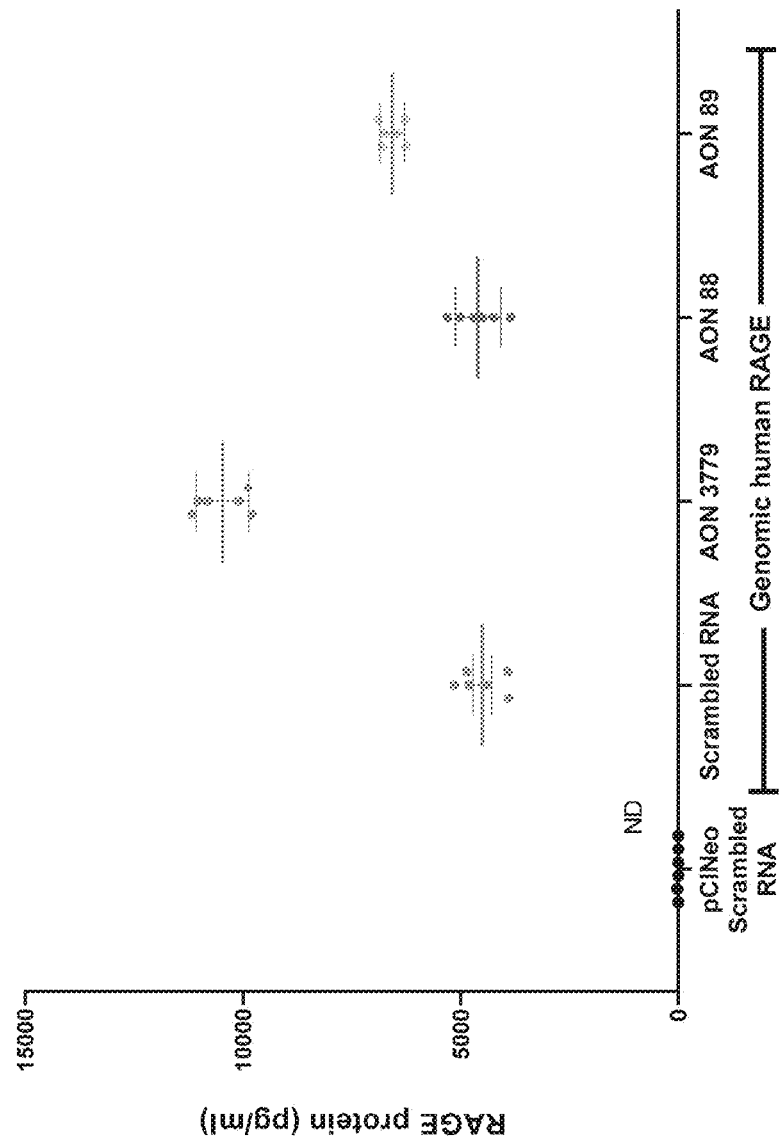
FIG. 3e shows the concentration of soluble RAGE as detected by ELISA in the media following treatment of A579 cells expressing genomic human RAGE, with specific AONs targeting intron 9, AON 3779 (as a positive control), or control (scrambled RNA treated) cells.

In CHO cells transfected with a plasmid containing the genomic sequence of human RAGE (gRAGE), the amount of soluble RAGE secreted into the media, as measured on ELISA, was modestly increased by some AONs targeting exon 9b, specifically AON 89 (FIG. 3e), when compared to control RNA. Transfection with AON 3779 targeting exon 10 is shown as a positive control.

Figure 3F:
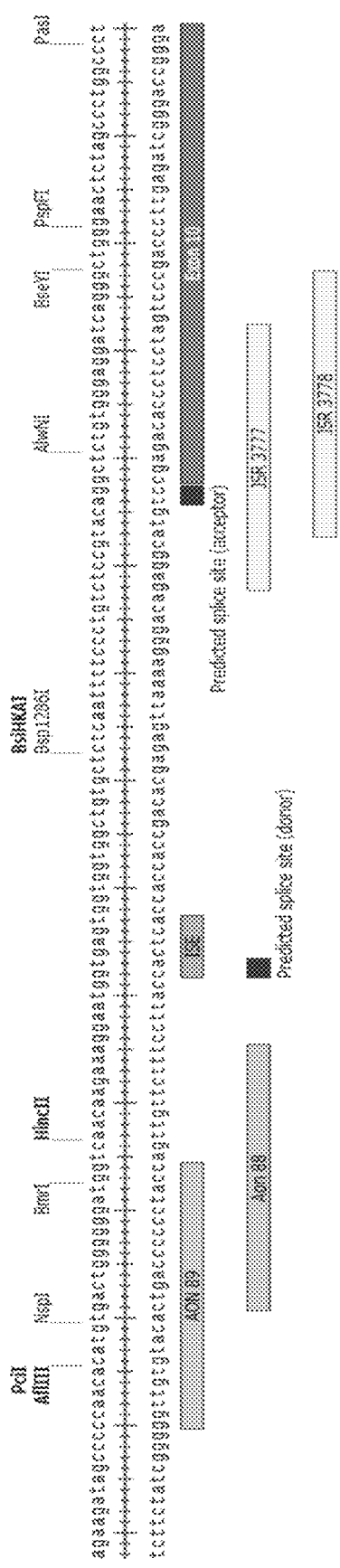
FIG. 3f shows the sequence of human RAGE DNA including and bounding intron 9, denoting the AONs and their complementary targets.

The human RAGE sequence of intron 9 and complementary targeting for AON 88 and 89 is shown in FIG. 3f.

Example 4. Modulation of Alternative Splicing of Murine Rage Using Antisense Oligonucleotides Targeting Cis-Acting RNA Elements in Rage Pre-mRNA This example demonstrates that the alternative splicing of RAGE pre-mRNA can also be modulated using certain AONs targeting cis-acting RNA elements in exon 9, 9B and 10 in the pre-mRNA of murine RAGE, and that this modulation can be demonstrated, in vitro, ex vivo and in vivo.

Figure 4A:
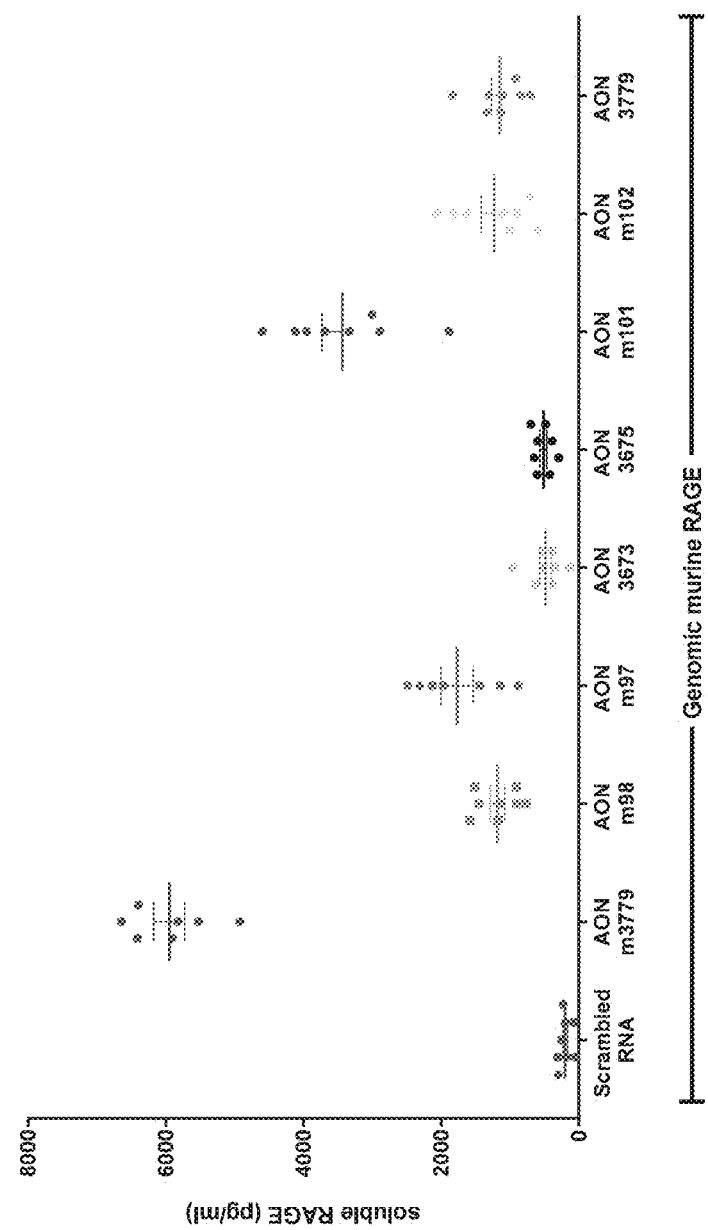
FIG. 4a shows the concentration of soluble RAGE as detected by ELISA in the media following treatment of CHO cells expressing genomic murine RAGE, with AONs targeting RAGE pre-mRNA or control (scrambled RNA treated) cells.

To test the effect of AONs on the alternative splicing of murine RAGE, CHO cells were transfected with a plasmid containing the genomic sequence of murine RAGE. This resulted in the secretion of small amounts of esRAGE. Transfection with AONs targeting murine RAGE, in particular AON m3779 (an AON designed to target exon 10 of the murine RAGE sequence in a comparable sequence targeted by AON 3779 in the human RAGE sequence detailed in example 1) and AON m101, increased the secretion of esRAGE into the cell media (FIG. 4a).

Figure 4B:
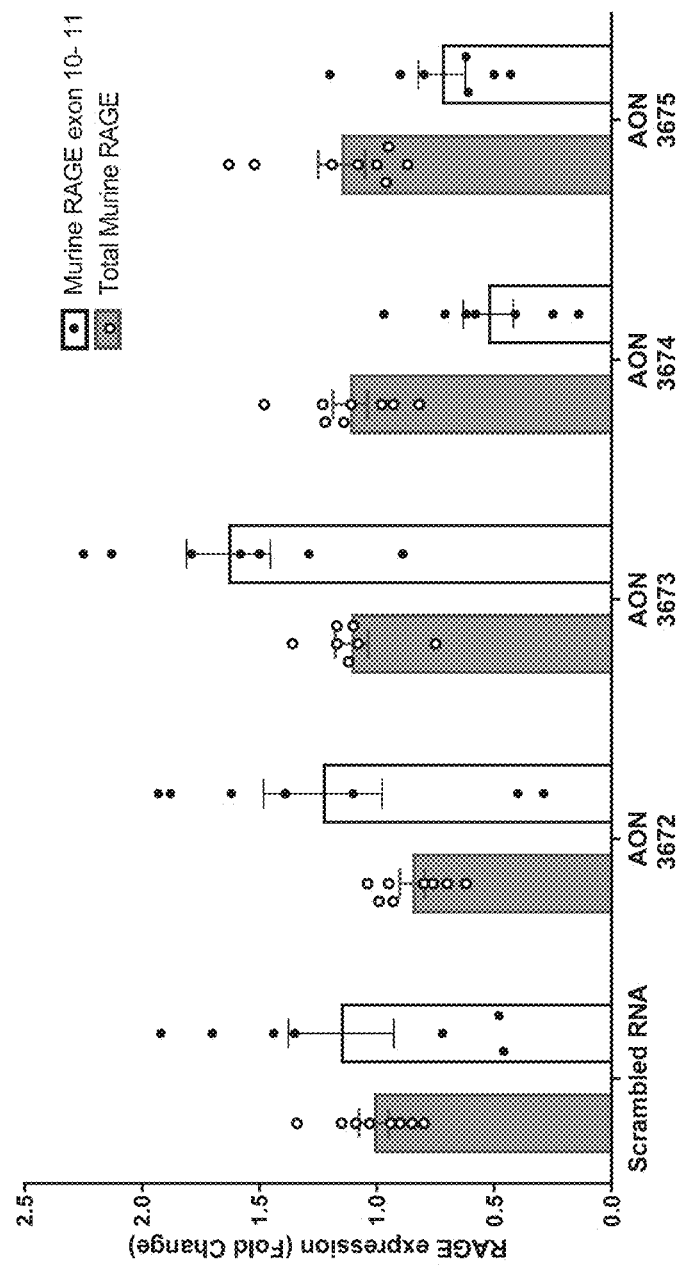
FIG. 4b shows the fold change in expression of any RAGE mRNA (total murine RAGE) splicoforms and RAGE mRNA splicoforms containing exon 10 and 11 on real time RT-PCR, following treatment of PMAEC with selected AONs (50 nM) targeting exon 9 of murine RAGE or control (scrambled RNA treated) cells.

Primary mouse aortic endothelial (PMAEC) cells were transfected with AONs (50 mM) targeting exon 9 of RAGE (table 3d). This treatment resulted in modest changes in the expression of RAGE mRNA splicoforms compared to their respective negative-control. In particular, AON 3674 and 3675 were able to reduce expression of RAGE mRNA splicoforms containing exon 10, as measured by real-time RT-PCR (FIG. 4b).

Figure 4C:
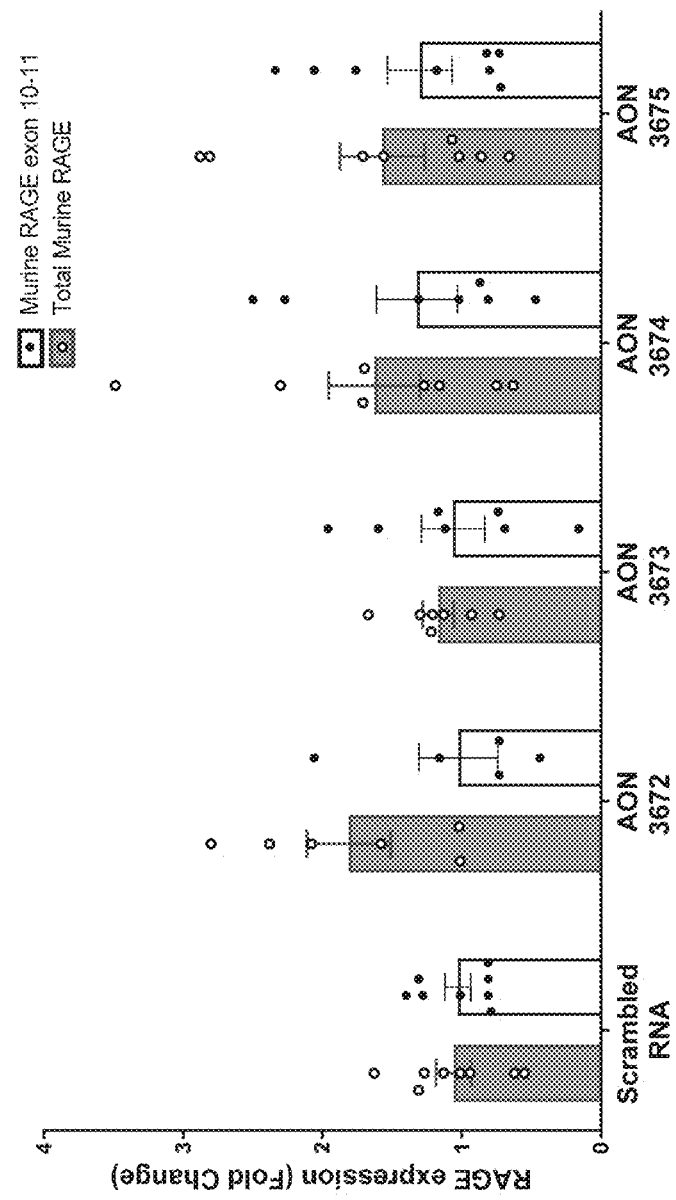
FIG. 4c shows the fold change in expression of any mRNA RAGE (total murine RAGE) and RAGE mRNA splicoforms containing exon 10 and 11 following treatment of PMAEC with selected AONs (10 nM) targeting exon 9 of murine RAGE or control (scrambled RNA treated) cells.

However, transfection of PMAECs with these AONs used at 10 nM showed no significant effect on the expression of RAGE mRNA splicoforms (FIG. 4c). Levels of soluble RAGE secreted into the media were modestly increased 24-hours following transfection of cultured PMAEC with AON 3674 and 3675 at 50 nM (FIG. 4d).

Figure 4E:
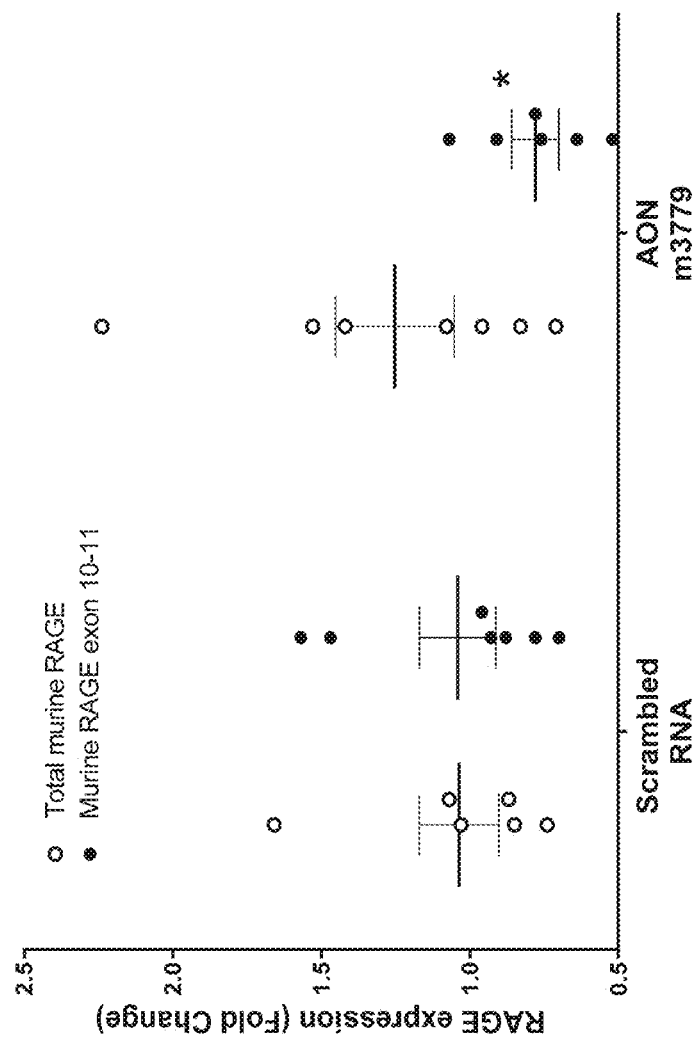
FIG. 4e shows the fold change in expression of any RAGE mRNA (total murine RAGE) splicoforms and RAGE mRNA splicoforms containing exon 10 and 11 on real time RT-PCR, following treatment of PMAEC with AON m3779 (10 nM) or control (scrambled RNA treated) cells.

Transfection of CHO cells expression genomic murine RAGE with m3779 (10 nM) reduced the expression of RAGE mRNA splicoforms containing exon 10, as estimated by real-time RT-PCR; FIG. 4e) and increased the secretion of esRAGE when compared to control (scrambled RNA treated) cells (FIG. 4f). AON 3779 targeting human RAGE sequences also increased esRAGE secretion, but not as much as AON m3779.

When the AONs designed to target exon 10 of the murine sequence of RAGE were transfected into the CHO cells expressing genomic sequence of human RAGE off a plasmid, AON m3779 (designed to target murine RAGE exon 10), also induced an increase in soluble human RAGE in the cell media (FIG. 4g). However, AON 3779 (specifically targeting human RAGE exon 10) was more effective in modulating genomic human RAGE that AON m3779. This data demonstrates that AONs targeting a specific sequence in exon 10 can be effective in modulating RAGE splicing, despite regions of non-identity.

Figure 4H:
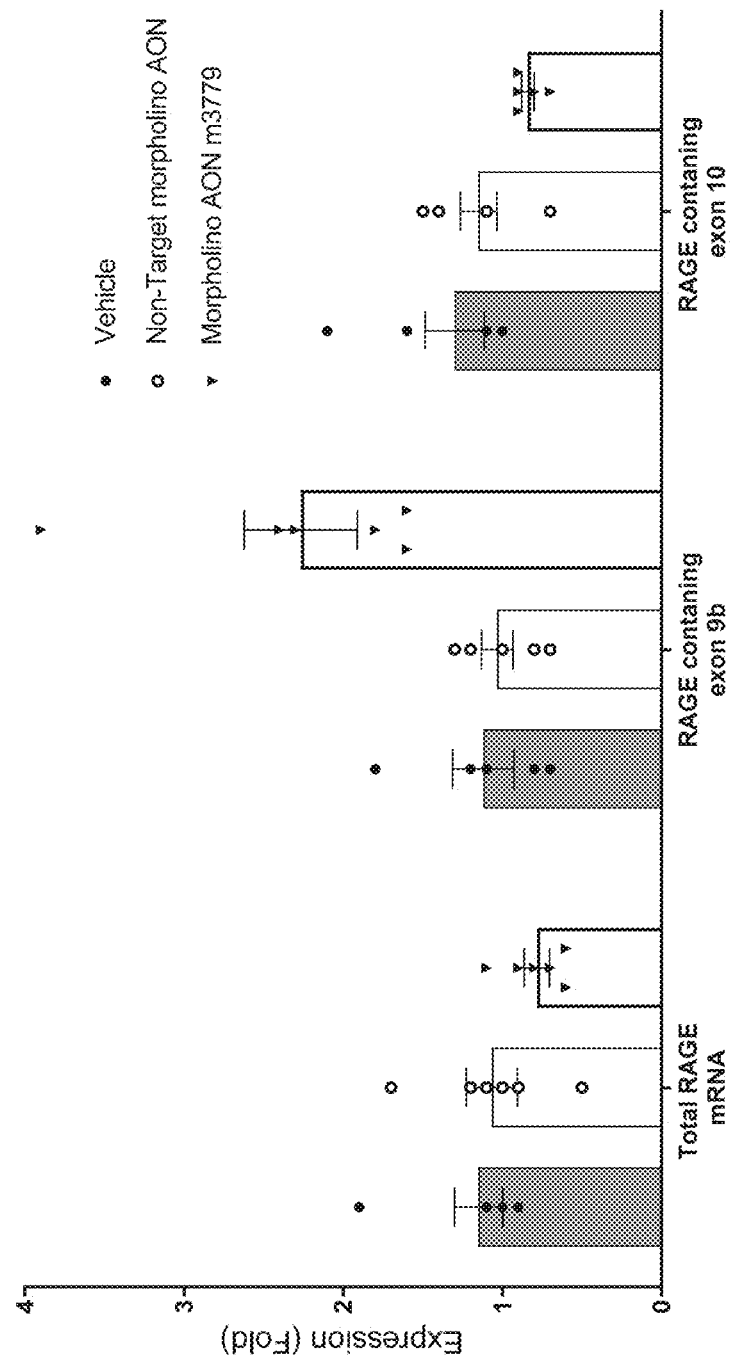
FIG. 4h shows the expression of any RAGE mRNA (total RAGE) splicoforms and RAGE mRNA splicoforms containing exon 10 and 11 on real time RT-PCR following treatment of precision cut lung slices from mice with AON m3779 or a non-target morpholino AON for 48 hours.

To test the effect of AON targeting RAGE in murine tissue, precision cut lung slices (PCLS) were obtained from mice and then cultured ex vivo. In brief, mice were humanely killed, their explanted lungs infused with agarose, cylindrical cores taken and then cut with a tissue slicer, generating lung slices with uniform diameter and thickness. PCLS were then be submerged in culture medium in multi-well plates under tissue culture conditions. After 24 hours PCLS were then transfected with vivo-morpholino AON 3779 or a non-target control for 48 hours. Treatment with AON 3779 resulted in a significant increase in the expression of RAGE mRNA containing exon 9b and reduced expression of RAGe mRNA splicoforms containing exon 10 (FIG. 4h), with the greatest effect on exon 9b seen 72 hours after dosing (FIG. 4i).

To validate the in vivo relevance of AONs targeting RAGE splicing, male C57bl6 mice were injected subcutaneously with AON m3779 (1 mg/kg/daily) for 7 days. Expression of RAGE mRNA splicoforms containing exon 9b were increased in the lungs of mice and splicoforms containing exon 10 were reduced following subcutaneous treatment with AON m3779 for one week (FIG. 4j).

Figure 4K:
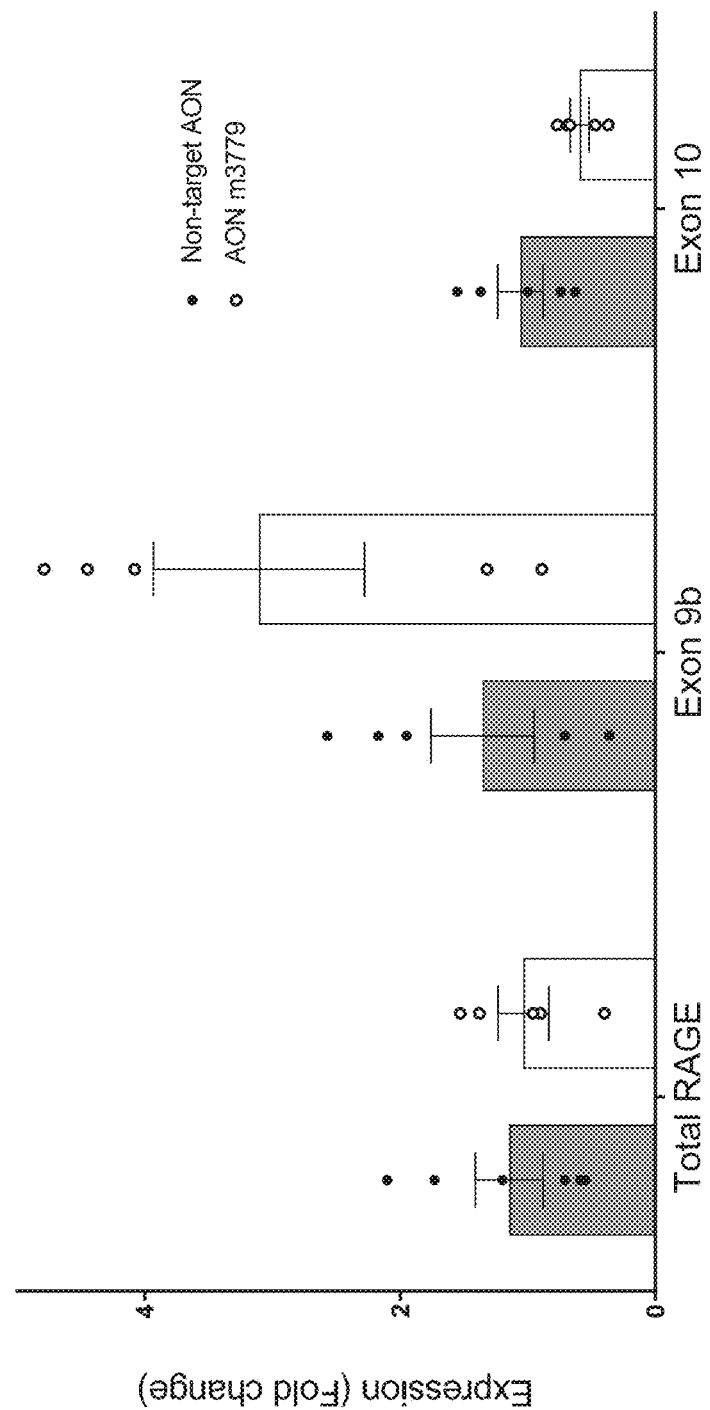
FIG. 4k shows the fold change in pulmonary expression of any RAGE mRNA (total mouse RAGE) splicoforms and murine RAGE mRNA splicoforms containing exon 10 and 11 on real time RT-PCR 48 hours after intratracheal instillation of a morpholino formulation of AON m3779 into C57Bl6 mice, compared to non-target AON control.

To validate their potential as an inhaled therapeutic agent, live mice were anesthetised before delivering 30 μL of 11 μM vivo-morpholino-AON m3779 or a non-target vivo-morpholino control (as a negative control) in RNAse free water into the lung via the trachea using a cannula or water alone. The anaesthetic was reversed, and mice were killed 48-hrs later. Intratracheal treatment with m3779 resulted in a significant decrease in the pulmonary expression of RAGE mRNA splicoforms containing exon 10 compared to water alone, which had no significant effect. The expression of RAGE mRNA isoforms containing exon 9b was also increased. (FIG. 4k). A similar reduction in the expression of RAGE mRNA splicoforms containing exon 10 was seen after intratracheal-delivery of 30 μl of 11 μM a 2-0'Me-phosphorothioate AON m3779 when compared to vehicle (sterile water) alone (FIG. 4l). In addition, an increase in circulating soluble RAGE was also observed after treatment of mice with AON m3779 when compared to sterile water or an ineffective AON 4105 targeting human RAGE (FIG. 4m).

Example 5. Modulation of Alternative Splicing of Rage Using a Combination of Antisense Oligonucleotides Targeting Rage Pre-mRNA This example demonstrates that the alternative splicing of RAGE can be modulated using combinations of AONs targeting different cis-acting RNA elements in the pre-mRNA of RAGE.

Exon definition is thought to be regulated by assembly of a multicomponent "cross-exon" recognition complex that facilitates target retention or exclusion. Following binding of AON 3779 to exon 10 in the pre-mRNA of RAGE to increase the generation of esRAGE, we speculate that other regulatory targets in exon 10 may become more critical, including, but not limited to, predicted splice sites. Moreover, in the presence of AON 3779, by selectively targeting these cis-acting RNA elements in exon 10 in the pre-mRNA of RAGE using other AONs, we would prevent any escape from exon exclusion and further modulate RAGE splicing towards the preferred generation of esRAGE.

The secondary structure of exon 10 of RAGE is predicted to contain two hairpin loops linked by a central hinge region. It is speculated that targeting exonic enhancer sequences in the 3' hairpin using AON 3779, would increase the importance of targets in the alternate 5' hairpin, including the upstream 5' splice site in exon 10.

Figure 5A:
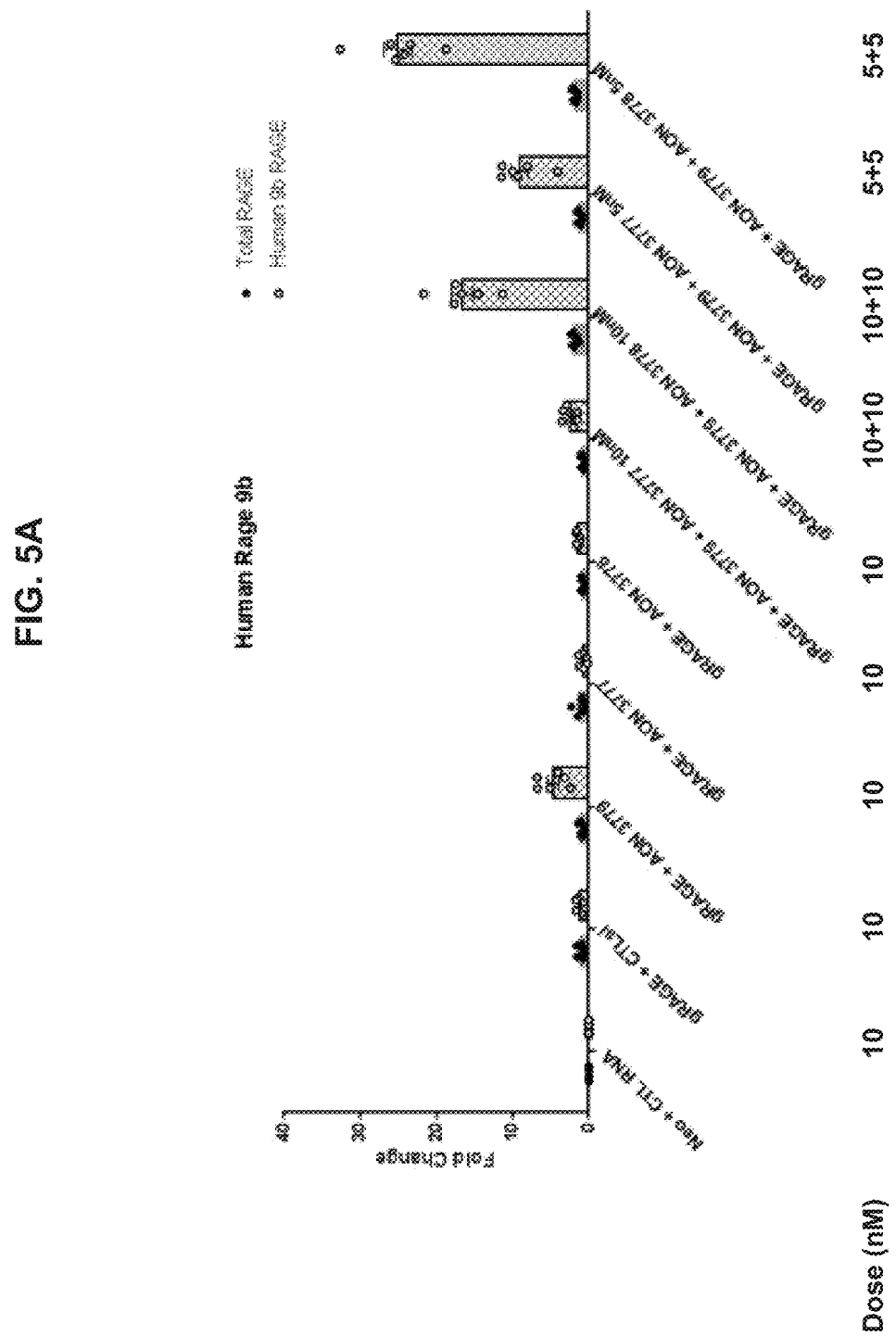
FIG. 5a shows the expression of RAGE mRNA splicoforms containing exon 9b, as measured by real time RT-PCR, following transfection of CHO cells with DNA coding for the genomic sequence of human RAGE (gRAGE), with and without combinations of selected AONs targeting different regions exon 10 or control (scrambled RNA treated) cells.
Figure 5B:
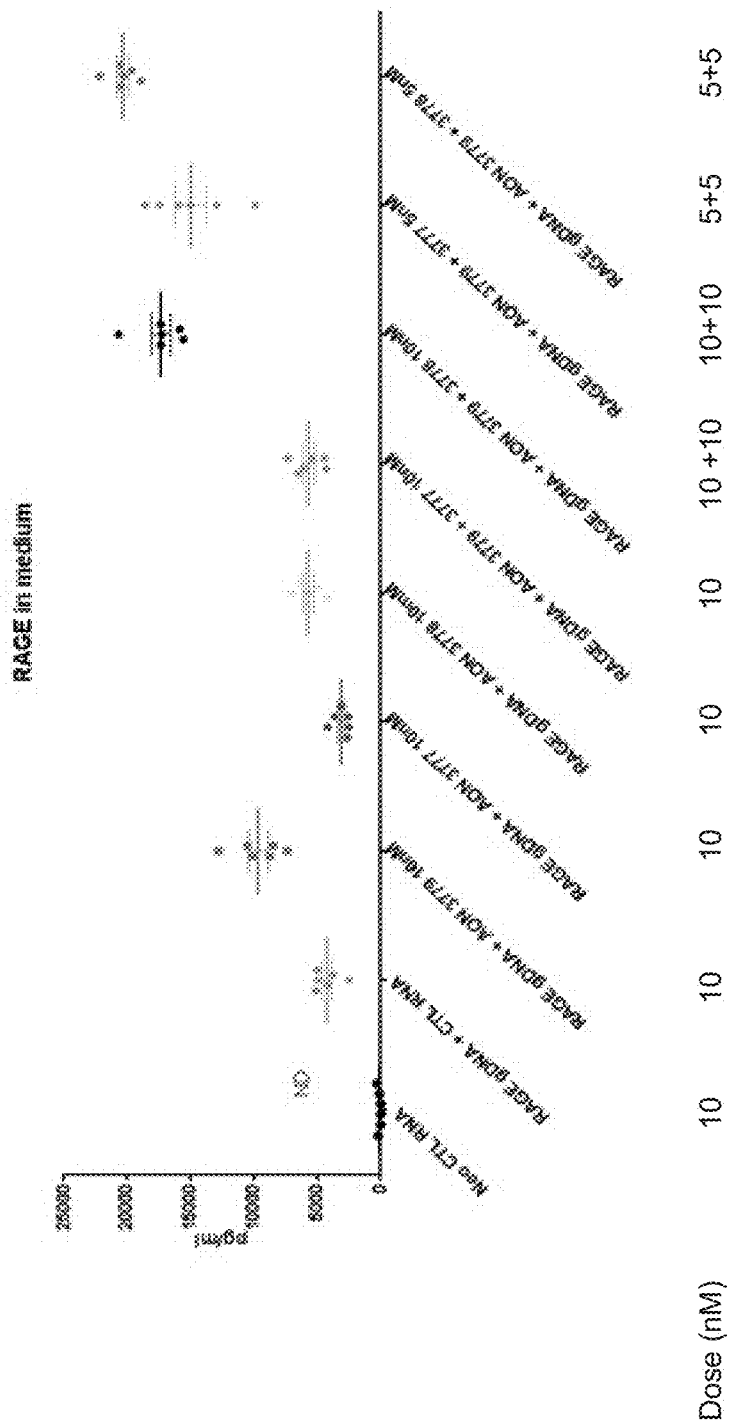
FIG. 5b shows the expression of soluble RAGE protein in the media following transfection of CHO cells with DNA coding for the genomic sequence of human RAGE (gRAGE), with and without combinations of selected AONs targeting the 5' splice site of exon 10 or control (scrambled RNA treated), as measured by ELISA.

To validate this hypothesis, CHO cells containing a plasmid coding for genomic human RAGE, were transfected with AON 3779 (10 nM) in combination with other AONs targeting the 5' (acceptor) predicted splice site in exon 10 (also 10 nM). This combination treatment resulted in changes in the expression of RAGE mRNA splicoforms such that some combinations, in particular AONs 3779+3777, 3779+3778, significantly increased the expression of RAGE mRNA isoforms containing exon 9b, when compared to AON 3779 alone or control scrambled RNA treated cells, as measured by real time RT-PCR (FIG. 5a). This combination also increased the production of esRAGE protein measured in the media by ELISA (FIG. 5b). The combination of AON 3997 and AON 3778 was also more effective at low dose (5 nM+5 nM). Notably, AON 3777 and AON 3778 had little or no effect on their own at 10 nM.

Figure 5C:
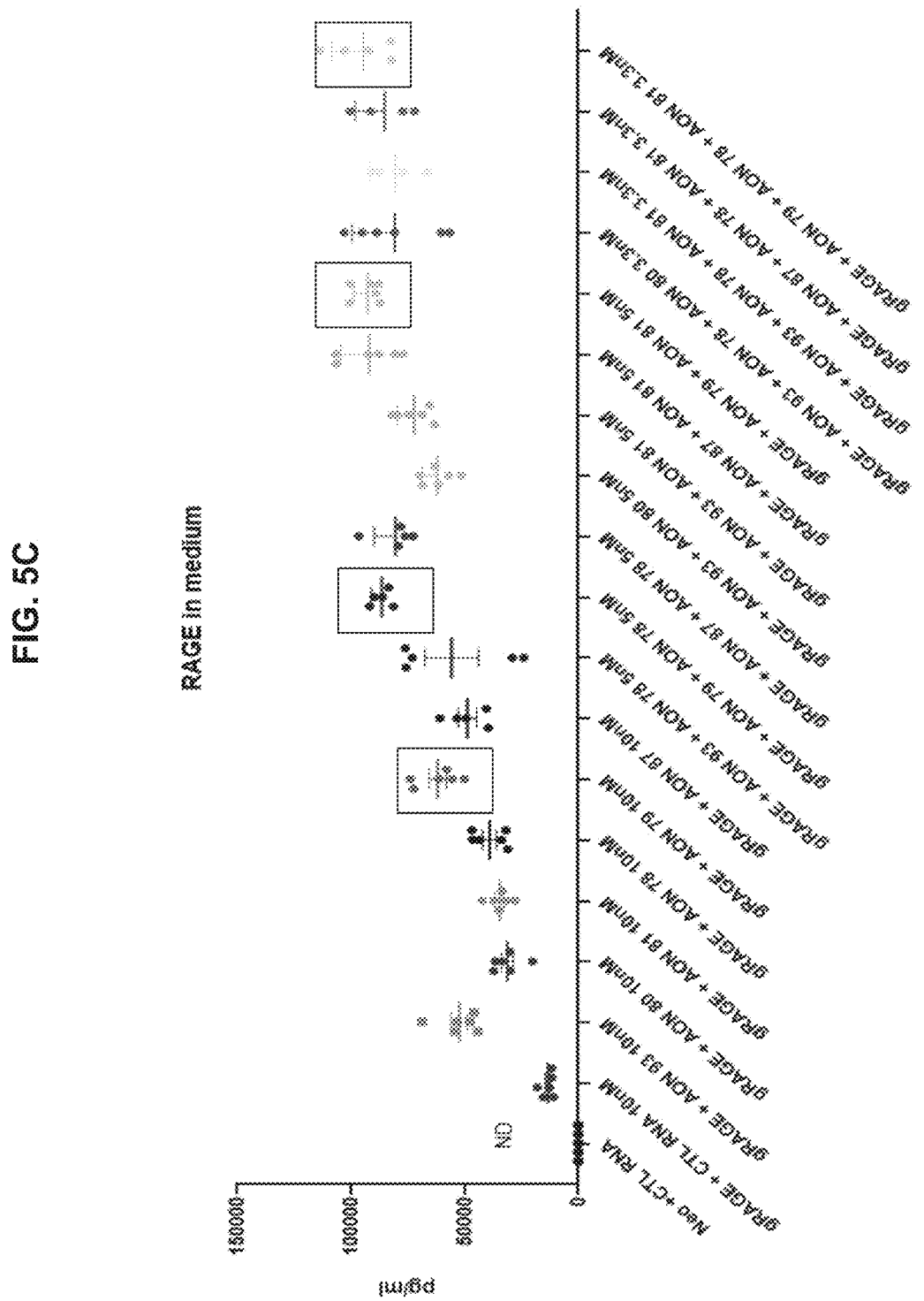
FIG. 5c shows the expression of soluble RAGE protein in the media following transfection of CHO cells with DNA coding for the genomic sequence of human RAGE (gRAGE), with and without combinations of selected AONs targeting the 3' and 5' splice site of exon 10 or control RNA, as measured by ELISA. Boxes indicate treatments including AON 3779.

In another experiment, transfection of CHO cells containing a plasmid coding for genomic human RAGE, were transfected with AON 3779 in combination with other AONs targeting either the 3' or the 5' splice sites in exon 10. Some combinations also resulted in changes in the expression of RAGE mRNA splicoforms, such that some combinations, in particular AONs 3779+3778, 3779+3781 and 3779+3778+3781 significantly increased the expression soluble RAGE when compared to AON 3779 alone or the scrambled control treated cells, as measured by ELISA (FIG. 5c). This increase was similar when using AON 93 or AON 87 instead of 3779, although combinations with AON 3779 (denoted in boxes) were strongest and most consistent overall.

Figure 5D:
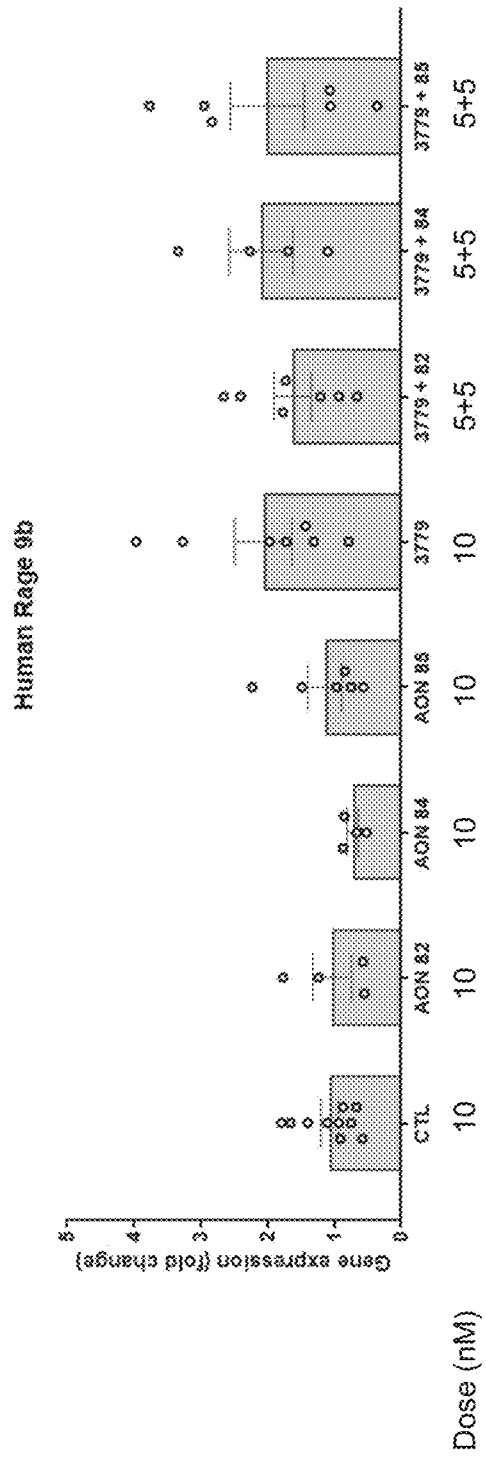
FIG. 5d shows the expression of RAGE mRNA splicoforms containing exon 9b following transfection of CHO cells with DNA coding for the genomic sequence of human RAGE, with and without combinations of selected AONs targeting adjacent regions of exon 10 or control (scrambled RNA) treated cells, as measured by real time RT-PCR.

Transfection of Human lung epithelial cells (A549) with other combinations of AONs also targeting adjacent regions in exon 10, in particular AON 3779+3782, 3779+3784, 3779+3785 had no significant effect on the expression of RAGE isoforms containing exon 9b beyond AON 3779 alone (FIG. 5d). Notably, these AONs also targeted the 5' hairpin (similar to AON 3779) and/or central hinge region, in distinction AON 3777 or 3778, that were effective in combination, which target exonic enhancers on the other (3') hairpin.

CHO cells containing a plasmid coding for the genomic sequence of murine RAGE were transfected with AON m3779 in combination with AONs targeting either the 3' or the 5' splice sites in exon 10. This combination treatment resulted in changes in the expression of RAGE mRNA splicoforms such that some combinations, in particular AONs m3779+m102, significantly increased the secretion of soluble RAGE into cell media, as measured by ELISA, when compared to the AON m3779 individually (FIG. 5e).

What is claimed:

1. A method for manipulating splicing in a Receptor for Advanced Glycation End-products (RAGE) pre-mRNA resulting in the skipping of exon 10, the method comprising:
   contacting a cell with one or more antisense oligonucleotides having a nucleotide sequence at least 85% complementary to an identified target region of exon 10 of RAGE pre-mRNA over the entirety of the antisense oligonucleotide, wherein, in the identified target region, the 5'-most nucleotide is nucleotide position 88 or 114 of exon 10 or is between nucleotide positions 88 to 114 of exon 10, and wherein the identified target region enhances alternative splicing to exclude exon 10 and to generate a soluble form of RAGE; and further wherein the one or more antisense oligonucleotides binds to the RAGE pre-mRNA within the identified target region; wherein the one or more antisense oligonucleotides is 8 to 25 nucleotides in length; wherein the one or more antisense oligonucleotides comprises at least one modified nucleotide; and
   manipulating splicing in the RAGE pre-mRNA resulting in the skipping of exon 10 and reducing the expression of RAGE mRNA containing exon 10 by the binding of the one or more antisense oligonucleotides to the target region of exon 10 in the RAGE pre-mRNA.

2. The method according to claim 1, wherein the 5'-most nucleotide of the target region is between nucleotide positions 90 to 114 of exon 10 of RAGE pre-mRNA.

3. The method according to claim 1, wherein the 5'-most nucleotide of the target region is between nucleotide positions 88 to 107 of exon 10 of RAGE pre-mRNA.

4. The method according to claim 1, wherein the 5'-most nucleotide of the target region is between nucleotide positions 90 to 102 of exon 10 of RAGE pre-mRNA.

5. The method according to claim 1, wherein the target region is between nucleotide positions 90 to 114 of exon 10 of RAGE pre-mRNA.

6. The method according to claim 1, wherein the target region is between nucleotide positions 88 to 107 of exon 10 of RAGE pre-mRNA.

7. The method according to claim 1, wherein the target region is between nucleotide positions 90 to 102 of exon 10 of RAGE pre-mRNA.

8. The method according to claim 1, wherein antisense oligonucleotide has a nucleotide sequence at least 90% complementary to the target region of exon 10 of RAGE pre-mRNA.

9. The method according to claim 1, wherein antisense oligonucleotide has a nucleotide sequence at least 95% complementary to the target region of exon 10 of RAGE pre-mRNA.

10. The method according to claim 1, wherein antisense oligonucleotide has a nucleotide sequence that is 100% complementary to the target region of exon 10 of RAGE pre-mRNA.

11. The method according to claim 1, wherein the antisense oligonucleotide is 8 to 15 nucleotides in length.

12. The method according to claim 11, wherein the antisense oligonucleotide is 9 to 14 nucleotides in length.

13. The method according to claim 12, wherein the antisense oligonucleotide is 13 nucleotides in length.

14. The method according to claim 13, wherein the target region is between nucleotide positions 90 to 114 of exon 10 of RAGE pre-mRNA.

15. The method according to claim 13, wherein the target region is between nucleotide positions 88 to 107 of exon 10 of RAGE pre-mRNA.

16. The method according to claim 13, wherein the target region is between nucleotide positions 90 to 102 of exon 10 of RAGE pre-mRNA.

17. The method according to claim 1, wherein the modified nucleotide comprises any one or more of a morpholino group, a modified linkage, or a modified sugar moiety.

18. The method according to claim 17, wherein the modified sugar moiety comprises methylation at a 2' hydroxyribose position.

19. The method according to claim 17, wherein the modified linkage is a phosphorothioate linkage.

20. The method according to claim 1, wherein the antisense oligonucleotide is a phosphorodiamidate morpholino oligomer (PMO).

21. The method according to claim 1, wherein the antisense oligonucleotide is further modified by: (i) chemical conjugation to a moiety; and/or (ii) tagging with a cell penetrating peptide.

22. The method according to claim 1, wherein, if a uracil is present in the antisense oligonucleotide, the uracil (U) of the antisense oligonucleotide is replaced by a thymine (T).

23. A method of treating a disease associated with RAGE expression, the method comprising: administering to a patient an effective amount of an antisense oligonucleotide having a nucleotide sequence at least 85% complementary to an identified target region of exon 10 of RAGE pre-mRNA over the entirety of the antisense oligonucleotide, wherein, in the identified target region, the 5'-most nucleotide is nucleotide position 88 or 114 of exon 10 or is between nucleotide positions 88 to 114 of exon 10, and wherein the identified target region enhances alternative splicing to exclude exon 10 and to generate a soluble form of RAGE; and further wherein the antisense oligonucleotide binds to the RAGE pre-mRNA within the identified target region; wherein the antisense oligonucleotide is 8 to 25 nucleotides in length; and wherein the antisense oligonucleotide comprises at least one modified nucleotide; thereby treating the disease.

24. The method of claim 23, wherein the disease associated with RAGE expression is selected from the group consisting of neurodegenerative disease, cancer, lung disorders, and inflammatory disease.

25. The method of claim 23, wherein the antisense oligonucleotide is 20 to 25 nucleotides in length.

26. The method of claim 1, wherein the target region of exon 10 of the RAGE pre-mRNA contains at least one guanine (G)-rich cis element and wherein the binding of the one or more antisense oligonucleotides within exon 10 flanks the G-rich cis element.

27. The method of claim 26, wherein the at least one guanine (G)-rich cis element is bound by a heterogeneous nuclear ribonucleoprotein H (hnRNP).

* * * * *

SEQUENCE LISTING

<160> NUMBER OF SEQ ID NOS: 75

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 3668

<400> SEQUENCE: 1
ccuccucgcc ugguucugga agaca                                              25

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 3669

<400> SEQUENCE: 2
uuggccccuc cucgccuggu                                                    20

<210> SEQ ID NO 3
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 3670

<400> SEQUENCE: 3
cugcaguugg ccccuccucg                                                    20

<210> SEQ ID NO 4
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 3671

<400> SEQUENCE: 4
ucaaaccccu caccugcagu                                                    20

<210> SEQ ID NO 5
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 4103

<400> SEQUENCE: 5
ccugcaguug gccccuccuc gccug                                              25

<210> SEQ ID NO 6

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 4104

<400> SEQUENCE: 6
ccccucaccu gcaguuggcc ccucc                                              25

<210> SEQ ID NO 7
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 4105

<400> SEQUENCE: 7
gcaguuggcc ccuccuc                                                       17

<210> SEQ ID NO 8
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 4106

<400> SEQUENCE: 8
caccugcagu uggccccucc ucgcc                                              25

<210> SEQ ID NO 9
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 3777

<400> SEQUENCE: 9
auccucccac agagccugua cggag                                              25

<210> SEQ ID NO 10
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 3778

<400> SEQUENCE: 10
cccugauccu cccacagagc cugua                                              25

<210> SEQ ID NO 11
<211> LENGTH: 25
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: AON 3779

<400> SEQUENCE: 11
ggcguugccg ccuuugccac aagau                                              25

<210> SEQ ID NO 12
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 3780

<400> SEQUENCE: 12
cucaccucuc cucccucgg cguug                                               25

<210> SEQ ID NO 13
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 3781

<400> SEQUENCE: 13
cuccacucac cucccucuc cucgg                                               25

<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 82

<400> SEQUENCE: 14
agcagggcgg cuguccccag                                                    20

<210> SEQ ID NO 15
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 83

<400> SEQUENCE: 15
gccacaagau gaccccaaug agcag                                              25

<210> SEQ ID NO 16
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 84
```

```
<400> SEQUENCE: 16
ccuuugccac aagaugaccc caaug                                          25

<210> SEQ ID NO 17
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 85

<400> SEQUENCE: 17
ugccgccuuu gccacaagau gaccc                                          25

<210> SEQ ID NO 18
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 87

<400> SEQUENCE: 18
uccucggcgu ugccgccuuu gccac                                          25

<210> SEQ ID NO 19
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 90

<400> SEQUENCE: 19
uuugccacaa gau                                                       13

<210> SEQ ID NO 20
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 93

<400> SEQUENCE: 20
ccgccuuugc cacaagauga                                                20

<210> SEQ ID NO 21
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 88

<400> SEQUENCE: 21
uuucuuguug accauccccc caguc                                          25
```

```
<210> SEQ ID NO 22
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 89

<400> SEQUENCE: 22 ccauccccc agucacaugu guugg                                          25

<210> SEQ ID NO 23
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 3672

<400> SEQUENCE: 23
ccuccucgcc ugguucugga agaca                                         25

<210> SEQ ID NO 24
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 3673

<400> SEQUENCE: 24
cuggccccuc aucgccgguu                                               20

<210> SEQ ID NO 25
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 3674

<400> SEQUENCE: 25
cuucagcugg ccccucaucg                                               20

<210> SEQ ID NO 26
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON 3675

<400> SEQUENCE: 26
uccagucccu caccuucagc                                               20

<210> SEQ ID NO 27
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON m3779

<400> SEQUENCE: 27
uggguugucg uuuucgccac aggau                                              25

<210> SEQ ID NO 28
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON m97

<400> SEQUENCE: 28
acuacuccca ggccucccag gau                                                23

<210> SEQ ID NO 29
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON m98

<400> SEQUENCE: 29
gcagggcuac uacucccagg ca                                                 22

<210> SEQ ID NO 30
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON m101

<400> SEQUENCE: 30
ucucacucac cucuccucac gccug                                              25

<210> SEQ ID NO 31
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON m102

<400> SEQUENCE: 31
cccagacuca cccacagagc cugua                                              25

<210> SEQ ID NO 32
<211> LENGTH: 50
<212> TYPE: DNA
<213> ORGANISM: Homo sapiens

<400> SEQUENCE: 32
```
aggactcttg tcccaaaggc atgaattcct agcattccct gtgacaagac         50

<210> SEQ ID NO 33
<211> LENGTH: 154
<212> TYPE: DNA
<213> ORGANISM: Homo sapiens

<400> SEQUENCE: 33
gactgaaaga tgggggctgg agagagggtg caggccccac ctagggcgga ggccacagca    60
gggagagggg cagacagagc caggaccctg gaaggaagca ggatggcagc cggaacagca   120
gttggagcct gggtgctggt cctcagtctg tggg                              154

<210> SEQ ID NO 34
<211> LENGTH: 25
<212> TYPE: DNA
<213> ORGANISM: Homo sapiens

<400> SEQUENCE: 34
gtgagccact ccctcaaccc cactg                                         25

<210> SEQ ID NO 35
<211> LENGTH: 25
<212> TYPE: DNA
<213> ORGANISM: Homo sapiens

<400> SEQUENCE: 35
cctctaccat ggtgctatct cccag                                         25

<210> SEQ ID NO 36
<211> LENGTH: 107
<212> TYPE: DNA
<213> ORGANISM: Homo sapiens

<400> SEQUENCE: 36
gggcagtagt aggtgctcaa aacatcacag cccggattgg cgagccactg gtgctgaagt    60 gtaaggggc cccaagaaa ccaccccagc ggctggaatg gaaactg                   107

<210> SEQ ID NO 37
<211> LENGTH: 25
<212> TYPE: DNA
<213> ORGANISM: Homo sapiens

<400> SEQUENCE: 37
gtaagcgggg ctcctgttgc agcct                                         25

<210> SEQ ID NO 38
<211> LENGTH: 25
<212> TYPE: DNA
<213> ORGANISM: Homo sapiens

<400> SEQUENCE: 38
ttaggccctg cttctctgct tctag                                         25

<210> SEQ ID NO 39
<211> LENGTH: 196
<212> TYPE: DNA
<213> ORGANISM: Homo sapiens

<400> SEQUENCE: 39
aacacaggcc ggacagaagc ttggaaggtc ctgtctcccc agggaggagg ccctgggac     60 agtgtggctc gtgtccttcc caacggctcc ctcttccttc cggctgtcgg gatccaggat    120 gagggattt tccggtgcca ggcaatgaac aggaatggaa aggagaccaa gtccaactac    180
cgagtccgtg tctacc                                                    196

<210> SEQ ID NO 40
<211> LENGTH: 25
<212> TYPE: DNA
<213> ORGANISM: Homo sapiens

<400> SEQUENCE: 40
gtaagaattc cagggtcttc tccaa                                          25

<210> SEQ ID NO 41
<211> LENGTH: 25
<212> TYPE: DNA
<213> ORGANISM: Homo sapiens

<400> SEQUENCE: 41
tctgactgga ttttcctcc ttcag                                           25

<210> SEQ ID NO 42
<211> LENGTH: 65
<212> TYPE: DNA
<213> ORGANISM: Homo sapiens

<400> SEQUENCE: 42
agattcctgg gaagccagaa attgtagatt ctgcctctga actcacggct ggtgttccca    60
ataag                                                                65

<210> SEQ ID NO 43
<211> LENGTH: 25
<212> TYPE: DNA
<213> ORGANISM: Homo sapiens

<400> SEQUENCE: 43
gtagtggaag aaagcaggag aagta                                          25

<210> SEQ ID NO 44
<211> LENGTH: 25
<212> TYPE: DNA
<213> ORGANISM: Homo sapiens

<400> SEQUENCE: 44
tctgaggtca ccactctttc cccag                                          25

<210> SEQ ID NO 45
<211> LENGTH: 88
<212> TYPE: DNA
<213> ORGANISM: Homo sapiens

<400> SEQUENCE: 45
gtggggacat gtgtgtcaga gggaagctac cctgcaggga ctcttagctg gcacttggat    60
gggaagcccc tggtgcctaa tgagaagg                                       88

<210> SEQ ID NO 46
<211> LENGTH: 25
<212> TYPE: DNA
<213> ORGANISM: Homo sapiens

<400> SEQUENCE: 46
gtgagtccta aggtgccccc caagc                                          25

```
<210> SEQ ID NO 47
<211> LENGTH: 25
<212> TYPE: DNA
<213> ORGANISM: Homo sapiens

<400> SEQUENCE: 47
aatttgtctt atcctcccat catag                                         25

<210> SEQ ID NO 48
<211> LENGTH: 183
<212> TYPE: DNA
<213> ORGANISM: Homo sapiens

<400> SEQUENCE: 48
gagtatctgt gaaggaacag accaggagac accctgagac agggctcttc acactgcagt   60
cggagctaat ggtgacccca gcccggggag gagatccccg tcccaccttc tcctgtagct  120
tcagcccagg ccttccccga caccgggcct tgcgcacagc ccccatccag ccccgtgtct  180
ggg                                                                183

<210> SEQ ID NO 49
<211> LENGTH: 25
<212> TYPE: DNA
<213> ORGANISM: Homo sapiens

<400> SEQUENCE: 49
gtgagcatag gtggggaggg cccca                                         25

<210> SEQ ID NO 50
<211> LENGTH: 25
<212> TYPE: DNA
<213> ORGANISM: Homo sapiens

<400> SEQUENCE: 50
acctcaaaac ccttccaact cccag                                         25

<210> SEQ ID NO 51
<211> LENGTH: 131
<212> TYPE: DNA
<213> ORGANISM: Homo sapiens

<400> SEQUENCE: 51
agcctgtgcc tctggaggag gtccaattgg tggtggagcc agaaggtgga gcagtagctc   60
ctggtggaac cgtaaccctg acctgtgaag tccctgccca gccctctcct caaatccact  120
ggatgaagga t                                                       131

<210> SEQ ID NO 52
<211> LENGTH: 25
<212> TYPE: DNA
<213> ORGANISM: Homo sapiens

<400> SEQUENCE: 52
gtgagtgacc tggagagagg ggctg                                         25

<210> SEQ ID NO 53
<211> LENGTH: 25
<212> TYPE: DNA
<213> ORGANISM: Homo sapiens

<400> SEQUENCE: 53
```

```
gtctcctctc cccttccccc accag                                          25
```

<210> SEQ ID NO 54
<211> LENGTH: 142
<212> TYPE: DNA
<213> ORGANISM: Homo sapiens

<400> SEQUENCE: 54

```
ggtgtgccct tgccccttcc ccccagccct gtgctgatcc tccctgagat agggcctcag    60
gaccagggaa cctacagctg tgtggccacc cattccagcc acgggcccca ggaaagccgt   120
gctgtcagca tcagcatcat cg                                           142
```

<210> SEQ ID NO 55
<211> LENGTH: 25
<212> TYPE: DNA
<213> ORGANISM: Homo sapiens

<400> SEQUENCE: 55

```
gtgagacctc tccccaagcc ctaca                                          25
```

<210> SEQ ID NO 56
<211> LENGTH: 25
<212> TYPE: DNA
<213> ORGANISM: Homo sapiens

<400> SEQUENCE: 56

```
gactggatcc aactttgtct tccag                                          25
```

<210> SEQ ID NO 57
<211> LENGTH: 27
<212> TYPE: DNA
<213> ORGANISM: Homo sapiens

<400> SEQUENCE: 57

```
aaccaggcga ggaggggcca actgcag                                        27
```

<210> SEQ ID NO 58
<211> LENGTH: 25
<212> TYPE: DNA
<213> ORGANISM: Homo sapiens

<400> SEQUENCE: 58

```
gtgaggggtt tgataaagtc aggga                                          25
```

<210> SEQ ID NO 59
<211> LENGTH: 25
<212> TYPE: DNA
<213> ORGANISM: Homo sapiens

<400> SEQUENCE: 59

```
ctcaattttc cctgtctccg tacag                                          25
```

<210> SEQ ID NO 60
<211> LENGTH: 127
<212> TYPE: DNA
<213> ORGANISM: Homo sapiens

<400> SEQUENCE: 60

```
gctctgtggg aggatcaggg ctgggaactc tagccctggc cctggggatc ctggaggcc    60 tggggacagc cgccctgctc attggggtca tcttgtggca aaggcggcaa cgccgaggag   120
aggagag                                                            127
```

<210> SEQ ID NO 61
<211> LENGTH: 25
<212> TYPE: DNA
<213> ORGANISM: Homo sapiens

<400> SEQUENCE: 61
gtgagtggag aaagccagac ccctc                                          25

<210> SEQ ID NO 62
<211> LENGTH: 25
<212> TYPE: DNA
<213> ORGANISM: Homo sapiens

<400> SEQUENCE: 62
cattcccccc aatctttctc ctcag                                          25

<210> SEQ ID NO 63
<211> LENGTH: 272
<212> TYPE: DNA
<213> ORGANISM: Homo sapiens

<400> SEQUENCE: 63
gaaggcccca gaaaaccagg aggaagagga ggagcgtgca gaactgaatc agtcggagga    60
acctgaggca ggcgagagta gtactggagg gccttgaggg gcccacagac agatcccatc   120
catcagctcc cttttctttt tcccttgaac tgttctggcc tcagaccaac tctctcctgt   180
ataatctctc tcctgtataa ccccaccttg ccaagctttc ttctacaacc agagcccccc   240
acaatgatga ttaaacacct gacacatctt gc                                 272

<210> SEQ ID NO 64
<211> LENGTH: 50
<212> TYPE: DNA
<213> ORGANISM: Homo sapiens

<400> SEQUENCE: 64
tcttgtgtgt ctgtgtgtgt gtatgagaca caacctcacc cctatacctt               50

<210> SEQ ID NO 65
<211> LENGTH: 160
<212> TYPE: DNA
<213> ORGANISM: Homo sapiens

<400> SEQUENCE: 65
gataaagtca gggaagcaga agatagcccc caacacatgt gactgggggg atggtcaaca    60
agaaaggaat ggtgagtggt ggtggctgtg ctctcaatttt tccctgtctc cgtacaggct  120
ctgtgggagg atcagggctg ggaactctag ccctggccct                         160

<210> SEQ ID NO 66
<211> LENGTH: 53
<212> TYPE: PRT
<213> ORGANISM: Homo sapiens

<400> SEQUENCE: 66

Ile Lys Ser Gly Lys Gln Lys Ile Ala Pro Asn Thr Cys Asp Trp Gly
1               5                   10                  15

Asp Gly Gln Gln Glu Arg Asn Gly Glu Trp Trp Trp Leu Cys Ser Gln
            20                  25                  30

Phe Ser Leu Ser Pro Tyr Arg Leu Cys Gly Arg Ile Arg Ala Gly Asn
        35                  40                  45

-continued

Ser Ser Pro Gly Pro
      50

<210> SEQ ID NO 67
<211> LENGTH: 6
<212> TYPE: PRT
<213> ORGANISM: Homo sapiens

<400> SEQUENCE: 67

Ser Gln Gly Ser Arg Arg
1               5

<210> SEQ ID NO 68
<211> LENGTH: 45
<212> TYPE: PRT
<213> ORGANISM: Homo sapiens

<400> SEQUENCE: 68

Pro Pro Thr His Val Thr Gly Gly Met Val Asn Lys Lys Gly Met Val
1               5                   10                  15

Ser Gly Gly Gly Cys Ala Leu Asn Phe Pro Cys Leu Arg Thr Gly Ser
            20                  25                  30

Val Gly Gly Ser Gly Leu Gly Thr Leu Ala Leu Ala Leu
        35                  40                  45

<210> SEQ ID NO 69
<211> LENGTH: 10
<212> TYPE: PRT
<213> ORGANISM: Homo sapiens

<400> SEQUENCE: 69

Leu Gly Gly Trp Ser Thr Arg Lys Glu Trp
1               5                   10

<210> SEQ ID NO 70
<211> LENGTH: 24
<212> TYPE: PRT
<213> ORGANISM: Homo sapiens

<400> SEQUENCE: 70

Val Val Val Ala Val Leu Ser Ile Phe Pro Val Ser Val Gln Ala Leu
1               5                   10                  15

Trp Glu Asp Gln Gly Trp Glu Leu
            20

<210> SEQ ID NO 71
<211> LENGTH: 21
<212> TYPE: DNA
<213> ORGANISM: Homo sapiens

<400> SEQUENCE: 71
gctatcttct gcttccctga c                                           21

<210> SEQ ID NO 72
<211> LENGTH: 160
<212> TYPE: DNA
<213> ORGANISM: Homo sapiens

<400> SEQUENCE: 72
ggggatcctg ggaggcctgg ggacagccgc cctgctcatt ggggtcatct tgtggcaaag    60
gcggcaacgc cgaggagagg agaggtgagt ggagaaagcc agaccctca gacctagggc    120

```
ttccaggcag caagcgaaga ggggtcgggg ggtggaacga                    160

<210> SEQ ID NO 73
<211> LENGTH: 160
<212> TYPE: DNA
<213> ORGANISM: Homo sapiens

<400> SEQUENCE: 73
caaaagtgaa actccatctc aaaaaaaaaa agaaagggaa agactccact ggggctccca    60
ctaaataacc ctctctcaac ccgaagtctt cctttctgac tggatccaac tttgtcttcc   120
agaaccaggc gaggaggggc caactgcagg tgagggttt                          160

<210> SEQ ID NO 74
<211> LENGTH: 143
<212> TYPE: DNA
<213> ORGANISM: Homo sapiens

<400> SEQUENCE: 74
agaagatagc ccccaacaca tgtgactggg gggatggtca acaagaaagg aatggtgagt    60
ggtggtggct gtgctctcaa ttttccctgt ctccgtacag gctctgtggg aggatcaggg   120
ctgggaactc tagccctggc cct                                           143

<210> SEQ ID NO 75
<211> LENGTH: 13
<212> TYPE: PRT
<213> ORGANISM: Homo sapiens

<400> SEQUENCE: 75

Asp Lys Val Arg Glu Ala Glu Asp Ser Pro Gln His Met
1               5                   10
```